US007063946B2

(12) United States Patent
Kenten et al.

(10) Patent No.: US 7,063,946 B2
(45) Date of Patent: Jun. 20, 2006

(54) METHODS, REAGENTS, KITS AND APPARATUS FOR PROTEIN FUNCTION ANALYSIS

(75) Inventors: John H. Kenten, Boyds, MD (US); Hans Biebuyck, Rockville, MD (US); Ilia Davydov, North Potomac, MD (US); Nisar Pampori, Frederick, MD (US); Steven Yan Cheng, Rockville, MD (US); Stefanie Nelson, Silver Spring, MD (US)

(73) Assignee: Meso Scale Technologies, LLC., Gaithersburg, MD (US)

( * ) Notice: Subject to any disclaimer, the term of this patent is extended or adjusted under 35 U.S.C. 154(b) by 100 days.

(21) Appl. No.: 10/238,960

(22) Filed: Sep. 10, 2002

(65) Prior Publication Data

US 2003/0207290 A1 Nov. 6, 2003

Related U.S. Application Data

(60) Provisional application No. 60/409,442, filed on Sep. 9, 2002, provisional application No. 60/363,498, filed on Mar. 11, 2002, provisional application No. 60/318,289, filed on Sep. 10, 2001, provisional application No. 60/318,293, filed on Sep. 10, 2001, provisional application No. 60/318,284, filed on Sep. 10, 2001.

(51) Int. Cl.
*C12Q 1/68* (2006.01)

(52) U.S. Cl. .......................................................... 435/6

(58) Field of Classification Search .................... 435/6, 435/7.1, 7.2, 7.92; 536/23.1; 530/350

See application file for complete search history.

(56) References Cited

U.S. PATENT DOCUMENTS

| | | | | |
|---|---|---|---|---|
| 5,240,863 | A | 8/1993 | Shibue et al. | |
| 5,308,754 | A | 5/1994 | Kankare et al. | |
| 5,324,637 | A * | 6/1994 | Thompson et al. | 435/68.1 |
| 5,492,817 | A | 2/1996 | Thompson et al. | |
| 5,597,910 | A | 1/1997 | Gudibande et al. | |
| 5,641,623 | A | 6/1997 | Martin | |
| 5,665,563 | A | 9/1997 | Beckler | |
| 5,766,960 | A | 6/1998 | Cornell et al. | |
| 5,846,485 | A | 12/1998 | Leland et al. | |
| 5,866,434 | A | 2/1999 | Massey et al. | |
| 6,103,489 | A | 8/2000 | Arakaki et al. | |
| 6,136,268 | A | 10/2000 | Ala-Kleme et al. | |
| 6,140,045 | A | 10/2000 | Wohlstadter et al. | |
| 6,207,369 | B1 * | 3/2001 | Wohlstadter et al. | 435/6 |
| 6,325,973 | B1 | 12/2001 | Leland et al. | |

FOREIGN PATENT DOCUMENTS

| | | |
|---|---|---|
| EP | 1 182 458 A1 | 2/2000 |
| EP | 0 770 876 B1 | 4/2001 |
| WO | WO 91 12079 | 8/1991 |
| WO | WO 96 14426 | 5/1996 |
| WO | WO 98 12539 | 3/1998 |
| WO | WO 99 58962 | 11/1999 |
| WO | WO 99 63347 | 12/1999 |
| WO | WO 00/54046 | 9/2000 |

OTHER PUBLICATIONS

Hoeltke et al. Biotin in vitro translation, nonradioactive detection of cell-free synthesized proteins. Biotechniques, vol. 18, No. 5, pp. 900-905, 1995.*

Lustig et al. Small pool expression screening: identification of genes involved in cell cycle control, apoptosis and early devlopment. Methods in enzymology, vol 283, pp. 83-99, 1997.*

He, M., et al., "Single step generation of protein arrays from DNA by cell-free expression and *in situ* immobilisation (PISA method)," *Nucl. Acids Res.* 29 (15): e73 (2001).

PCT International Search Report for International Application No. PCT/US02/28682, International Searching Authority (May 3, 2004).

Davydov and Varshavsky (2000) J. Biol. Chem., 275:22931-22941.

Tiganis et al. (1998) Mol. Cell. Biol. 18:1622-34.

Zubay, G. (1973) Ann. Rev. Genet. 7:267.

Pelham, H. R. B. and Jackson, R. J. (1976) Eur. J. Biochem. 67:247-56.

Pelham, H. R. B, et al. (1978), Eur. J. Biochem., vol. 82, 199-209.

Roberts, B. E. and Paterson, B. M. (1973) Proc. Natl. Acad. Sci. U.S.A., 70:2330-234.

Roberts, B. E., et al. (1975), Proc. Natl. Acad. Sci. U.S.A., 72:1922-1926.

Anderson, C., et al. (1983) Meth. Enzymol. 101, 635.

Walter, P. and Blobel, G. (1983) Meth. Enzymol. 96, 84-93.

Krieg, P. and Melton, D (1984) Nucl. Acids Res., 12:7057-69.

Spirin, et al. (1988) Science, 242:1162-1164.

Ryabova, et al. (1989) Nucl. Acid Res., 17(11):4412.

Baranov, et al. (1989) Gene, 84:463-466.

Craig,D., et al (1992) Nucleic Acids Res. 20:4987-4995.

Ohtsuka H, et al. (1997) Nucleic Acids Sym. Ser., 37:125-6.

(Continued)

*Primary Examiner*—Gary Benzion
*Assistant Examiner*—Cynthia Wilder
(74) *Attorney, Agent, or Firm*—Kramer Levin Naftalis & Frankel LLP; Barry Evans, Esq.

(57) ABSTRACT

Apparatus, systems, system components, methods, compositions, and reagents for determining the function and activity of peptides and proteins and for identifying and characterizing molecules that affect these functions and activities. More specifically, methods and reagents used to determine the various activities of peptides and proteins including their binding specificity, binding activity, their enzymatic activity and their ability to act as substrates for enzymes. The disclosed methods are especially suited for the analysis of peptide and protein function where large numbers of peptides and proteins need to be analyzed.

52 Claims, 3 Drawing Sheets

OTHER PUBLICATIONS

Hoeltke HJ. et al. (1995) Biotechniques. 18(5):900-4, 906-7.
Kurzchalia TV, et al. (1988) Eur J Biochem. 172(3):663-8.
McIntosh B, et al. (2000) Biochimie. 82(2):167-74.
Gite S, et al. (2000) Anal Biochem. 279(2):218-25.
Janiak F, et al. (1990) Biochemistry, 29(18):4268-77.
Gao, Z-H. (2000) Biochem Biophys Res Comm, 268, 562-566.
Shimizu et al. (2001) Nature Biotechnology 9, 751-755.
Bertz, N. (2001) Promega Notes 77.
Zhu, H, et al. (2000) Nature Genetics, 26(3), 283-289.
Sawasaki, T, et al. (2002) PNAS, 99(23), 14652-14657.
Kobs, G, et al., Promega Note 77, year unknown.
Proteolink™, Promega Catalog (2001).
In vitro Expression Guide, Promega Catalog.

* cited by examiner

METHODS, REAGENTS, KITS AND APPARATUS FOR PROTEIN FUNCTION ANALYSIS

1. CROSS REFERENCES TO RELATED APPLICATIONS

This application claims priority to U.S. Provisional Application No. 60/318,284, filed Sep. 10, 2001; U.S. Provisional Application Ser. No. 60/318,293, filed Sep. 10, 2001; U.S. Provisional Application Ser. No. 60/318,289, filed Sep. 10, 2001; U.S. Provisional Application Ser. No. 60/363,498, filed Mar. 11, 2002; and U.S. Provisional Application No. 60/409,442, filed Sep. 9, 2002, entitled: "Methods, Reagents, Kits and Apparatus for Protein Function", each of which are hereby incorporated by reference.

2. FIELD OF THE INVENTION

This invention provides apparatus, systems, system components, methods, compositions, and reagents for determining the function and activity of peptides and proteins and for identifying and characterizing molecules that affect these functions and activities. The methods and reagents of the invention are used to determine the various activities of peptides and proteins including their binding specificity, binding activity, their enzymatic activity and their ability to act as substrates for enzymes. This invention is especially suited for the analysis of peptide and protein function where large numbers of peptides and proteins need to be analyzed.

3. BACKGROUND OF THE INVENTION

The steps involved in the transcription and translation (expression) of genes in cells are complex but the basic steps for protein to be produced from DNA are transcription and translation. The DNA is first transcribed into RNA, and then the RNA is translated by the interaction of various cellular components into protein. In prokaryotic cells transcription and translation are coupled, meaning that RNA is translated into protein during the time that it is being transcribed from the DNA. In eukaryotic cells the two activities are separate, making the overall process more complicated. DNA is transcribed into RNA inside the nucleus of the cell, but the RNA is further processed into mRNA and then transported outside the nucleus to the cytoplasm where it is translated into protein.

The ability of molecular biologists to isolate and clone genes has brought about the development of systems that can be used to express the proteins encoded by these genes or their corresponding mRNA messages. Methods for expressing proteins make it possible to manipulate genes and then study the effect of the manipulations on their function. The amount of protein to be produced, whether the gene is prokaryotic or eukaryotic and the relative merits of an in vitro cell-free or an in vitro whole-cell system, are some of the factors considered by researchers when selecting an expression system.

In vitro transcription systems using prokaryotic or eukaryotic cells are available; however, these systems are difficult to work with since intact cells are used. In vitro cell-free systems, on the other hand, are made from cell-free extracts produced from prokaryotic or eukaryotic cells that contain all the necessary components to translate DNA or RNA into protein. Cell-free extracts can be prepared from prokaryotic cells such as *E. coli* and from eukaryotic cells such as rabbit reticulocytes and wheat germ. Cell-free systems are very popular because there are standard protocols available for their preparation and because they are commercially available from a number of sources. Although in vitro systems have many advantages to major draw back is that the amounts of protein produced is generally low which makes the analysis of protein function and activity difficult. The problems with low levels of protein production have forced researchers to develop complex assay systems using gel based systems and radioactivity that limit the application of these in vitro methods for studies of protein function and activity.

*E. coli* S30 cell-free extracts were first described by Zubay, G. (1973 Ann. Rev. Genet. Vol 7, p. 267). These extracts can be used when the gene to be expressed has been cloned into a vector containing the appropriate prokaryotic regulatory sequences, such as a promoter and ribosome-binding site. Prokaryotic *E. coli* cell-free systems are considered coupled because transcription and translation occur simultaneously after the addition of DNA to the extract.

Rabbit reticulocyte lysate was described by Pelham, H. R. B. and Jackson, R. J. (1976, Eur. J. Biochem. Vol. 67, p. 247). This expression system is probably the most widely used cell-free system for in vitro translation, and is used in the identification of mRNA species, the characterization of their products and the investigation of transcriptional and translational control.

Wheat germ extract was described by Roberts, B. E. and Paterson, B. M. (1973, Proc. Natl. Acad. Sci. U.S.A., Vol. 70, P. 2330). Cell-free extracts of wheat germ support the translation in vitro of a wide variety of viral and other prokaryotic RNAs, as well as eukaryotic mRNAs. (Anderson, C., et al. (1983) Meth. Enzymol. 101, 635). Generally, it is found necessary to include a ribonuclease inhibitor in the reaction mix of a wheat germ translation system, as ribonuclease activities in wheat germ extract are present.

Post-translational modifications that have been observed in rabbit reticulocyte lysate or wheat germ extract include signal peptide cleavage, glycosylation, acetylation, isoprenylation, proteolysis myristoylation, protein folding and proteolytic processing (Glass, C. A. and Pollard, K. M. (1990). Promega Notes 26). Some modifications or processing events have required the introduction of additional biological machinery. For example, processing events, such as signal peptide cleavage and core glycosylation, are examined by adding canine microsomal membranes (Walter, P. and Blobel, G. (1983) Meth. Enzymol. 96, 84) (Walter, P. and Blobel, G. (1983) Meth. Enzymol. 96, 84) or Xenopus egg extracts (Zhou, X, et al. U.S. Pat. No. 6,103,489) to a standard translation reaction. The addition of membrane preps is valuable when investigating membrane bound proteins such as receptors. These in vitro systems have been used to express many proteins, often in their native conformation and containing many of the normal and expected post-translational modifications.

RNA for translational studies can be obtained by either isolating mRNA or by making in vitro RNA transcripts from DNA that has been cloned into a vector containing an RNA polymerase promoter. The first method isolates mRNA directly from cells. The second obtains RNA for in vitro translation by in vitro transcription. In vitro transcription of cloned DNA behind phage polymerase promoters was described by Krieg, P. and Melton, D (1984, Nucl. Acids Res., Vol. 12, p. 7057). This method has become a standard method for obtaining RNA from cloned genes for use in in vitro translation reactions. The method uses DNA or a gene of interest that is cloned into a vector containing a promoter for an RNA polymerase. The vector is then purified and followed by an in vitro transcription reaction to make RNA transcripts. A number of vectors containing the SP6, T7 and T3 RNA polymerase promoters are commercially available and are widely used for cloning DNA.

After rabbit reticulocyte lysate and wheat germ extract were developed as cell-free translation systems, coupling of transcription and translation was demonstrated. One system that was developed was a linked transcription and translation system (Roberts, B. E., et al. (1975), Proc. Natl. Acad. Sci. U.S.A., Vol 72, 1922–1926). This system involved the use of wheat germ extract supplemented with *E coli* RNA polymerase and looked at transcription and translation of SV40 viral DNA. Another system was developed by Pelham, H. R. B, et al. (1978), Eur. J. Biochem., Vol. 82, 199–209, where coupled transcription and translation occurred after the introduction of vaccinia vital core particles into rabbit reticulocyte lysate.

Work has also been described using continuous cell-free in vitro translation systems with the emphasis on large-scale production of protein. Continuous translation involves a bioreactor (such as an Amicon 8MC ultrafiltration unit) in which large scale reactions are set up and protein is continually translated over extended periods of time. The reaction requires that a buffer be fed into the reaction as it progresses, and also requires that the products of translation be removed from the reaction filter unit. This type of system works well with *E. coli* S30 extract and wheat germ extract when RNA template is introduced. See Spirin, et al. (1988) Science, Vol 242, 1162–1164. The system also works using RNA templates in rabbit reticulocyte lysate. See Ryabova, et al. (1989) Nucl. Acid Res., Vol. 17, No. 11, 4412. The system is also known to work well with DNA templates in *E. coli* S30 extracts. See Baranov, et al. (1989) Gene, Vol 84, 463–466. PCT publication WO9102076 discloses continuous cell-free translation from DNA templates using eukaryotic lysates.

These methods of coupling transcription and translation have been further modified by coupling these in vitro transcription and in vitro translation steps in a single reaction mix from plasmid DNA containing RNA polymerase sites for the SP6, T7 or T3 RNA polymerases (Craig, D., et al (1992) Nucleic Acids Res. Vol 20, 4987–4995, U.S. Pat. No. 5,665,563; U.S. Pat. No. 5,324,637; U.S. Pat. No. 5,492,817; EP566 714). These coupled reaction mixes are available commercially from Promega both for the rabbit reticulocyte and wheat germ lysates.

The proteins from these translation or transcription translation reactions have been labeled using a variety of methods. This step is important given the fact that very small amounts of protein are produced in these translation reactions relative to the total amount of protein (4–0.4 ug/ml relative to 50–60 mg/ml of endogenous proteins).

One labeling method is the genetic modification of the gene or genes of interest, which results in the translation of a protein containing amino acids, amino acid sequences or post-translational modifications not found in the normal translation product of the gene. These modifications provide for the use of various methods for detection and purification of the translated proteins. These methods for the modification of the normal gene product are not always helpful as they can prevent the normal function of the protein due to the modification of the N terminal or C terminal portions of the protein. Also these modifications can prove to be costly and time consuming when applied on large scale.

Another labeling method involves the use of radioactive amino acids in translation reaction resulting in the production of a labeled amino acid sequence that is encoded by the DNA or RNA used to drive the translation reaction. Radioactive labeled amino acid sequences produced this way have been valuable in the study, detection and determination of these protein function and properties. The problems that are associated with the use of radioactivity are well known and make its use on a large scale problematic, unsafe and costly.

An alternative in vitro approach uses specific tRNAs linked to modified amino acids to produce amino acid sequences incorporating these modifications (Ohtsuka H, et al., Nucleic Acids Symp Ser. 1997;(37):125–6. Hoeltke H J, et al., Biotechniques. 1995;18(5):900–4, 906–7. Kurzchalia T V, et al. Eur J Biochem. 1988;172(3):663–8. McIntosh B, et al., Biochimie. 2000;82(2):167–74. Gite S, et al., Anal Biochem. 2000;279(2):218–25. Janiak F, et al., Biochemistry. 1990 8; 29(18):4268–77.). The best example of this approach is with the use of a Lys tRNA that is modified to contain a biotin. The resulting biotinyl-Lys-tRNA is used in translation reactions resulting in the production of proteins labeled with Biotin at random within the protein sequence. This method has been used for the detection of proteins on gels and for the purification of proteins prior to gel based analysis. This method for labeling proteins in combination with gel based detection methods has not provided a solution for rapid or simple assays for protein activity or function. Indeed some groups have found that this labeling method would not work when used in a solid phase assay due to endogenous biotinylase activity and high levels of endogenous lysine which markedly inhibit the ability to incorporate significant amounts of biotinylated lysine into newly synthesized proteins (Gao, Z-H., (2000) Biochem Biophys Res Comm, 268, 562–566).

Thus these methods for producing proteins and labeling them to date do not allow for the facile analysis of protein function or activity.

In order to improve on this method for labeling proteins other derivatives of tRNA have been developed. One example is the lysine tRNA labeled with the fluorophore, BODIPY-FL (Promega, Madison Wis. (Promega Notes 77)). This has improved the detection methodologies but is still based on using gel electrophoresis and in gel detection systems that are expensive, slow and complex.

At this time, there are a number of commercially available instruments that utilize electrochemiluminescence (ECL) for analytical measurements including drug screening. Species that can be induced to emit ECL (ECL-active species) have been used as ECL labels. Examples of ECL labels include: i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863. The light generated by ECL labels can be used as a reporter signal in diagnostic procedures (Bard et al., U.S. Pat. No. 5,238,808). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369 and 5,589,136 and Published PCT Nos. WO99/63347; WO00/03233; WO99/58962; WO99/32662; WO99/14599; WO98/12539; WO97/36931 and WO98/57154.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells. Recently, ECL instrumentation has been disclosed that uses reagents immobilized on the electrode used to induce ECL (see, e.g., U.S. Pat. No. 6,207,369 and Published PCT Application No. WO98/12539). Multi-well plates having integrated electrodes suitable for such ECL measurements have also been recently disclosed (see, e.g., copending Provisional Application No. 60/301,932 entitled "Assay Plates, Reader Systems and Methods for Luminescence Test Measurements", filed on Jun. 29, 2001, and U.S. application Ser. Nos. 10/185,274 and 10/185,363, filed Jun. 28, 2002, each hereby incorporated by reference, each hereby incorporated by reference.

The use of multi-well assay plates allows for the parallel processing and analysis of multiple samples distributed in multiple wells of a plate. Typically, samples and reagents are stored, processed and/or analyzed in multi-well assay plates (also known as microplates or microtiter plates). Multi-well assay plates can take a variety of forms, sizes and shapes. For convenience, some standards have appeared for some instrumentation used to process samples for high throughput assays. Assays carried out in standardized plate formats can take advantage of readily available equipment for storing and moving these plates as well as readily available equipment for rapidly dispensing liquids in and out of the plates. Some well established multi-well plate formats include those found on 96-well plates (12×8 array of wells), 384-well plates (24×16 array of wells) and 1536-well plate (48×32 array of well). The Society for Biomolecular Screening has published recommended microplate specifications for a variety of plate formats (see, http://www.sbsonline.org), the recommended specifications hereby incorporated by reference.

4. SUMMARY OF THE INVENTION

This invention provides apparatus, systems, system components, methods, compositions, and reagents for determining the function and activity of peptides and proteins and for identifying and characterizing molecules that affect these functions and activities. The methods and reagents of the invention are used to determine the various activities of peptides and proteins including their binding specificity, binding activity, their enzymatic activity and their ability to act as substrates for enzymes. This invention is especially suited for the analysis of peptide and protein function where large numbers of peptides and proteins need to be analyzed.

One embodiment of the invention comprises a multiwell plate with a plurality of wells, preferably with at least 20 wells containing the in vitro transcription and translation products of at least one, and preferably plurality of, unique nucleic acid construct. The multiwell plate may advantageously have at least 40 wells or most advantageously at least 84 wells. The multi-well assay plates may have any number of wells of any size or shape, arranged in any pattern or configuration, and can be composed of a variety of different materials. Preferred embodiments of the invention use industry standard formats for the number, size, shape and configuration of the plate and wells. Examples of standard formats include 96-, 384-, 1536-, and 9600-well plates, with the wells configured in two-dimensional arrays. Other formats may include single well plates (preferably having a plurality of assay domains), 2 well plates, 6 well plates, 24 well plates, and 6144 well plates. Furthermore, the number of unique nucleic acid constructs advantageously is at least 2, more preferably at least 6, even more preferably at least 24, even more preferably at least 40, even more preferably at least 84 and most advantageously at least 300. Also the wells of the multiwell plate can comprise carbon or a carbon composite materials which may be used as solid phases in solid phase assays. The wells of the multiwell plate may include integrated electrodes which may also be used as solid phases in solid phase assays, preferably these are configured so that the multiwell plate is able to support electrochemiluminescence. Advantageously the in vitro transcription and translation is carried out in the presence of a tRNA precharged with a modified amino acid. In a preferred embodiment of the invention each well contains multiple zones or spots which allow multiple amino acid sequences containing the modified amino acids to be individually contacted to one of the multiple zones or spots in a well of a multiwell plate. Alternatively, amino acid sequences may be contacted with multiple zones in a well, e.g., to measure multiple different characteristics of an amino acid sequence.

The invention also comprises a multiwell plate with at least 20 wells containing the in vitro transcription and translation products of at least one unique nucleic acid construct and coated with the products of the in vitro transcription translation reaction. The multiwell plate may advantageously have at least 40 wells or most advantageously at least 84 wells. The multi-well assay plates may have any number of wells of any size or shape, arranged in any pattern or configuration, and can be composed of a variety of different materials. Preferred embodiments of the invention use industry standard formats for the number, size, shape and configuration of the plate and wells. Examples of standard formats include 96-, 384-, 1536-, and 9600-well plates, with the wells configured in two-dimensional arrays. Other formats may include single well plates (preferably having a plurality of assay domains), 2 well plates, 6 well plates, 24 well plates, and 6144 well plates. Furthermore, the number of unique nucleic acid constructs advantageously is at least 2, more preferably at least 6, even more preferably at least 24, even more preferably at least 40, even more preferably at least 84 and most advantageously at least 300. Also the wells of the multiwell plate can comprise carbon or a carbon composite materials which may be used as solid phases in solid phase assays. The wells of the multiwell plate may include integrated electrodes which may also be used as solid phases in solid phase assays, preferably these are configured so that the multiwell plate is able to support electrochemiluminescence. Advantageously the in vitro transcription and translation is carried out in the presence of a tRNA precharged with a modified amino acid. In a preferred embodiment of the multiwell plate each well contains multiple zones or spots which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence.

The invention comprises a multiwell plate containing beads with each well containing the in vitro transcription and translation products of at least one unique nucleic acid construct. The multiwell plate may advantageously have magnetic beads. Preferably, the in vitro transcription and translation is carried out in the presence of a tRNA precharged with a modified amino acid.

The invention also comprises a multiwell plate with at least 20 wells coated with a specific binding species that is used to bind the in vitro transcription and translation products of at least one unique nucleic acid construct. The invention also comprises these plates, wherein the well surfaces provide a solid phase which coated with the products of the in vitro transcription translation reaction, preferably via binding to the specific binding species. The multiwell plate may advantageously have at least 40 wells or most advantageously at least 84 wells. Also the number of unique nucleic acid constructs advantageously is at least 40 and most advantageously at least 84. Also the wells of the multiwell plate can comprise carbon or a carbon composite materials which may be used as solid phases in solid phase assays and/or to support the immobilized amino acid sequences. The wells of the multiwell plate may include integrated electrodes which may be used as solid phases in solid phase assays and/or to support the immobilized amino acid sequences, preferably these are configured so that the multiwell plate is able to support electrochemiluminescence. Preferably, the in vitro translation is carried out in the presence of a tRNA precharged with a modified amino acid. In a preferred embodiment of the multiwell plate each well contains multiple zones (sometimes referred to herein as assay domains or spots) which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence. In a preferred embodiment the specific binding species is selected from the nucleic acid, peptides or proteins.

The invention also comprises a multiwell plate with at least 20 wells coated with an amino acid sequence containing a modified amino acid that is produced as follows. Initially a nucleic acid construct is obtained and transcribed to generate RNA. This RNA is then translated in a cell-free translation system (preferably a cell lysate) containing a tRNA precharged with a modified amino acid, to produce an amino acid sequence containing the modified amino acid. These transcription and translation steps can also be combined in a single in vitro reaction. This amino acid sequence is then contacted with a well of a multiwell plate with at least 20 wells, where by a well surface coated with an amino acid sequence containing a modified amino acid is produced. The multiwell plate can contain at least 40 wells most advantageously the multiwell plate has at least 84 wells. Also the wells of the multiwell plate can comprise carbon or a carbon composite materials which may be used as solid phases in solid phase assays and/or to support the immobilized amino acid sequences. The wells of the multiwell plate may include integrated electrodes which may be used as solid phases in solid phase assays and/or to support the immobilized amino acid sequences, preferably these are configured so that the multiwell plate is able to support electrochemiluminescence. In a preferred embodiment of the multiwell plate each well contains multiple zones or spots which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence.

The invention also comprises a method of producing a multiwell plate with at least 20 wells coated with an amino acid sequence containing a modified amino acid. This is, preferably, produced by obtaining a nucleic acid construct and transcribing it to generate RNA. This RNA is then translated in a cell-free translation system containing a tRNA precharged with a modified amino acid, to produce an amino acid sequence containing a modified amino acid. These transcription and translation steps can also be combined in a single in vitro reaction. Amino acid sequences prepared in this way are then introduced into wells of a multiwell plate with at least 20 wells, where by a multiwell plate having wells coated with these amino acid sequences is produced. Also the wells of the multiwell plate can comprise carbon or a carbon composite materials which may be used as solid phases in solid phase assays and/or to support the immobilized amino acid sequences. The wells of the multiwell plate may include integrated electrodes which may be used as solid phases in solid phase assays and/or to support the immobilized amino acid sequences, preferably these are configured so that the multiwell plate is able to support electrochemiluminescence. In a preferred embodiment of the multiwell plate each well contains multiple zones or spots which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence.

The invention also comprises a method of producing a multiwell plate with at least 20 wells coated with an amino acid sequence containing a modified amino acid and post-translational modifications. This is, preferably, produced by obtaining one or a series of nucleic acid constructs followed by transcribing these to generate RNA. These RNA are then translated in a cell-free system (preferably a cell lysate) containing a tRNA precharged with a modified amino acid, to produce an amino acid sequence containing said modified amino acid and post translational modifications. These amino acid sequences are then introduced into wells of a multiwell plate with at least 20 wells, where by a multiwell plate coated with an amino acid sequence containing a modified amino acid and post-translational modifications is produced. Also the wells of the multiwell plate can comprise carbon or a carbon composite materials which may be used as solid phases in solid phase assays and/or to support the immobilized amino acid sequences. The wells of the multiwell plate may include integrated electrodes which may be used as solid phase supports in solid phase assays and/or to support the immobilized amino acid sequences, preferably these are configured so that the multiwell plate is able to support electrochemiluminescence. In a preferred embodiment of the multiwell plate each well contains multiple zones or spots which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence.

The invention also comprises a method of producing a multiwell plate with at least 20 wells coated with an amino acid sequence containing a modified amino acid and post-translational modifications. This is, preferably, produced by obtaining one or a series of nucleic acid constructs followed by transcribing these to generate RNA. These RNAs are then translated in a cell-free system (preferably a cell lysate) containing a tRNA precharged with a modified amino acid, to produce an amino acid sequence containing said modified amino acid. These amino acid sequences are then introduced into wells of a multiwell plate with at least 40 wells, to coat said wells with amino acid sequences containing a modified amino acid. These coated multiwell plates are then contacted with an enzyme, where by a multiwell plate with at least 40 wells coated with an amino acid sequence containing a modified amino acid and a post-translational modification is produced. Also the wells of the multiwell plate can comprise carbon or a carbon composite materials which may be used as solid phases in solid phase assays. The wells of the multiwell plate may include integrated electrodes, preferably these are configured so that the multiwell plate is able to support electrochemiluminescence. In a preferred embodiment of the multiwell plate each well contains multiple zones or spots which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence.

The invention also comprises a method of producing a multiwell plate with at least 20 wells coated with an amino acid sequence containing a modified amino acid and post-translational modifications. This is, preferably, produced by obtaining one or a series of nucleic acid constructs and transcribing these nucleic acids to generate RNA. The RNA is then translated in a cell-free translation system (preferably a cell lysate) containing a tRNA precharged with a modified amino acid, to produce an amino acid sequence containing said modified amino acid. These amino acid sequences are then introduced into the wells of a multiwell plate with at least 20 wells, to coat said multiwell plate with an amino acid sequence containing a modified amino acid. These coated multiwell plates are then contacted with an enzyme effective at removing a post-translational modification. Following this treatment with this enzyme to remove the post-translational modifications the multiwell plate is contacted with a second enzyme, where by a multiwell plate with at least 20 wells coated with an amino acid sequence containing a modified amino acid and a post-translational modification is produced. Also the wells of the multiwell plate can comprise carbon or a carbon composite materials which may be used as solid phases in solid phase assays and/or to support the immobilized amino acid sequences. The wells of the multiwell plate may include integrated electrodes which may be used as solid phase supports in solid phase assays and/or to support the immobilized amino acid sequences, preferably these are configured so that the multiwell plate is able to support electrochemiluminescence. In a preferred embodiment of the multiwell plate each well contains multiple zones or spots which allow multiple amino acid sequences containing the modified amino acids each individually to be contacted to one of the multiple zones or spots in a well of a multiwell plate. Alternatively, amino acid sequences may be contacted with multiple zones in a well, e.g., to measure multiple different characteristics of an amino acid sequence.

The invention also comprises a method for screening nucleic acid constructs for those encoding amino acid sequences subject to post-translational modifications. This is, preferably, achieved as follows. A nucleic acid construct is obtained and transcribed to generate RNA. This RNA is then translated in a cell-free translation system containing a tRNA precharged with a modified amino acid, to produce an amino acid sequence containing said modified amino acid. This amino acid sequence is then subjected to the detection of its post-translational modifications using, preferably, a solid phase assay. In one example, the amino acid-sequence is captured onto a solid phase using a binding species specific for the post-translational modification. Following this the captured amino acid sequences is detected on the solid phase using the modified amino acid. In another example, the amino acid sequence is captured onto a solid phase via a binding species specific for said modified amino acid. This captured amino acid sequence is then subject to detection using, e.g., a binding species specific for the post-translational modification. Amino acid sequences having the desired activity may be identified from their nucleic acid sequence.

The invention also comprises a method for screening nucleic acid constructs for those encoding amino acid sequences subject to post-translational modifications. This is, preferably, achieved as follows. A nucleic acid construct is obtained and transcribed to generate RNA. This RNA is then translated in a cell-free translation system containing a tRNA precharged with a modified amino acid and a substrate for a post-translational modification, to produce an amino acid sequence containing said modified amino acid and said post-translational modification. The detection of the post-translational modifications of the amino acid sequence is achieved using, preferably, a solid phase assay. In one example, the amino acid sequence is captured onto a solid phase via a binding species specific for said modified amino acid and detecting using a binding species specific for a post-translational modification. In another example, the amino acid sequence is captured onto a solid phase using a binding species specific for the post-translational modification. This is followed by detecting the captured amino acid sequences on the solid phase using, e.g., a binding species specific for the modified amino acid. Amino acid sequences having the desired activity may be identified from their nucleic acid sequence.

The invention also comprises a method for screening nucleic acid constructs for those encoding amino acid sequences subject to post-translational modifications. This is, preferably, achieved as follows. A nucleic acid construct is obtained and transcribed to generate RNA. The RNA is translated in a cell-free translation system containing a tRNA precharged with a modified amino acid and a substrate for a post-translational modification modified with a label, to produce an amino acid sequence containing the modified amino acid and the post-translational modification. The post-translational modifications of the amino acid sequence are, preferably, detected using a solid phase assay. In one example, the amino acid sequence is captured onto a solid phase via a binding species specific for said modified amino acid and detected using the label on the post-translational modification. In another example, the amino acid sequence is captured onto a solid phase via a binding species for the label on the post-translational modification and detected using the modified amino acid. Amino acid sequences having the desired activity may be identified from their nucleic acid sequence. Examples of binding species specific for post-translational modifications include antibodies, antibodies to ubiquitin and antibodies to phosphotyrosine.

The invention also comprises a method for screening nucleic acid constructs for those encoding amino acid sequences with enzymatic activity, preferably, comprising the following steps. A nucleic acid construct is obtained and transcribed to generate RNA. The RNA is translated in a cell-free system containing a tRNA precharged with a modified amino acid, to produce an amino acid sequence containing the modified amino acid. The enzymatic activity of the amino acid sequence is preferably detected using a solid phase assay. In one example, the amino acid sequence is captured onto a solid phase via a binding species specific for the modified amino acid, enzyme reaction buffer is added and the product of the enzyme activity is detected. Amino acid sequences having the desired activity may be identified from their nucleic acid sequence.

The invention also comprises a method for screening nucleic acid constructs for those encoding amino acid sequences that are substrates of enzymatic activity comprising, preferably, the following steps. A nucleic acid construct is obtained and transcribed to generate RNA. The RNA is translated in a cell-free system containing a tRNA precharged with a modified amino acid, to produce an amino acid sequence containing the modified amino acid. The amino acid sequences which are substrates of an enzyme activity are detected using, preferably, a solid phase assay. In one example, the amino acid sequences are captured onto a solid phase via a binding species specific for the modified amino acid, an enzyme is added and the product of the enzyme activity is detected. Amino acid sequences having the desired activity may be identified from their nucleic acid sequence. Preferably, the amino acid sequences are pretreated prior to contact with the enzyme activity to add or remove a post-translational modification.

The invention also comprises a method for screening nucleic acid constructs for those encoding amino acid sequences with binding activity comprising, preferably, the following steps. A nucleic acid construct is obtained and transcribed to generate RNA. The RNA is translated in a cell-free system containing a tRNA precharged with a modified amino acid, to produce an amino acid sequence containing the modified amino acid. The binding activity towards a binding partner is, preferably, detected in a solid phase assay. In one example, the assay comprises capturing the amino acid sequence onto a solid phase by binding it to a binding partner immobilized on the solid phase and detecting the captured amino acid sequence using the modified amino acid. In another example, the assay comprises capturing the amino acid sequence on a solid phase via a binding reagent specific for the modified amino acid and detecting the binding partner on the solid phase. Amino acid sequences having the desired activity may be identified from their nucleic acid sequence.

The invention also comprises a method for screening nucleic acid constructs for those encoding amino acid sequences with binding activity comprising, preferably, the following steps. A nucleic acid construct is obtained and transcribed to generate RNA. The RNA is translated in a cell-free system containing a tRNA precharged with a modified amino acid, to produce an amino acid sequence containing the modified amino acid. The binding activity of the amino acid sequence for a binding partner is measured, preferably, using a solid phase assay. In one example, the assay comprises contacting the amino acid sequence with a solid phase coated with a binding species specific for the modified amino acid, contacting the amino acid sequence with the binding partner, and detecting complexes having the binding partner on the solid phases. The immobilizing step may occur before, during or after, the contacting step. Alternatively, binding partner is captured on the solid phase and the modified amino acid is detected. Amino acid sequences having the desired activity may be identified from their nucleic acid sequence.

The invention also comprises a method for screening nucleic acid constructs for those encoding amino acid sequences with binding activity comprising, preferably, the following steps. A first nucleic acid and second nucleic acid construct are obtained and transcribed to generate a first and second RNA. The first RNA is translated in a cell-free system containing a tRNA precharged with a modified amino acid comprising a first binding species, to produce a first amino acid sequence containing said first binding species. The second RNA is translated in a cell lysate containing a tRNA precharged with a modified amino acid containing a detectable species, to produce a second amino acid sequence containing the detectable species. The binding of the two amino acid sequences is detected using, preferably, a solid phase assay. In one example, the assay comprises contacting a sample of the first amino acid sequence with the second amino acid sequence and capturing the binding species on a solid phase via a second binding species and detecting the detectable species bound to the solid phase. Amino acid sequences having the desired activity may be identified from their nucleic acid sequence.

The invention also comprises a method for screening nucleic acid constructs for those encoding amino acid sequences with nascent binding activity comprising, preferably, the following steps. A nucleic acid construct is obtained and transcribed to generate RNA. The RNA is translated in a cell lysate containing a tRNA precharged with a modified amino acid, to produce an amino acid sequence containing said modified amino acid. The amino acid sequence is captured onto a solid phase via a binding species specific for the modified amino acid and contacting with an enzyme to covalently modify the amino acid sequence. The binding of the modified amino acid sequence to a binding partner is detected, preferably, by a solid phase assay. In one example, the assay comprises contacting the amino acid sequence with a second binding species labeled with a detectable species and detecting the binding of the second binding species to the covalently modified solid phase. The second binding species may be labeled with a detectable label made using a method comprising the following steps: obtaining a nucleic acid construct, and transcribing the construct to generate RNA and translating said RNA in a cell lysate containing a tRNA precharged with a second modified amino acid, to produce an amino acid sequence containing the second modified amino acid.

This invention provides the identification of kinase activity for proteins that had not previously been demonstrated to have in vitro kinase activity. It also comprises methods for the determination of kinase activity. These kinases that can be used for the screening of compound libraries for inhibitors or activators of these kinases. This invention also provides for assays that allow the investigation of the activity of these kinase isolated from cells and or tissue samples for both studies into disease and diagnostic applications.

The invention also comprises a method for screening for antigens that bind antibodies comprising, preferably, the following steps. A nucleic acid construct is obtained and transcribed to generate RNA. The RNA is translated in a cell-free system to produce an amino acid sequence. The binding of the amino acid sequence to an antibody is, preferably, measured using a solid phase assay. In one example, the amino acid sequence is immobilized on a solid phase and contacted with an antibody. Binding of the antibody to the solid phase is detected by measuring the amount of antibody on the solid phase. Alternatively, the antibody may be immobilized and the assay may involve measuring the amount of the amino acid sequence on the solid phase. Amino acid sequences having the desired activity may be identified from their nucleic acid sequence.

5. BRIEF DESCRIPTION OF THE FIGURES

6. DETAILED DESCRIPTION OF THE INVENTION

Figure 1:
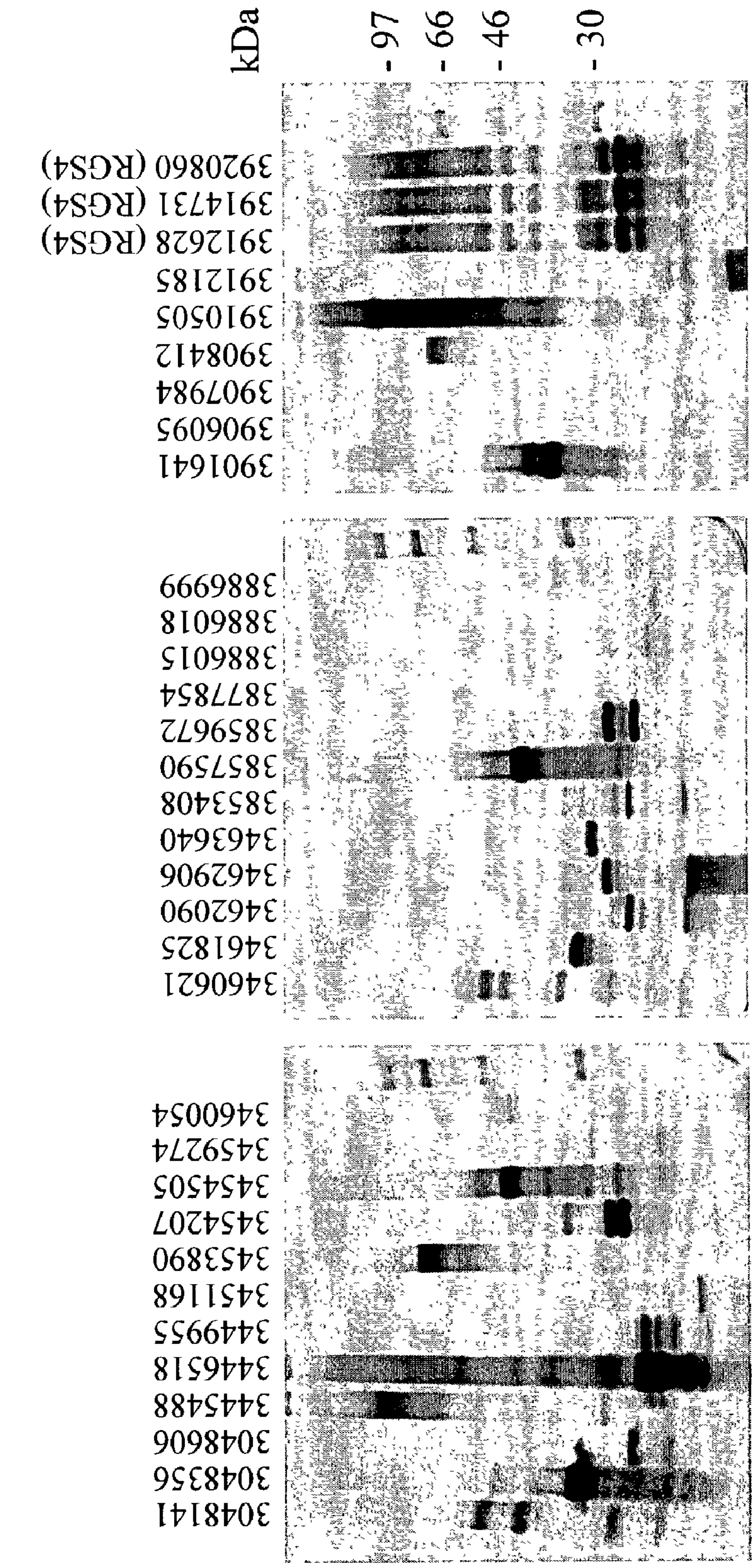
FIG. 1 is a gel electrophoresis analysis of a transcription and translation reaction with a series of EST clones, each lane is identified with its IMAGE ID #.

The present invention relates to methods for producing proteins and identifying protein function, structure and/or activity. The invention also provides for compositions, systems and apparatuses for accomplishing these methods. Advantageously, preferred methods of the invention employ proteins produced by in vitro cell-free transcription and translation systems and are tolerant of high levels of impurities in the protein preparations. By simplifying the processing of expressed proteins, the methods of the invention are especially conducive to the rapid, parallel, processing and/or screening of large numbers of proteins.

Through the use of the methods of the invention, large numbers of proteins (preferably greater than 80, more preferably greater than 1000, more preferably greater than 10,000 and most preferably greater than 20,000) may be screened, preferably in parallel, for specific functional or structural attributes of interest. These attributes include, but are not limited to, the group consisting of: i) binding activity (i.e., the ability to participate in a binding interaction with a binding partner); ii) enzymatic activity; iii) chemical reactivity; iv) substrate activity (i.e., the ability to act as a substrate an enzyme or other catalyst); v) post-translational modification; and vi) regulatory activity (e.g., the ability to alter the regulation of a cell or other complex biological or biochemical system).

Advantageously, the same methods used to screen for protein activity are also suitable for screening for molecules that modulate that activity by carrying out the measurement of activity in the presence of potential modulators and measuring the change in activity. Accordingly, one embodiment of the invention comprises expressing a library of proteins (preferably, in a multi-well plate format) by in vitro expression of a library of nucleic acid constructs encoding the proteins; screening the library of proteins for proteins with an activity of interest and screening one or more proteins having the desired activity against a library of substances to identify modulators of the activity of these proteins.

In preferred embodiments, the proteins are produced by in vitro cell-free translation methods, preferably by coupled transcription/translation methods. Applicants have demonstrated that these techniques are amenable to the parallel synthesis of large numbers of proteins in multi-well plates. Surprisingly, the proteins produced from these cell-free systems may be analyzed without purification, although in some applications it may be advantageous to purify the proteins prior to analysis, e.g., to remove interfering activities from the cell-free protein synthesis reagent. In especially preferred embodiments, the protein synthesis methods are designed to produce proteins that share a common chemical moiety (e.g., a detectable label) that allow the proteins to be purified, immobilized or detected using a uniform set of conditions.

The proteins can be screened for a variety of attributes of interest using conventional detection techniques for measuring protein attributes (e.g., techniques based on measurements of fluorescence, electrochemiluminescence, chemiluminescence, radioactivity, refractive index, magnetic fields, light scattering, etc.), preferably, using detection techniques that are carried out in a high-throughput and/or highly parallel fashion. Activities of interest may be measured, e.g., via the measurement of the quantity of an analyte; the measurement of a property of a sample (e.g., temperature, luminescence, electrochemical activity, color, turbidity, etc.); the measurement of a chemical, biochemical and/or biological activity (e.g., an enzymatic activity); the measurement of a kinetic or thermodynamic parameter (e.g., the rate or equilibrium constant for a reaction), etc. The assay techniques may be involve the detection of labels or, alternatively may not require labels (e.g., refractive index based techniques such as surface plasmon resonance). The assay techniques may involve the detection of reactions of species in solution (homogenous assays) or may involve at least some species on a solid phase (solid phase or heterogeneous assays). Preferably, the screening assays are carried out in a parallel fashion in multi-well plates (e.g., 24, 96, 384, or 1536 well plates). Even more preferably, the assays are carried out using solid phase assay formats (e.g., assays that presence of the attribute of interest to the attachment or release of an assay component from a solid phase support). Most preferably, the assays are solid phase assays employing ECL detection. In certain preferred embodiments, a plurality of attributes of a protein are measured in one well of a multi-well plate, e.g., by using a patterned array of assay domains on a surface of the well, the different domains designed for measuring different attributes.

The association or dissociation of labels from a surface (e.g., as occurs in a solid phase binding assay) can be measured in a washed format or, if the detection technique is surface-selective, in an unwashed format. The surface (e.g., the working electrode surface of a well in an ECL multi-well plate) can be washed prior to contacting a solution (e.g., with a solution containing an ECL coreactant, such as TPA that provides an appropriate environment for the induction of ECL from ECL labels) so as to remove unbound labeled reagents ("washed" assay format). Alternatively, the wash step may be omitted and, if appropriate, reagents such as ECL coreactants are added without first removing unbound labeled reagents ("unwashed" assay format). The surface selectivity of ECL measurements, especially in measurements involving the use of electrodes as solid phase assay supports, allows ECL measurements to be carried out in washed or unwashed formats. Alternatively, unwashed heterogeneous assays may be carried out using other surface selective techniques such as surface proximity assay. In washed ECL assays, it is preferred that the ECL measurement be conducted within a short time period after the addition of the coreactant solution to avoid loss of signal due to dissociation of the reagent in a binding interaction. In the unwashed assay, the timing is less important because free ligand remains in solution and the effect of the addition of the ECL coreactant on the binding equilibrium is small. In this case, the ECL measurements may be conducted as long as 1 hr after addition of the ECL coreactant solution with only small changes in signal.

Preferably, the proteins to be analyzed are produced in a labeled form using an in vitro translation, e.g., by including tRNAs charged with labeled amino acids in the translation reaction. These proteins may be used either directly or after affinity purification using the attached label. These proteins are then either immobilized via the label or are detected via the label.

In one embodiment, the labeled protein is contacted with a capture reagent that is immobilized on a solid phase, the capture reagent binding to the label so as to immobilize the labeled protein on the solid phase. Attributes of the protein may then be measured by solid phase assay. For example, the proteins can be analyzed for specific structural features or post-translational modifications by contacting them with binding reagents (e.g., antibodies) that are specific for those structural features or post-translational modifications and measuring the formation of binding complexes (preferably, via the detection of a second label attached to the binding reagent). Alternatively binding activity is measured by contacting the proteins with potential binding partners (e.g., specific proteins, peptides, lipids, drugs, nucleic acids, sugars and oligosaccharides, etc.) and measuring the formation of binding complexes (preferably, via the detection of a second label attached to the potential binding partner). In another alternate embodiment, the proteins are analyzed for substrate activity by contacting them with an enzyme or other chemical modification reagent and measuring the modification of the protein, e.g., via a, preferably labeled, binding reagent specific for the modified or unmodified form (or, alternatively, by measuring the cleavage from or attachment to the protein of a labeled assay component. In another alternate embodiment, the enzymatic activity (e.g., kinase, phosphatase, protease, cyclase, lipase, nuclease, ligase, polymerase or glycosidase activity) of the protein is measured by contacting the immobilized protein with a enzymatic substrate and measuring the consumption of substrate or production of enzymatic product.

Analogous methods exist for analyzing proteins that are not directly immobilized via the label. In these cases, the binding partner or binding reagent, as described above, are preferably immobilized on a solid phase. The binding of the labeled test protein to the immobilized reagent is, preferably, detected via the detection of the label.

Post-translational modification, as used herein refers to structural modifications of proteins after they have been translated. These can be in the form of covalent modifications or non-covalent.

Examples of covalent post-translational modifications that can be detected according to the invention include signal peptide cleavage, phosphorylation, acetylation, adenylation, proteolysis, amino peptidase clipping, arginylation, disulphide bond formation and cleavage, amidation, glycosylation, isoprenylation, myristoylation, ubiquitination, SUMOlation, and covalent addition of proteins including Agp12 and Nedd8.

Examples of non-covalent post-translational modifications that can be detected according to the invention include changes in the structure or folding state of a given protein (e.g., denaturation) or its non-covalent interactions with other proteins, nucleic acid, carbohydrate, drugs, compounds or lipids. For example the alteration of prions structure from PrPc to PrPsc resulting in resistance to protease activity. Other examples include the binding of a protein as a homo or hetero polymer, insertion in to a lipid membrane, or binding to a glycosyl group, or binding to a drug or compound. Examples of drug or compound binding include for example the interaction of steroid receptors with a steroid.

In vitro translation systems may introduce post-translational modifications into translated proteins. Often, these post-translational modifications (especially as introduced using eukaryotic translation systems, in particular, the reticulyte systems) may indicative of post-translational modifications that are observed in vivo. Advantageously, the methods of the invention may be used to identify proteins that receive specific types of post-translational modifications.

In other applications, e.g., in assays for substrate activity, the post-translational modifications may be the same as the modifications which are introduced by, e.g., an enzyme of interest and may therefore interfere with the assay. In these applications, it may be advantageous to contact the protein with an demodifying activity that removes the interfering modification. Preferably, the protein is immobilized to simplify removal of the demodifying activity (e.g., via wash steps) prior to conduct of the assay. In other applications, it may be desirable to contact the protein with a modifying reagent to introduce post-translational modifications prior to conducting an assay. Some proteins may only show an activity after post-translational modification. Thus, an assay of the invention for a characteristic of protein (e.g., binding activity, substrate activity, enzymatic activity, etc.) may comprise the step of treating the protein with a modifying activity (this treatment is most preferably applied after immobilization of the protein on a solid phase) to uncover a nascent activity of the protein. Especially preferred treatments are protease treatment, phosphorylation and dephosphorylation. This technique enables the screening of proteins in different modification states and analysis of the effect of modifications on activity. Preferably, the protein is immobilized to simplify removal of the modification activity (e.g., via wash steps) prior to conduct of the assay. Optionally, the protein is first treated with demodifying activities then treated with modifying activities in order to ensure that the protein is in a defined, reproducible modification state.

The invention relates, in part, to the production and analysis of proteins formed by the in vitro transcription and translation of nucleic acid constructs. These nucleic acid constructs are characterized by their ability to direct an RNA polymerase to produce an RNA transcript that, in turn, is able to direct the synthesis of a protein or polypeptide sequence. The nucleic acid construct may comprise DNA and/or RNA (preferably, DNA) and may include regions that are single stranded, double stranded (through base pair binding to its complementary sequence), or partially double stranded. The nucleic acid constructs, preferably, contain an RNA polymerase promoter sequence that directs the activity of a RNA polymerase to copy at least a portion of the nucleic acid construct to produce an RNA transcript. This transcript, preferably, either encodes a protein or polypeptide or a portion of a protein or polypeptide. The proteins or polypeptides may correspond to amino acid sequences that are found in nature or may be man-made sequences (i.e., sequences not found in nature). The nucleic acid constructs may include synthetic nucleic acid analogs or derivatives that are capable of being copied by transcriptional machinery.

Preferred nucleic acid constructs include plasmid based cloning vectors containing a cloned DNA sequence of a protein or amino acid sequence (natural or man-made). These plasmid based vectors are, preferably, produced by growing the plasmids in *E. coli* cultures and purifying the plasmid DNA to obtain the DNA in a form that can be used. Alternate preferred nucleic acid constructs include DNA sequences that have been generated using PCR or other amplification protocols. Advantageously, the production of nucleic acid constructs by nucleic acid amplification avoids the use of cloning vectors and cloning protocols that involve transfer and amplification of the DNA in a host organism. In one embodiment, DNA and or RNA from an organism is amplified and engineered during the PCR to generate a nucleic acid construct of the invention that is able to direct the production of a RNA sequence under direction of a RNA polymerase. This RNA sequence is then able to produce the protein or proteins of interest via the translation of the RNA sequence.

Preferred cloning vectors used in the nucleic acid constructs of this invention include those that contain RNA polymerase sites positioned such that they will allow the production of an RNA strand from the cloned DNA. Suitable cloning vectors containing RNA polymerase sites are available from a number of commercial suppliers including Promega (Madison, Wis.) Invitrogen (Carlsbad, Calif.) Novagen (Madison, Wis.) Clontech (Palo Alto Calif.). Examples of the RNA polymerases are SP6, T7 and T3. Examples of cloning vectors that contain promoters for these polymerases include pSP72 (Promega, Madison Wis.), pCITE-2 and -4 (Novagen, Madison, Wis.). The methods for cloning in to these vectors are well known in the art and reagents and kits are commercially available (Invitrogen, Carlsbad, Calif. Clontech, Palo Alto, Calif.). Many clones are available in suitable vectors; especially preferred nucleic acid constructs include clones distributed by the I.M.A.G.E. Consortium (Lawrence Livermore National Lab, Livermore, Calif.).

Preferably, gene sequences of interest in vectors are correctly orientated relative to the RNA polymerase sites and within a reasonable distance such as from 0 to 2000 bases, ideally 0 to 500, most ideally 0 to 200. The methods for directionally cloning are well known in the art and are typically part of most cloning methods for mRNA. Alternatively the DNA sequences are cloned without directionality which results in a mixture of clones with the DNA sequence in both of the possible orientations relative to the RNA polymerase site.

Other suitable vectors for use with the invention are vectors that contain additional sequences to the previously described vectors which allow the cloning of the gene of interest in such a way that these additional sequences are incorporated into the transcribed RNA and thus into the translation products of these RNA's. This approach has been used for the cloning of many genes to allow the production of translation products that are fused to other sequences of amino acids that allows the translations products to be detected and or purified. These additional sequences of amino acids are typically referred to as affinity tags, epitope tags, or purification tags. Examples of such vectors include pGADT7, pGBKT7 (Clontech, Palo Alto Calif.) pcDNA5/FRT/V5-His-TOPO, pSecTag/FRT/V5-His-TOPO (Invitrogen, Carlsbad, Calif.). Examples of these affinity, epitope or purification tags include, V5, myc, His, FLAG, GST, and MBP.

Nucleic acid constructs can be replicated using standard nucleic acid replication methods including growth in culture (e.g., using standard methods for replicating plasmid DNA) and in vitro amplification methods such as PCR, NASBA (Romano J W, et al., Immunol Invest. 1997;26:15–28), rolling circle replication (Zhang D Y, et al., Mol Diagn. 2001, 6:141–50). These steps are, preferably, followed by purification of the constructs. Methods for the isolation of plasmid DNA are well known in the art; examples of commercially available kits are available from Promega (Madison Wis.) and Qiagen (Los Angeles, Calif.).

An alternative route to the nucleic acid constructs of the invention obviates the cloning steps and makes use of in vitro methods throughout. With these methods the sequences of interest are amplified using standard nucleic acid amplification methods such as RTPCR, PCR, NASBA and rolling circle amplification. Preferably, oligonucleotide primers (e.g., primers in a PCR amplification) are selected such that the amplification product includes the gene sequence of interest as well as other additional features such as an RNA polymerase recognition site, In more preferred embodiments, other additional features are engineered into the amplification product such as an ATG initiation codon (preferably, modified to match the Kozak sequence such as CCACCATGG to improve translation, see, e.g., Kozak, M., J. Mol Biol. (1987) 196, 947), a termination of translation site, a 3' UTR and/or a poly A sequence. Optionally a 5' internal ribosome entry site (IRES) may also be introduced. These features may be introduced into the amplification product by incorporating them (or their complement) within the primers that are used for amplification.

These primers are then used in an in vitro reaction with a sample containing the sequence of interest; examples of samples include mRNA, genomic DNA, cDNA, total RNA or cloned DNA. These sources of the sequences of interest may be purified or unpurified. In the case of purified DNA this typically would consist of a mixture of sequences that have been purified from the tissue or cell sample. In the case of unpurified material this could take the form of whole cells, tissue samples, cell lysates and tissue homogenates. Examples of methods suitable for use in the in vitro production of nucleic acid constructs of the invention are illustrated in the following publications (Bateman, J F. et al, Human Mutation, (1999) 13, 311. Kirshgesser, M. et al, (1998) 36, 567. Rao, V R., et al, (1999) J. Biol. Chem. 274, 37893).

Alternatively the nucleic acid constructs of the invention may be RNA generated using in vitro methods or via the use of viral RNA replication as found in Picornaviruses, Myxovirus, Reovirus and RNA bacterophage R17, Qb, MS2 and f2; using RNA dependent RNA polymerases. These RNA viruses can be used to clone and isolate specific genes using standard recombinant methods. Alternatively these RNA dependent RNA polymerases may direct the in vitro production of RNA for translation from an existing RNA template. The RNA template may be produced from a DNA clone or DNA sequence or from an in vitro constructed RNA template. This may be achieved for example with mRNA; initially the RNA is treated with calf intestinal phosphatase, to remove the 5' phosphate from partial transcripts, these treated RNAs are then treated with tobacco acid pyrophosphatase to remove the 5' mRNA cap, exposing the 5' phosphate. Following this step the modified mRNA is then ligated to a sequence effective in directing the activity of a RNA dependent RNA polymerase. These ligated and modified mRNA sequences are then hybridized to an RNA oligonucleotide that hybridizes to the 3' poly A and introduces a site for RNA dependent RNA polymerase. These RNA sequences are then made double stranded using a RNA dependent RNA polymerase followed by the synthesis of RNA for translation using a RNA dependent RNA polymerase that is activated by the sequence attached at the 5' end of the mRNA. Optionally the addition of the 5' sequence, for the RNA dependent RNA polymerase may be carried out with out the use of the calf intestinal phosphatase and tobacco acid pyrophosphatase steps that ensure that only full-length RNA sequences are subjected to the production of RNA for translation using the RNA dependent RNA polymerase.

In certain preferred embodiments of the invention, translation and, optionally, transcription of nucleic acid constructs to produce proteins is carried out in an assay plate used for carrying out an assay for an activity of interest (e.g., plates as described elsewhere in this specification having assay domains coated with i) a substrate of an activity, ii) a binding reagent specific for a substrate of an activity, iii) a binding reagent specific for a product of an activity, iv) a binding reagent specific for a post-translational modification of the translation products, v) a binding reagent suitable for immobilizing the translation products, etc.). The assays of the invention are then carried out in this same plate. Alternatively, in other preferred embodiments, the translation reaction is carried out in one container, preferably, the well of a multi-well plate and the translation products transferred to an assay plate for analysis. This embodiment may be advantageous when only small amounts of translation products are used in an assay.

The assays of the invention may detect or utilize binding interactions of binding species. Binding species, as used herein, is used to describe a molecular species that is able to bind to another molecular species, its binding partner. These binding interactions are characterized in that they are non covalent, or covalent having dissociation constants which are, preferably, lower than 1 mM, more preferably lower than 100 μM, more preferably lower than 10 μM and most preferably higher than 1 μM. Examples of binding species and binding partners include biotin, antibodies, streptavidin, avidin, EDTA, chelates (e.g., EDTA, NTA, IDA, etc.), antigens, fluorescein, haptens (e.g., fluorescein, digoxigenin, etc.), proteins, peptides, drugs, nucleic acids, nucleic acid analogues, lipids, carboyhydrates, protein A, protein G, protein L, receptors, ligands, inhibitors, lectins, enzymes, substrates, transition state analogues, mechanism based inhibitors, epitopes, affinity tags (e.g., epitope tags such as his(6), glutathione, Myc, S-tag, T7-Tag), etc.

The assays of the invention may utilize labels. Label or detectable label is used herein is used to describe a substance used to detect (directly or indirectly) a molecular species. The label may be the molecular species itself or it may be linked to the molecular species. In certain embodiments of the invention, labels are used in order to follow or track a given molecular species, for example, to determine its distribution and concentration (as, for example, a radiolabeled drug molecule is used to determine its pharmacological properties when introduced into an animal or patient). In alternative embodiments, a label is introduced into a binding species so as to allow the binding species to be used to track and/or determine the presence and/or amount of a binding partner of the binding species. For example, immunoassays using labeled antibodies (e.g., antibodies labeled with ECL labels) can be used to detect and determine binding partners (analytes) bound by the antibody. Examples of this approach are exemplified by the ECL-based clinical immunoassays sold by Roche Diagnostics (Indianapolis, Ind.) under the Elecsys tradename.

In some embodiments of the invention, labels are used which may be detected directly, e.g., on the basis of a physical or chemical property of the label (e.g., optical absorbance, fluorescence, phosphorescence, chemiluminescence, electrochemiluminescence, refractive index, light scattering, radioactivity, magnetism, catalytic activity, chemical reactivity, etc.). Examples of directly detectable labels include, radioactive labels, fluorescent labels, luminescent labels, enzyme labels, chemiluminescent labels, electrochemiluminescent labels, phosphorescent labels, light scattering or adsorbing particles (e.g., metal particles, gold colloids, silver colloids), magnetic labels, etc.

In other embodiments of the invention, labels are used which may be detected indirectly via interactions with species comprising directly detectable labels. These indirectly detectable labels are, preferably, binding species; these binding species readily allow the binding to a binding partner that is labeled with a directly detectable label. Examples of indirectly detectable labels include binding species as described above, e.g., antibodies, antigens, haptens, avidin, biotin, streptavidin, flourescein, nucleic acid sequences, nucleic acid analogue sequences, epitope tags (such as myc, FLAG, GST, MBP, V5), digoxigenin, etc.

Homologous when used herein is used to describe a molecular species' relationship with another molecular species. Two molecular species are homologous when they share a set of molecular properties such as composition, function or structure. In the case of nucleic acids and proteins, the extent of homology can be described in terms of the degree of sequence similarity. For example, two proteins or nucleic acids may be considered homologous when they have greater than 20% sequence in common, ideally greater than 30%, or preferentially more than 40% sequence in common. Homology can also be described for protein and nucleic acid sequences based on the data from a BLAST search of the sequences in the NIH genebank database. In BLAST 2.0, for example, an E value of 1 assigned to a hit from a homology search can be interpreted as meaning that in a database of the current size one might expect to see 1 match with a similar score simply by chance. Thus any E value less than 1 would not be expected to happen by chance and would indicate that the two sequences are homologous. This approach to description of homology can also be formally applied to other molecular characteristics such as structure as quantified using VAST or a similar protein structure searching algorithm (http://ncbi.nlm.nih-.gov/Structure/VAST/vast.shtml). The VAST p-value is a measure of the significance of the comparison, expressed as a probability. For example, if the p-value is 0.001 then the odds are 1000 to 1 against seeing a match of this quality by pure chance. Thus a VAST p-value of less than 0.001 demonstrates a significant degree of homology.

The invention relates, in part, to the production of proteins in cell free systems and the analysis of these proteins. Protein synthesis is, preferably, accomplished using cell lysates or extracts (crude or partially purified) that contain the machinery necessary for protein synthesis. This machinery is found in most living cells, however, certain cell types are preferred because of their high protein synthesis activity. Three preferred translation systems for producing proteins are the bacterial (more preferably *E coli* extract, most preferably *E coli* S30 cell free extract), plant germ (most preferably, wheat germ) and reticulocyte (most preferably, rabbit reticulocyte) lysate translation systems. Optionally, the cell lysates are supplemented with additional components such as ATP, tRNA, amino acids, RNA polymerases, microsomes, protease inhibitors, proteosome inhibitors, etc. that enhance the functioning of the translation machinery, provide a missing component of the machinery, inhibit protein degradation or provide an additional activity such as transcription or post-translational modification. In an alternate embodiment of the invention the cell-free system is reconstituted from individual purified or partially purified components (e.g., a reconstituted *E coli* translation system using recombinant components as described in Shimizu et al. (2001) Nature Biotechnology 19, 751–755). In another alternate embodiment, a cell-based translation system is used.

The *E. coli* systems are advantageous when a gene has been cloned into a vector with prokaryotic regulatory sequences, such as the promoter and ribosome binding site. These systems are coupled in that transcription and translation can occur simultaneously. The *E. coli* extract systems have been the subject of much optimization and allow the production of mg amounts of protein using large scale (1 ml) reactions fed with reagents through semi-permeable membranes.

Wheat germ and the rabbit reticulocyte based cell free systems are suitable for the translation of mRNA into proteins. Preferably, these lysates are supplemented with RNA polymerases so that they carry out both transcription, to generate the mRNA, and translation to produce protein thus producing what is called a coupled system as seen in *E. coli.* The lysates based on the wheat germ and the rabbit reticulocyte may also be supplemented with other components in order to introduce additional activities to these lysates. In one embodiment, a lysate is supplemented with microsomes (preferably, dog pancreatic microsome, preparations) or xenopus oocyte extract to allow for certain post-translation modifications as well as the processing of proteins which are secreted, inserted or associated with membranes.

In especially preferred embodiment, proteins are produced using a cell free translation system that is supplemented with tRNAs that are charged with labeled or amino acids so that the proteins incorporate the label. It is preferable to use a tRNA that corresponds to an amino acid with a hydrophilic or charged side chain (most preferably $tRNA_{lys}$) so as to make it more likely that the label will be found on the exterior of the protein. A variety of suitable charged tRNAs are commercially available including $tRNA_{lys}$ charged with lysines that are labeled on their side chains with fluorophores (such as fluorescein and BODIPY) or binding species (such as biotin). Most preferably, only a fraction of a specific tRNA (e.g., $tRNA_{lys}$) in a translation reaction (preferably, less than 50%, more preferably, <10%) is charged with a label so as to ensure that the number of incorporated labels in a protein molecule is low and that the labeling does not significantly influence the structure or functional properties of the protein.

In preferred embodiments of the invention, solid phase supports are used for purifying, immobilizing, or for carrying out solid phase activity assays for analyzing the activity of one or more expressed proteins. Examples of solid phases suitable for carrying out the methods of the invention include beads, particles, colloids, single surfaces, tubes, multiwell plates, microtitre plates, slides, membranes, gels and electrodes. When the solid phase is a particulate material it is, preferably, distributed in the wells of multi-well plates to allow for parallel processing of the solid phase supports. Proteins of interest or other assay reagents may be immobilized on the solid phase supports, e.g., by non-specific adsorption, covalent attachment or specific capture using an immobilized capture reagent that binds, preferably specifically, the protein or assay reagent of interest. Immobilization may be accomplished by using proteins or assay reagents that are labeled with binding species that form binding pairs with immobilized capture reagents. Optionally, a protein is immobilized on a solid phase; the solid phase is washed and the protein is analyzed; the wash step allows for the rapid purification of the protein from other, potentially interfering, components of the translation reaction. Optionally, a protein is treated, prior to analysis, to add or remove post-translational modifications.

Especially preferred solid phase supports are electrode surfaces integrated into the wells of multi-well plates. Such devices allow ECL measurements to be carried out in a high-throughput, highly parallel, fashion. Exemplary multi-well plates are disclosed in copending Provisional Application No. 60/301,932 entitled "Assay Plates, Reader Systems and Methods for Luminescence Test Measurements", filed on Jun. 29, 2001 (particularly in the description of Plate Type B, Type C, type D, and Type E in Example 6.1) and U.S. application Ser. Nos. 10/185,274 and 10/185,363, filed Jun. 28, 2002, each hereby incorporated by reference. The electrodes in such plates, preferably, comprise a carbon composite electrode material such a carbon ink.

The multi-well assay plate can incorporate the electrode in one or more wells of the plate. The assay region (e.g., a given well of a multi-well plate) may also comprise additional electrodes. Preferably at least one electrode in an assay region (a well of a multi-well plate) is suitable for use as a working electrode in an electrode induced luminescence assay, at least one electrode is suitable for use as counter electrode in an electrode induced luminescence assay. Optionally, there is at least one electrode that is suitable for use as a reference electrode (e.g., in a three electrode electrochemical system). The surface of the working electrode in an electrode induced luminescence assay can be used for immobilization of one or more assay components. Electrodes used in the multi-well assay plates of the invention are typically non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

The wells of multiwell plate can further comprise a plurality (e.g., 2 or more, 4 or more, 7 or more, 25 or more, 64 or more, 100 or more, etc.) of discrete assay domains. Multi-domain multiwell plates which are adapted to allow assay measurements to be conducted using electrode induced luminescence measurements (most preferably, electrochemiluminescence measurements) are described in copending Provisional Application No. 60/318,293 entitled "Methods and Apparatus for Conducting Multiple Measurements on a Sample", filed on Sep. 10, 2001, and U.S. application Ser. No. 10/238,391, entitled "Methods and Apparatus for Conducting Multiple Measurements on a Sample", filed on Sep. 10, 2002, each hereby incorporated by reference. Multiple assay domains patterned on a surface of a well (e.g., on an electrode in a well adapted for conducting electrode induced luminescence measurements) may be defined by physical boundaries which can include ledges or depressions in the surface, patterned materials deposited or printed on the surface, and or interfaces between regions of the surface that vary in a physical property (e.g., wettability). Such physical boundaries simplify the patterning of reagents on surfaces of a well by confining and preventing the spreading of small drops of reagents applied to an assay domain. By providing two levels of multiplexing (multiple wells per plate and multiple domains per well), Multi-domain multi-well (MDMW) Plates provide a variety of advantages over conventional multi-well plates that only have one assay domain per well. For example, a MDMW Plate having N wells and M assay domains per well allows a panel of M assays to be run on a plurality of N samples. Conducting the same series of assays on conventional N-well plates would require M plates, M times more sample and reagents, and considerably more pipetting and plate handling steps to achieve the same performance. Conducting the same series of assays on conventional array "chips" would involve the handling and movement of N chips and would likely not be compatible with standard plate handling equipment designed for use with multi-well plates. Conducting the same series of assays on a single ultra-high density multi-well plate with M×N wells would generally lead to reduced assay sensitivity (sample volume and, therefore, number of analyte molecules, tends to scale inversely with the density of wells on a plate) as well as to other problems associated with ultra-high density plate formats (e.g., expensive and complicated fluid dispensing equipment, lack of mixing, evaporative losses, trapping of air bubbles, inability to carry out wash steps, etc.).

Multi-well and Multi-domain Multi-well plates can be used in a plurality of diverse assays. In one assay format, the same analyte is measured at different assay domains within a well, the different assay domains being designed to measure a different property or activity of the analyte. Alternatively, an enzyme with multiple different activities is measured in a well comprising different assay domains that differ in their selectivity for each enzymatic activity of the enzyme (e.g., assay domains that comprise substrates for selected enzymatic activities and/or assay domains that are capable of capturing and measuring the substrates or products of selected enzymatic activity), that are designed to measure binding activities of the enzyme (e.g., assay domains comprising potential binding partners of the enzyme or that are designed to capture the enzyme so as to allow the measurement of interaction with potential binding partners in solution) and/or assay domains designed to measure the ability of the enzyme to act as a substrate for a second enzyme (e.g., a binding domains designed to allow for a specific binding assay of the product of the action of the second enzyme on the first enzyme). In another assay format, a well comprises a domain for measuring the amount of an enzyme (e.g., via a binding assay such as an immunoassay) and one or more other domains for measuring one or more activities associated with the enzyme; this allows the measured activity to be referenced to the amount of enzyme. The inclusion of assay domains capable of capturing an enzyme of interest has the added advantage of allowing the purification of the enzyme from a crude sample within the assay well and/or the pretreatment of the enzyme with a modifying activity that exposes a nascent activity of the enzyme. A well may also comprise an assay domain capable of capturing an enzyme of interest and one or more additional assay domains for measuring an activity of the enzyme of interest. Methods using such a well may include a wash step for purifying the enzyme from impurities in a crude enzyme preparation.

In an embodiment of the invention, a series of nucleic acid constructs is obtained with the genes of interest located within the construct such that the gene of interest can be transcribed into RNA that can direct the synthesis of the protein encoded by the genes of interest. The nucleic acid from these is then subjected to an in vitro transcription reaction and followed by an in vitro translation reaction. These two reactions can also be combined in a single in vitro reaction. During the translation reaction the protein produced in the transcription and translation reaction is also labeled using a modified tRNA that directs the incorporation of a modified amino acid during this step.

Following the transcription and translation reaction the proteins produced in the mix may be captured on to a solid phase. Examples of solid phases suitable for carrying out the methods of the invention include beads, particles, colloids, single surfaces, tubes, multiwell plates, microtitre plates, slides, membranes, gels and electrodes. The capture of the proteins is achieved using a binding partner specific for the modification introduced by the modified tRNA during the translation reaction. A good example of how this is achieved is by the use of the biotin-lys-tRNA that results in a protein containing lysine residues modified with biotin. The biotinylated proteins produced in this way are then captured on to a solid phase using an avidin or streptavidin coated solid phase. Alternative methods for capture of the proteins produced include non-specific or passive adsorption, and via the binding to specific binding partners other than those for the modified amino acids introduced by the addition of modified tRNA (e.g., binding partners of affinity tags present in the expressed protein). Alternatively the proteins produced may be generated without the use of the modified tRNA and captured using alternative methods for capture, including non-specific or passive adsorption, and via the binding to specific binding partners for the produced proteins (e.g., binding partners of affinity tags present in the expressed proteins).

In this embodiment of the invention solid phase bound protein products of an in vitro transcription and translation reaction are produced. In the preferred embodiment these step are all carried out in a multiwell plate with 20 wells or more, or ideally 40 wells or more, or most ideally 84 wells or more that allows for the rapid and efficient analysis of the immobilized proteins. For example, a plurality of proteins (preferably greater than 80, more preferably greater than 1000, more preferably greater than 10,000 and most preferably greater than 20,000) are produced in parallel and immobilized in separate wells of one or more multi-well plates (e.g., 24, 96, 384 or 1536 well plates). In a most preferred embodiment of the invention the protein products of the in vitro transcription and translation reaction are immobilized on to one of the following in a multi-well format: carbon containing surfaces or magnetic beads. In an alternative preferred embodiment of the invention the protein products of the in vitro transcription and translation reaction are immobilized on to one of the plates described in more detail in copending Provisional Application No. 60/301,932 (entitled "Assay Plates, Reader Systems and Methods for Luminescence Test Measurements", filed on Jun. 29, 2001, and U.S. application Ser. Nos. 10/185,274 and 10/185,363, filed Jun. 28, 2002, each hereby incorporated by reference, and particularly in the description of Plate Type B, Type C, Type D, and Type E in Example 6.1. Immobilization in these multi-well plates may be advantageous, even in applications that do not involve ECL measurements, do to the excellent adsorption properties and high binding capacity of the carbon-containing electrode surfaces.

In certain embodiments of the invention, a protein expressed by the expression methods of the invention is characterized by its ability to bind to a potential binding partner (e.g., a biologically relevant binding partner or a binding reagent that specifically binds a structural characteristic such as an epitope or post-translational modification). In one embodiment, the binding event is measured using technique that does not require a detectable label (e.g., surface plasmon resonance, agglutination). In another embodiment, the binding event is measured using a technique the measures a change in a property of labels linked to the protein and/or potential binding partner (e.g., techniques that measure changes in fluorescence polarization, lifetime or energy transfer). In a preferred embodiment, one of the protein or potential binding partner is immobilized on a solid phase support so that the binding event may be measured by measuring the accumulation of the other member of the binding pair on the solid phase. Most preferably, this measurement is accomplished via a detectable label attached to the other member of the binding pair. In such assay methods, the number of binding interactions is correlated to the accumulation of labels on the solid phase; this accumulation of labels being measurable by a variety of techniques (e.g., fluorescence for fluorescence labels, enzyme activity for enzyme labels, ECL for ECL labels, etc.). Most preferably, the solid phase is an electrode material, the labels are ECL labels and the accumulation of labels is measured via an ECL measurement.

In certain other embodiments of the invention, a protein expressed by the expression methods of the invention is characterized by its catalytic activity or its ability to act as a substrate in the presence of a catalytic activity or other chemical activity. Where such activity is characterized as a joining (i.e., an activity that joins two or more species, e.g., nucleic acid ligase activity, nucleic acid polymerase activity, protein translation activity, ubiquitin ligase activity, etc.) and/or cleaving activity (i.e., an activity that results in the cleaving of a species into two or more components, e.g., protease activity, nuclease activity, glycosidase activity, etc.), the activity can be measured using techniques analogous to those described for binding reactions. By way of example, an activity that joins a first substrate having a first label with a second substrate is measured by immobilizing the second substrate on a solid phase support (e.g., by passive adsorption or by capture via the specific binding of the second substrate or a second label on the second substrate to a binding reagent on the solid phase support) and measuring the amount of the first label on the solid phase. In another example, a cleaving activity is measured by using a substrate having a first label that is immobilized on a solid phase support (e.g., by passive adsorption or by capture via the specific binding of a second label on the substrate to a binding reagent on the solid phase support) and measuring the loss of labels from the solid phase in the presence of the activity.

In certain other embodiments of the invention, an activity is measured by using a substrate that exhibits a detectable change in a chemical or physical property when acted on by the activity of interest (e.g., luminescence, color, ability to act as an ELC coreactant, etc.).

Assays for Post-Translational Modifications

In one embodiment of the invention, a nucleic acid construct is preferably obtained with the genes of interest located within the construct such that the gene of interest can be transcribed into RNA that can direct the synthesis of the protein encoded by the genes of interest. The nucleic acid construct is then subjected to an in vitro transcription reaction and followed by an in vitro translation reaction. These two reactions can also be combined in a single in vitro reaction.

The protein product (or, alternatively, protein obtained by any other method) is than analyzed for the presence of post-translational modifications of interest. Preferably, a plurality of constructs comprising different genes are prepared and the protein products of these genes produced and analyzed, most preferably in parallel in the wells of multi-well plates.

Preferably, during the translation reaction the protein produced is also labeled, most preferably by using a modified tRNA that directs the incorporation of a modified amino acid during this step. On completion of this protein expression step the reaction mix is then subjected to assays for protein function, and or activity and or structure. For example the protein in the mix is captured on to a solid phase using a binding protein specific for the label introduced during the translation reaction. A good example of how this is achieved is by the use of the biotin-lys-tRNA that results in a protein containing lysine residues modified with biotin. The biotinylated proteins produced in this way are then captured on to a solid phase using an avidin coated solid phase. Examples of the solid phase include beads, particles, colloids, single surfaces, tubes, multiwell plates, microtitre plates, slides, membranes, gels and electrodes, The preferred plates are described in more detail in copending Provisional Application No. 60/301,932 (entitled “Assay Plates, Reader Systems and Methods for Luminescence Test Measurements”, filed on Jun. 29, 2001, hereby incorporated by reference) and particularly in the description of Plate Type B, Type C, Type D, and Type E in Example 6.1 and U.S. application Ser. Nos. 10/185,274 and 10/185,363, filed Jun. 28, 2002, each hereby incorporated by reference.

With these proteins immobilized on to a solid phase the proteins are then available for an assay to determine if they have been subject to any structural modifications or post-translational modifications. These post-translational modifications are then detected using a labeled binding species specific for the post-translational modification that binds to the immobilized proteins containing these post-translational modifications. An example of how this is achieved is illustrated by phosphorylation of tyrosines. This post-translational modification is carried out by protein kinases and this is readily detected using antibodies specific to phosphotyrosine. In this example the antibody would be labeled with a detectable label and the bound signal detected to determine the amount phosphorylation for a given protein form the translation reaction. An example of such a reagent is Abzyme (IGEN International, Inc., Gaithersburg Md.) that is an antibody to phosphotyrosine labeled with an electrochemiluminescent (ECL) label. In the case of other post-translational modifications, examples of post-translational modifications that can be detected with antibodies include ubiquitinylation, SUMO, other phosphorylated sequences, acetylation, prenylation, farnesylation, and geranylation.

In a further embodiment of the invention based on the example above a labeled substrate for a given post-translation modification is included in the translation reaction. Examples of such substrates include ubiquitin, SUMO-1, Nedd8 or Agp12 or homologous substrates. Examples of labels that could be used include, metal chelates, biotin, binding species, digoxigenin, enzymes, fluorophores, luminescent species and ECL labels. In a preferred embodiment of a labeled substrate, ubiquitin is labeled with an ECL label.

The result of the inclusion of a labeled substrate for a given post-translational reaction is that those proteins that are subjected to this post-translational modification are produced with the post-translational modification including the label. This results in the production of a labeled protein. Proteins that are labeled in this way through the action of a post-translational modification and are also labeled as described using modified tRNA contain two, preferably different, labels. Thus these proteins are readily detected by immobilization through one of the labels and detected with the other. In a preferred embodiment the protein is modified with a biotin during translation with biotin-Lys-tRNA and subjected to post-translational modification using ECL labeled ubiquitin.

In an alternative embodiment the invention involves either obtaining clones or the production of clones in a desired cloning vector or nucleic acid construct. The DNA from these is then subjected to an in vitro transcription reaction and followed by an in vitro translation reaction. These two reactions can also be combined in a single in vitro reaction. During the translation reaction the protein produced is also labeled using a modified tRNA that directs the incorporation of a modified amino acid during this step. On completion of this protein expression step the reaction mix is then subjected to assays for post-translational modification. The protein in the mix is then captured on to a solid phase using a binding protein specific for the post-translational modification. A good example of how this is achieved is by the use of an antibody specific for a post-translational modification for example an antibody to ubiquitin immobilized on to a solid phase. This allows the capture of proteins that have been ubiquitinated on to the solid phase. Examples of the solid phase include beads, particles, colloids, single surfaces, tubes, multiwell plates, microtitre plates, slides, membranes, gels and electrodes. With these proteins immobilized on to a solid phase the proteins are then available for an assay to determine if they have been captured and thus subject to any structural modifications or post-translational modifications. These proteins are then detected using a binding species specific for the modified amino acid that has an attached label. A good example of how this is achieved is by the use of the biotin-lys-tRNA in the translation reaction resulting in a protein containing lysine residues modified with biotin. The biotinylated proteins that result and are then captured through the post-translational modification binding species and are subsequently detected using streptavidin (also including avidin or anti-biotin antibodies) labeled with a detectable label. In the case of other post-translational modifications antibodies are available to ubiquitinylation, SUMO, other phosphorylated sequences, acetylation, which would readily allow the capture of the proteins produced in an in vitro translation reaction that are subjected to these post-translational modifications.

Assays for Enzyme Activity.

In another embodiment of the invention clones are either preferably produced or obtained in the desired vectors or nucleic acid constructs. The constructs are then subjected to an in vitro transcription reaction and followed by an in vitro translation reaction. These two reactions can also be combined in a single in vitro reaction. The protein product, or alternatively a protein obtained by other means, is then incubated under conditions conducive to the activity of interest (pH, temp, presence of cofactors, substrates, energy sources, etc.) analyzed for the presence of the activity. Preferably, a plurality of constructs comprising different genes are prepared and the protein products of these genes produced and analyzed, most preferably in parallel in the wells of multi-well plates. Such screens can be used, for example, to identify proteins with a specific category of activity (e.g., all tyrosine kinases) or to elucidate biochemical pathways by identifying the enzyme responsible for a reaction of a known substrate. In one example, a panel of proteins is screened against a panel of substrates (the substrates, preferably, being immobilized as an array) to identify previously unknown enzyme/substrate pairs. Most preferably, the substrate array is immobilized within the wells of a multi-well plate so that a large number of proteins can be quickly screened in parallel.

Preferably, during the translation reaction the protein produced is also labeled, preferably by using a modified tRNA that directs the incorporation of a modified amino acid during this step. In one case for example the protein in the mix is captured on to a solid phase using a binding protein specific for the label introduced during the translation reaction. A good example of how this is achieved is by the use of the biotin-lys-tRNA that results in a protein containing lysine residues modified with biotin. The biotinylated proteins produced in this way are then captured on to a solid phase using a streptavidin coated solid phase. It is also possible to use other binding species specific for biotin including avidin and anti-biotin antibodies.

The immobilized proteins are, optionally purified of other components of the translation system (e.g., by washing the solid phase) and are then analyzed for their enzyme activity. This is typically determined by the addition of the desired substrate for the activity of interest. The substrate is then acted on by the immobilized enzyme activity produced by the transcription and translation reactions to produce the product of the enzyme activity of interest. The activity of the enzyme is then determined by the detection and or quantitation of the product of the reaction. Optionally the loss of the substrate may also be determined. The measurements are, preferably, carried out as described above by i) measuring a detectable change in a property of a substrate on reaction of the substrate to form product; ii) measuring the binding activity of a substrate or product for binding reagents specific for one of the product and substrate or iii) through a measurement of joining or cleaving activity.

Optionally, the protein is treated with a post-translational modification activity prior to conducting the enzymatic assay so as to uncover a nascent activity.

Examples of preferred enzyme activities that may be detected include kinases, hydrolases, protease, polymerases, glycosidases, and phosphatases. Other preferred enzyme activities that can be measured include the activities of enzymes that catalyze the post-translational modification of proteins, e.g., signal peptide cleavage, phosphorylation, acetylation, adenylation, proteolysis, amino peptidase clipping, arginylation, disulphide bond formation and cleavage, amidation, glycosylation, isoprenylation, myristoylation, ubiquitination, SUMOlation, Agp12 ligation, Nedd8 ligation and covalent addition of proteins. Examples of enzyme activities which may be measured include cleaving or joining enzymes such as amidases, proteases, peptidases, glycosidases, saccharases, glycopeptidases, nucleases (including ribonucleases and deoxyribonucleases), endonucleases (including restriction endonucleases), exonucleases, ribosomes, ribosomal RNA, ribozymes, self-splicing molecules such as introns or inteins, esterases, phosphodiesterases, phosphorylases, AP endonucleases, polymerases (e.g., DNA or RNA polymerases), nucleic acid repair proteins, amino peptidases, carboxy peptidases, aminoacyl-tRNA synthetases, ADP-ribosyl transferases, proteases of the complement pathway, proteases of the thrombolytic pathways, transferases, endoglycosidases, exoglycosidases, lipases, endoproteinases, glutathione S-transferases, polysaccharide or oligosaccharide synthases (e.g. glycosyl transferases or glycogen synthases), ligases, ubiquitin-protein ligases, trans-glutaminases, integrases, and DNA glycosylases (e.g., uracil-DNA glycosylases), helicases, etc.

Examples of substrates that may be used for kinases include, poly (Glu-Tyr), peptides, proteins, and proteins produced by a process of transcription and translation. In a preferred example, the substrate is a generic substrate that is broadly targeted acted on by a genus of enzymes (by way of example, applicants have found that poly (Glu-Tyr) can be used as a generic substrate in screens for tyrosine kinases. The product of the action of a tyrosine kinase on the poly (Glu-Tyr) is to generate poly (glu-Tyr) containing phosphorylated tyrosines which is readily detected in a sandwich binding assay format using an antibody to phosphotyrosine immobilized on to a solid phase and labeled anti phosphotyrosine antibody such as Abzyme (IGEN International, Inc., Gaithersburg Md.). In a further embodiment the proteins produced in the translation reaction may also be subjected to the action of a post-translational modification prior to determination of its enzyme activity. Examples of this include the phosphorylation of a protein from the translation reaction prior to its assay for kinase activity. Thus, the methods of the invention may be used for identifying post-translational modifications that regulate enzymatic activity.

According to one preferred embodiment, the invention is directed to the identification of proteins with self-modifying activities. A protein expressed according to the methods of the invention (and, preferably, immobilized as described above) is incubated under conditions conducive to the activity of interest. The same protein is then assayed for the presence of a self-modification of interest (e.g., via its binding activity for a binding reagent specific for the modification of interest or via the cleavage or joining of a labeled component from or to the protein. Most preferably, the protein is immobilized on a solid phase (as described above) and the extent of modification assays measured according to the solid phase assay techniques described above.

According to one preferred embodiment, the invention is directed to efficient methods for screening proteins for their ability to modify both themselves and other species. Both these activities may be biologically relevant (particularly for receptor kinases) and also provide complementary indicators of a proteins function. By way of example, one embodiment of this class of methods will be illustrated through assays for the identification of the in vitro kinase activity and autophosphorylation activity of proteins.

According to this embodiment of the proteins are immobilized onto a surface of a solid phase such as the surfaces in wells of multi-well plates (according, e.g., to the immobilization methods described above). The proteins are incubated under conditions appropriate for a modifying activity of interest (e.g., kinase activity) in the presence of a substrate for the activity of interest (preferably, a generic substrate such as poly(glu, tyr) in the case of tyrosine kinase activity). The presence of self-modified proteins on the solid phase is measured using the solid phase assay techniques of the invention (e.g., via the use of labeled anti-phosphotyrosine antibodies for measuring auto-phosporylation). The presence of modified substrate is also measured via the assay techniques of the invention (e.g., by carrying out a sandwich immunoassay for phosphorylated poly(glu, tyr).

The measurement of the modified substrate can be carried out in a separate assay compartment (e.g., by transferring the kinase reaction supernatants to another multi-well plate. Alternatively, both measurements can be carried out in the same well by including in the well two discreet assay domains: an assay domain for immobilizing the test protein (e.g. an assay domain having an immobilized capture reagent, such as avidin, for capturing a test protein comprising a binding species such as biotin) and a discreet assay domain having appropriate reagents for measuring the modified substrate (e.g., an assay domain comprising an antibody specific for the modified substrate such as an anti-phosphotyrosine antibody. The invention also provides for an in vitro assay to screen for candidate substances, e.g., small molecules, proteins, nucleic acids, lipids, etc. that are effective at inhibiting or activating the kinase activity (against self and/or other substrates) of the identified kinases.

The invention includes in vitro assays for the autophosphorylating activity and/or substrate phosphorylating activity for potential kinases selected from the list of kinases below. Preferably, the auto-phosphorylation assays are conducted using kinases that are expressed and immobilized as described above. Preferably, the substrate phosphorylation assays employ poly(glu, tyr) as a generic substrate.

The list of potential kinases includes the kinases listed below. Preferred kinases for use with the assays of the invention are Ephb3, Ephb4 and Fgfr4.

| IMAGE# | Locus | Kinase |
|---|---|---|
| 2644960 | Kit | kit oncogene |
| 2654352 | Fgfr2 | fibroblast growth factor receptor 2 |
| 3482498 | Tek | endothelial-specific receptor tyrosine kinase |
| 3601246 | FRK | B-cell src-homology tyrosine kinase |
| 3673003 | Ephb3 | Eph receptor B3 |
| 3866791 | JAK1 | Janus kinase 1 (a protein tyrosine kinase) |
| 3896359 | FGFR1 | fibroblast growth factor receptor 1 (fms-related TK2) |
| 3921724 | FGR | FYN oncogene related to SRC |
| 3978518 | Hck | hemopoietic cell kinase |
| 3982920 | Clk4 | CDC like kinase 4 |
| 3989782 | Yes | Yamaguchi sarcoma viral (v-yes) oncogene homolog |
| 3995512 | CLK2 | CDC-like kinase 2 |
| 4013934 | Ephb4 | Eph receptor B4 |
| 4036253 | CLK3 | CDC-like kinase 3 |
| 4037899 | FGFR1 | fibroblast growth factor receptor 1 |
| 4238984 | Kdr | kinase insert domain protein receptor |
| 4239139 | Fgfr4 | fibroblast growth factor receptor 4 |
| 4343428 | PTK2B | protein tyrosine kinase 2 beta |
| 4384416 | BTK | Bruton agammaglobulinemia tyrosine kinase |
| 4387232 | CLK1 | CDC-like kinase 1 |
| 4419700 | LCK | lymphocyte-specific protein tyrosine kinase |
| 4419973 | FGR | GR feline sarcoma viral (v-fgr) oncogene homolog |
| 4471986 | ALK | anaplastic lymphoma kinase (Ki-1) |
| 4485050 | Fert2 | fer (fms/fps related) protein kinase |
| 4498209 | EPHB1 | EphB1 |
| 4515877 | Frk | fyn-related kinase |
| 4537393 | TTK | TTK protein kinase |
| 3673003 | Ephb3 | Eph receptor B3 |
| 4013934 | Ephb4 | Eph receptor B4 |
| 4239139 | Fgfr4 | fibroblast growth factor receptor 4 |

Assays for Substrate Activity.

In an alternative embodiment of the invention clones are preferably either produced or obtained in the desired vectors or nucleic acid constructs. The DNA from these is then subjected to an in vitro transcription reaction and followed by an in vitro translation reaction. These two reactions can also be combined in a single in vitro reaction. The protein product, or alternatively a protein obtained by other means, is then incubated in the presence of a modifying activity, e.g., an enzymatic activity, under conditions conducive to the activity (pH, temp, presence of cofactors, substrates, energy sources, etc.) and analyzed for the presence of modifications derived from the activity. Preferably, a plurality of constructs comprising different genes are prepared and the protein products of these genes produced and analyzed, most preferably in parallel in the wells of multi-well plates. In one embodiment, each protein is immobilized in a separate well of a multi-well plate. In an alternative embodiment, a plurality of proteins are immobilized in an array in a well of a multi-well plate (or on a protein "chip") so that a panel of activities (preferably, one per well or chip) can be screened in parallel against a panel of potential substrates (preferably, a plurality per well or chip).

Preferably, during the translation reaction the protein produced is also labeled, preferably by using a modified tRNA that directs the incorporation of a modified amino acid during this step. On completion of this protein expression step the reaction mix is then subjected to assays to determine if it is a substrate for an enzyme. In one embodiment the protein in the mix is captured on to a solid phase using a binding protein specific for the label introduced during the translation reaction. A good example of how this is achieved is by the use of the biotin-lys-tRNA that results in a protein containing lysine residues modified with biotin. The biotinylated proteins produced in this way are then captured on to a solid phase using an avidin coated solid phase.

The immobilized are, optionally, purified of other components of the translation system (e.g., by washing the solid phase) and then analyzed for their substrate activity. In order to determine if a specific protein is substrate for a given enzyme activity the immobilized proteins are contacted with an enzyme followed by an assay to detect the modifications of the immobilized proteins by the enzyme activity (e.g., by contacting the protein with a, preferably labeled, binding reagent that is specific for the modification or, in the case of a joining activity, via the use of a labeled co-substrate that is joined to the protein as a result of the activity). In one example, an assay for protease substrates involves the use of specific binding reagents or antibodies that recognize the protein as altered by the protease. This readily allows the detection of the action of the enzyme and determination of a substrate for the enzyme. In another example, a protein kinase is contacted with the immobilized proteins from the translation reaction and the resulting phosphorylation detected using a specific antibody for said phosphorylation as described above for post-translational modifications. In a further example a ubiquitination enzyme, or enzyme mixture is contacted with the immobilized proteins from the translation reaction and the resulting ubiquitination detected using a specific antibody for said ubiquitination. In the case of ubiquitination an alternative approach would be to make use of ubiquitin labeled with a detectable species such as an ECL label.

In a further extension of this methodology, the proteins that are produced in the translation reaction may be assayed for substrate activity prior to immobilization and detection.

Optionally, the proteins produced in the translation reaction may be subjected, prior to exposure to the test activity, to a pretreatment step that removes post-translational modifications introduced in the translation step (in particular, modifications of the type introduced by the test activity). By way of example, phosphates on a test protein that were introduced during protein translation may interfere with an assay for kinase activity. Examples of such a pretreatment steps include phosphatase treatment, deubiquitination, defamesylation, de-geranylation, de-glycosylation.

In a further embodiment the proteins produced in the translation reaction may also be subjected, prior to the determination of its substrate activity, to the action of a post-translational modification activity. This embodiment enables the screening of specific modifications on substrate activity. Examples of this approach include the phosphorylation of a protein from the translation reaction prior to its assay for ubiquitination.

Assays for Binding Activities of Proteins.

In an alternative embodiment of the invention clones are preferably either obtained or produced in a desired cloning vector or nucleic acid construct. The DNA from these is then subjected to an in vitro transcription reaction and followed by an in vitro translation reaction. These two reactions can also be combined in a single in vitro reaction. The protein product, or alternatively a protein obtained by other means, is then incubated in the presence of a potential binding partner and analyzed for formation of a binding complex. Preferably, a plurality of constructs comprising different genes are prepared and the protein products of these genes produced and analyzed, most preferably in parallel in the wells of multi-well plates. In one embodiment, each protein is immobilized in a separate well of a multi-well plate. In an alternative embodiment, the potential binding partner may be immobilized and the test protein is introduced in solution. In another embodiment, a plurality of proteins are immobilized in an array in a well of a multi-well plate (or on a protein "chip") so that a panel of potential binding partners (preferably, one per well or chip) can be screened in parallel against a panel of proteins (preferably, a plurality per well or chip). Alternatively, the potential binding partners are the species immobilized in the array and the test proteins are introduced into individual wells.

Preferably, during the translation reaction the protein produced is also labeled, preferably by using a modified tRNA that directs the incorporation of a modified amino acid during this step. On completion of this protein expression step the reaction mix is then subjected to assays for protein binding activity. In one case, for example the protein in the mix is captured on to a solid phase using a binding protein specific for the label introduced during the translation reaction. A good example of how this is achieved is by the use of the biotin-lys-tRNA that results in a biotinylated protein containing lysine residues modified with biotin. The biotinylated proteins produced in this way are then captured on to a solid phase using an avidin, or streptavidin coated solid phase. Optionally, the proteins may be treated with a post-translational modifying activity prior to analysis so as to uncover a nascent binding activity.

With these proteins immobilized on to a solid phase, the proteins are then available for an assay to determine the protein's binding activities. These binding activities are determined by measuring the binding of the protein to a binding partner that is, preferably, labeled. Preferably, the binding partner is added to the proteins captured on to the solid phase and incubated to allow binding. Following this step the degree of binding is determined based on a determination of the amount of binding partner captured on to the solid phase, e.g. via measurement of a label on the binding partner.

In an alternative embodiment, the potential binding partner is immobilized on a solid phase support and the potential binding partner is contacted with a labeled test protein generated from a translation reaction. The formation of binding complexes is determined by measuring the amount of labeled test protein on the solid phase.

Preferred potential binding partners include proteins, peptides (e.g., recognition sequences from a protein), lipids, phosphoinositides, nucleic acids, hormones (including steroids), drugs, etc. In a preferred embodiment, the potential binding partner is a peptide that has a modification that is the same as a post-translational modification. By way of example, a potential binding partner may be a short phosphorylated peptide, preferably a putative recognition sequence from a known protein, e.g., the following recognition site from IkBa (H2N-LKKERLLDDRHD(p)SGLD (p)SMKDEEYC-COOH) (SEQ ID NO: 1). The binding assays of the invention may be used to identify proteins that bind to this recognition sequence.

Potential binding partners for use in the binding assays of the invention are, preferably, labeled with a detectable label. The label may be used to detect the occurrence of a binding interaction, in particular, when the translated test protein is immobilized on a solid phase. Alternatively, when the potential binding partner is immobilized on a solid phase, the label may be used to capture the potential binding partner on a solid phase via the interaction of the label with a capture reagent that binds the label. Peptidic potential binding partners are, preferably, labeled at a Cys residue, e.g., the IkBa peptide (SEQ ID NO: 1) described above is preferably labeled at the C-terminal Cys residue with a label such as the ECL label ORI-TAG maleimide.

Other methods for immobilizing a potential binding partner onto a solid phase include conventional immobilization methods such as passive adsorption, covalent linkage to a chemically activated surface including NHS ester, epoxide, maleimide chemistries and cross-linking reagents. Useful cross-linking reagents include cross-linking reagents that comprise one or more functional groups capable of reacting with components of a lipid/protein layer or an electrode surface (e.g., imidoesters, active esters such as NHS esters, maleimides, a-halocarbonyls, disulfides such as pyridyldithiols, carbodiimides, arylazides, amines, thiols, carboxylates, hydrazides, aldehydes or ketones, active carbamates, glyoxals, etc.). In some applications it may be advantageous to use photo-reactive cross-linkers (such as arylazides) so as to better control the cross-linking process. Exemplary cross-linking agents include homo- and hetero-bifunctional cross-linking agents such as those sold by Pierce Chemical Co. and/or described in the 1994 Pierce Catalog and Handbook (Pierce Chemical Co., Rockford, Ill., 1994), the chapters relating to cross-linking agents hereby incorporated by reference.

In the case of small molecules or peptides these can be directly immobilized using the chemically activated surfaces as described previously. In an alternative method the small molecules are first coupled using typical chemistries such as NHS ester, epoxide, cross-linking chemistries (see above), maleimide to a carrier typically a large molecule such as a protein that can then be immobilized using a simple passive adsorption methods. An example of this is the coupling of Cys or SH containing peptides to maleimide activated BSA. These Peptide:BSA conjugates can then be immobilized readily using passive adsorption methods. In another alternative the small molecules are first coupled to a another binding species such as biotin or fluorescein, these conjugates are then immobilized using a binding species:binding partner interaction such as biotin:streptavidin, biotin:avidin, biotin:antibiotin, fluorescein:anti-fluorescein. Examples of such small molecule conjugates include thyroxine-biotin and triiodothyronine-biotin (Roche Diagnostics, Indianapolis, Ind.), biotinylated-phosphoinositides (Rao, V R., J. Biol Chem. 1999, 274, 37893).

Assays for Protein:Protein Binding Interactions.

In another embodiment of the invention clones are preferably either obtained or produced in a desired cloning vector or nucleic acid construct. The DNA from these is then subjected to an in vitro transcription reaction followed by an in vitro translation reaction to produce a first library of translated proteins. The transcription and translation reactions can be combined.

Preferably, proteins are labeled with a first label during the translation reaction, preferably by introducing a modified tRNA that directs the incorporation of a modified amino acid. The process is repeated to produce a second library of translated proteins comprising a second label, e.g., by using a different modified tRNA species having a different modified tRNA. For example, biotin-lys-tRNA is used for one translation and BODIPY®FL-lys-tRNA for the other. Proteins from the first library are mixed with proteins from the second library and the formation of binding complexes is measured to identify pairs of proteins that have binding affinity for each other. The translation reactions and/or binding assays are preferably carried out in parallel in a multi-well plate format.

Preferably, protein:protein interactions are detected in the following way. Two translation products from the two different libraries are mixed together to form a mixture of the two differently labeled translation products. These are allowed to bind and the resulting mixture is then captured on to a solid phase using a binding species specific for one of the labels in the products of the translation (alternatively, one of the translation products is first captured and is then contacted with the other translation product). Following this (or sequentially) a labeled or detectable binding species is added which recognizes the label not used to immobilize the product of the translation reaction (alternatively, this label is a directly detectable label and is detected directly). In this way the interaction between the proteins produced in the two translation reactions is detected. An example of this is where a gene is transcribed and translated in the presence of BODIPY®FL-lys-tRNA and a gene is transcribed and translated in the presence of biotin-lys-tRNA. These reactions result in the production of proteins that are labeled with BODIPY®FL and biotin respectively. These two-labeled proteins in the translation mix are mixed and allowed to interact. These proteins are then captured on to a solid phase using for example streptavidin followed by detection of the BODIPY®FL to allow the determination of protein:protein binding. Another example of this is where a gene is transcribed and translated in the presence of $Ru(bpy)_3^{2+}$-lys-tRNA and a gene is transcribed and translated in the presence of biotin-lys-tRNA. These reactions result in the production of proteins that are labeled with $Ru(bpy)_3^{2+}$ and biotin respectively. These two labeled proteins in the translation mix are mixed and allowed to interact. These proteins are then captured on to a solid phase using for example streptavidin followed by detection of the $Ru(bpy)_3^{2+}$ to allow the determination of protein:protein binding.

Assays for Nucleic Acid Sequence Binding Activity.

In an one embodiment of the invention clones are preferably either obtained or produced in a desired cloning vector or nucleic acid construct. The DNA from these is then subjected to an in vitro transcription reaction and followed by an in vitro translation reaction. These two reactions can also be combined in a single in vitro reaction. During the translation reaction, the protein produced is also labeled using a modified tRNA that directs the incorporation of a modified amino acid during this step. On completion of this protein expression step the reaction mix, or alternatively a reaction mix obtained by other means, is then subjected to assays for nucleic acid sequence binding activity. In one case for example the protein in the mix is captured on to a solid phase using a binding protein specific for the modification introduced by the modified tRNA during the translation reaction. A good example of how this is achieved is by the use of the biotin-lys-tRNA that results in a biotinylated protein containing lysine residues modified with biotin. The biotinylated proteins produced in this way are then captured on to a solid phase using an avidin coated solid phase.

With these proteins immobilized on to a solid phase the proteins are then available for an assay to determine the proteins nucleic acid sequence binding activities. These nucleic acid sequence binding activities are determined using various methods including using a labeled nucleic acid sequence. Typically the nucleic acid sequence is added to the proteins captured on to the solid phase and incubated to allow binding. Following this step the degree of binding is determined based on a determination of the amount of label captured on to the solid phase. In a preferred embodiment the nucleic acid sequence is a DNA sequence that has been labeled with an ECL label during synthesis using ORI-TAG® labelled phosphoramidite (IGEN International, Inc., Gaithersburg, Md.). In an alternative protocol the labeled nucleic acid is added to the translation reaction prior to immobilization of the translation product on to a solid phase.

In an alternative embodiment of the invention clones are either obtained or produced in a desired cloning vector or nucleic acid construct. The DNA from these is then subjected to an in vitro transcription reaction and followed by an in vitro translation reaction. These two reactions can also be combined in a single in vitro reaction. During the translation reaction the protein produced is also labeled using a modified tRNA that directs the incorporation of a modified amino acid during this step. On completion of this protein expression step the reaction mix is then subjected to assays for nucleic acid sequence binding activity. In this embodiment the binding activity of the protein from the transcription translation system is analyzed by determining its binding to an immobilized nucleic acid sequence. For example a potential nucleic acid sequence is immobilized on to a solid phase using methods known in the art such as passive adsorption, covalent linkage to a chemically activate surface including NHS ester, epoxide, cross-linking reagents (see above), maleimide chemistries. In an alternative method the nucleic acid sequence are first coupled using typical chemistries such as NHS ester, epoxide, maleimide to a carrier typically a large molecule that can then be immobilized using a simple passive adsorption methods. This method also allows for the construction of arrays of multiple nucleic acid sequences within a single container. Also the labeling of the nucleic acid either during synthesis or post synthesis with a small molecule binding species such as biotin, fluorescein, digoxigenin also allows for the immobilization of the nucleic acid on to a solid phase in specific arrays using an immobilized binding partner. With the nucleic acid sequence immobilized on to the solid phase the labeled proteins that have been produced in the transcription and translation reaction are contacted with this coated solid phase. The binding activity of the proteins from the transcription and translation reactions is determined based on the detection of the modified amino acid incorporated during the translation reaction. Typically this is achieved using labeled; avidin, streptavidin or an antibody specific for the modification on the modified amino acid.

Assay for Antigens.

An alternative embodiment of the invention is directed to the discovery of antigens recognized by antibodies. These antibodies may be monoclonal or polyclonal or patient samples, i.e., serum or plasma. These patients may be animal or human and may or may not have been diagnosed with a disease or medical condition. Examples of patient who have been diagnosed with a disease or medical condition include auto-immune disease, immunological disorders, asthma, heart disease, MS, atherosclerosis and cancer. Screens for antigens have been made typically using bacterial expression methods; this invention includes novel methods for screening for antigens using proteins (preferably, labeled) produced in a transcription and translation reaction. The proteins are contacted with the antibodies and the formation of binding complexes is measured. Preferably, the binding measurements are carried out in a solid phase format and involve the capture of the translated proteins and detection of the antibody or, alternatively, capture of the antibody and detection of the translated proteins. The antibodies and/or proteins are, preferably, labeled and captured and/or detected via these labels. Alternatively, the antibodies are captured or detected using antibody-specific binding reagents such Proteins A, G or L or secondary antibodies. In one example, translated proteins are immobilized on to a solid phase followed by detection of those binding to the added antibodies using either directly labeled antibodies or via a labeled binding species specific for the added antibody. In the preferred embodiment the proteins produced in the transcription and translation reaction (nucleic acid constructs such as a cDNA library or a collection of clones expected to contain the antigens specific for the antibodies of interest) are immobilized on to a solid phase in a multiwell plate as described above. The proteins are contacted with the antibodies and the formation of binding complexes is detected. Each protein may be analyzed in individual wells of a multi-well plate. Alternatively, an array of proteins is produced in a well of a multi-well plate or on a protein chip and a plurality of binding assays are carried out in one reaction volume. In the most preferred embodiment the proteins produced in the translation are labeled using a modified precharged tRNA such as biotin-lys-tRNA as described earlier. These labeled proteins are then immobilized by binding to avidin or streptavidin immobilized on to a carbon containing surface or magnetic beads. These immobilized proteins are thus available for binding to the antibodies to allow the detection and determination of the genes and proteins of the antigens recognized by the antibodies. The antibodies bound to the immobilized antigen are detected using for example ECL labeled anti antibodies (IGEN International, Inc., Gaithersburg, Md.).

Recruitment Assays.

As described above, certain embodiments of the invention preferably involve expression of a protein using a cell-free translation system, immobilization of the protein (preferably, via a label introduced into the protein during the translation reaction) and assaying the immobilized protein for an activity (e.g., a catalytic activity, a substrate activity, a binding activity, etc.). Surprisingly, applicants have found occasional translated proteins that appear unlikely to have an activity of interest (on the basis, e.g., of sequence, structure or historical data) but that test strongly positive for the activity. Applicants have discovered that, in many cases, this apparent contradiction is due to the recruitment of active components of the translation reaction mixture to the solid phase via binding of the active component to the translated protein.

By way of the example, applicants have screened immobilized proteins for kinase activity and found proteins that test positive but do not appear to have inherent kinase activity. In one specific example, a biotin-labeled protein was produced by transcription/translation in a rabbit reticulocyte system that was supplemented with tRNA that was charged with biotin-lys, the protein was immobilized on a streptavidin-coated surface and the immobilized protein was assayed for kinase activity by measuring its ability to phosphorylate poly(Glu, Tyr). The mechanism of this effect has been shown to be the recruitment of endogenous kinases in rabbit reticulocyte lysate through binding to the biotin-labeled protein; the observed activity can be significantly reduced or eliminated through the use of high stringency washes designed to dissociate the binding interaction responsible for the recruitment.

In one embodiment of the invention, a translated protein, or alternatively a protein obtained by other means, is immobilized, the protein is not washed or washed with a low stringency wash, and the protein is assayed for an activity of interest or for its ability to recruit a species having an activity of interest. In another embodiment, a translated protein is immobilized, the protein is washed with a high stringency wash, and the protein is assayed for an activity of interest in the absence of recruited species. By comparison of the results of these two experiments, positive results can be categorized as resulting from inherent activity or recruitment. In another embodiment of the invention, a translated protein is i) immobilized, ii) the protein is not washed or washed with a low stringency wash, iii) the protein is assayed for an activity of interest or its ability to recruit a species having an activity of interest (e.g., by introduction of a substrate for an enzymatic activity), iv) the protein is washed in a high stringency wash and v) the protein is assayed for the activity of interest in the absence of recruited species. Thus, it is possible to analyze both conditions using one set of immobilized proteins.

Preferably, the high stringency wash is a high salt buffer, preferably, having an salt concentration of greater than or equal 750 mM, or more preferably 1 M. Alternatively, high stringency may be accomplished through non-physiological pH (preferably >8.5 or <6) or the introduction of denaturing detergents or chaotropic agents. The label used in the translation reaction is preferably chosen for its ability to participate in binding reaction that is relatively insensitive to high stringency conditions (e.g., biotin-avidin or biotin-streptavidin).

The identity of recruited species may be identified through a variety of analytical techniques including sequencing, mass spectrometry, capillary electrophoresis, HPLC, electrophoresis, western blotting, antibody arrays, or a combination thereof.

Alternative Approaches.

In a further embodiment of the invention the in vitro transcription and translation reaction can be carried out in the presence of a membrane preparation (e.g., microsomes) that allows for the signal peptide processing, insertion into membranes and glycosylation of the proteins produced by the in vitro translation reaction. Examples of membrane preparations that can be used include canine microsomal membranes (Walter, P. and Blobel, G. (1983) Meth. Enzymol. 96, 84), *Xenopus* egg extracts (Zhou, X, et al (200) In Vitro Cell. Dev. Biol.—Animal 36, 293–298; U.S. Pat. No. 6,103,489). This alternative can be applied to all the various examples outlined above where an interest in the membrane bound proteins is a primary consideration. This approach can be especially valuable when screening for a receptor for a given ligand. Such ligands may be drugs, proteins, lipids, phospholipids etc., where the receptor is thought to be a membrane bound protein. The proteins may be immobilized and/or analyzed according to the methods of the invention while membrane bound. Alternatively, they are released from the membranes prior to processing or analysis. To release the translocated proteins or to fully expose the receptors after translation the microsomal membranes are, preferably, lysed using detergents such as 1% Triton X-100. This step allows the binding, enzyme, and/or substrate activity of the proteins to be fully accessed. This lysis step may be carried out either before or after immobilization (using, e.g., the methods based on the modified amino acids precharged on tRNA, or affinity tags included in the expressed protein, or directly immobilized by passive adsorption.

In another alternative embodiment of the invention the proteins produced in the transcription translation reaction are produced with epitope tags or affinity tags that are incorporated into the coding sequence of the various genes of interest. This can be used in place of the modified tRNA to label the products of the translation reaction. These epitope tags can thus be used to bind to solid phases and for detection via the use of specific binding partners to these epitope tags. The specific binding partners are typically antibodies but may include other classes of binding partners. Examples of useful affinity tag/binding partner pairs include GST:glutathione, Peptide:avidin, MBP:maltose, DNA binding protein:DNA, $His_6$:Ni-NTA.

In another alternative embodiment of the invention the proteins produced in the transcription and translation reaction are immobilized directly to the solid phase via various methods such as passive adsorption, or coupling to chemically activated surfaces using various chemistries such as NHS ester, epoxide and maleimide. Proteins immobilized in this way are thus available for detection of specific interactions or reactions.

In another alternate embodiment of the invention, the translation step is omitted from methods of the invention that employ transcription and translation. In this embodiment, mRNA coding for an amino acid sequence of interest, preferably purified mRNA, is added directly to a translation system (preferably a cell-free translation system).

In another alternate embodiment of the invention, the assays of the invention are conducted on proteins that are not generated by in vitro translation, preferably labeled proteins. These may be proteins that are purified from natural sources or expressed in living cells.

In a preferred embodiment of the subject invention these various materials and methods are all handled in multiwell plates. Typically these plates have 20 or more wells, 40 or more wells, 84 or more wells, 96 or more wells, 384 or more wells or 1536 or more wells.

7. EXAMPLES

The examples provided below provide demonstrate certain aspects of the invention. In some examples, an assay technique is used to measure a known activity of a protein. It is understood that the same technique will be applicable for identifying other proteins that have these or similar activities, in particular, proteins in which these activities have not been previously identified.

Materials and Methods

Compound 1 pictured below (Sulfo-TAG™ label-NHS Ester, Meso Scale Diagnostics) is the NHS ester of an electrochemiluminescent label used to label biomolecules for electrochemiluminescence measurements. Labeling of biomolecules was carried out by adding Sulfo-TAG NHS Ester to a solution of the biomolecule in phosphate buffered saline, pH 8.0. The labeled biomolecules were typically purified from unbound label by size exclusion chromatography (using, e.g., Superdex Peptide Gel or Sephadex G50, Pharmacia Biosciences) or reverse phase HPLC. For labeled proteins, the ratio of labels per protein was calculated from the concentration of labels (calculated from the extinction coefficient of Sulfo-TAG label at 455 nm, $\epsilon_{455}$~13,700 $M^{-1}$ $cm^{-1}$) and the concentration of protein (determined using the BCA Protein Assay, Pierce Chemicals).

1

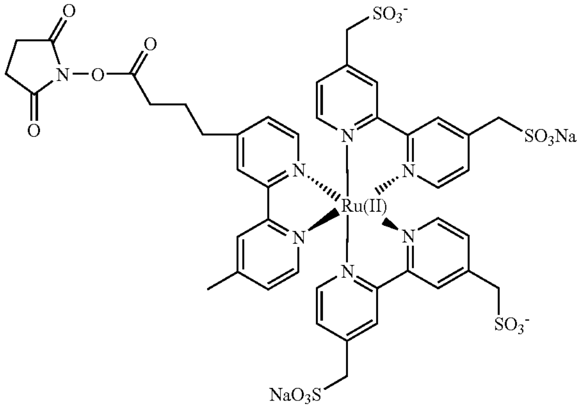

Electrochemiluminescence measurements were carried out using screen-printed carbon ink electrodes patterned on the bottom of specially designed 96-well multi-well or multi-domain multi-well plates. The multi-well plates are described in more detail in copending Application No. 60/301,932 (entitled "Assay Plates, Reader Systems and Methods for Luminescence Test Measurements", filed on Jun. 29, 2001) and particularly in the description of Plate Type B in Example 6.1 (IPR plate) and U.S. application Ser. Nos. 10/185,274 and 10/185,363, filed Jun. 28, 2002, each hereby incorporated by reference. The multi-domain multi-well plates are described in more detail in copending Application No. 60/318,293 (entitled "Methods and Apparatus for Conducting Multiple Measurements on a Sample", filed on Sep. 10, 2001) and U.S. application Ser. No. 10/238,391, entitled "Methods and Apparatus for Conducting Multiple Measurements on a Sample", filed on Sep. 10, 2002, each of which is hereby incorporated by reference. Analogous plates are now commercially available (MSD Multi-Array Plates and Multi-Spot Plates, Meso Scale Discovery). Each well of the plate has a patterned working electrode comprising 1, 4, 7, or 10 assay domains (roughly in the center of the well) that are exposed regions of electrode surface that are defined by a patterned dielectric layer on the electrode surface. The dielectric layer could be used to confine small volumes of liquid to specific assay domains (e.g., to allow for confinement of an immobilization reagent to the working electrode surface). Each well also has two counter electrodes surfaces (roughly at two edges of the well). In some examples, the carbon ink electrodes were treated with an oxygen plasma to increase the surface area of exposed carbon particles and to improve the wettability of the surface (plasma treatment was not required for carrying out the assays, however, in some applications plasma treatment was found to improve the ratio of signal to background as well as assay precision).

The plates were coated with proteins, such as streptavidin, avidin, or an antibody by depositing an aliquot of a protein stock solution (preferably 0.1–0.5 mg/ml in PBS, pH7.4, 0.01% Triton-X100) onto the working electrode surface of each well of 96-well IPR plate and air-drying for 5 hours. Following the coating, the plate was blocked overnight with a blocking solution (containing BSA in a PBS buffer with stabilizers) at 4° C. followed by three washes with PBS. Alternatively, following the adsorption step the plates were washed 3 times with 300 µl of a solution containing 2% Sucrose, 0.1% Tween, 0.2% Kathon, 2.3% Ammonium Dihydrogen Phosphate, dried in a vacuum chamber for 3.5 minutes, placed in foil pouches containing desiccant, vacuum sealed and stored at 4 C. Just prior to use, these plates were blocked with 300 µl of the BSA-containing blocking solution overnight at 37° C. followed by three washes with water.

Unless indicated otherwise, electrochemiluminescence from ECL labels on the surface of the carbon electrodes was induced and measured using an imaging plate reader as described in Examples 6.1 and 6.3 of copending Provisional Application No. 60/301,932 (entitled "Assay Plates, Reader Systems and Methods for Luminescence Test Measurements", filed on Jun. 29, 2001, hereby incorporated by reference) and U.S. application Ser. Nos. 10/185,274 and 10/185,363, filed Jun. 28, 2002, each hereby incorporated by reference. Analogous plate readers are now commercially available (Sector HTS™ instrument, Meso Scale Discovery).

Binding Buffer 1 (BB1) refers to PBS, pH7.4 containing 0.1%BSA, 0.1% bovine IgG, 0.2% tween-20, and protease inhibitors (protease inhibitor cocktail, EDTA free, Roche Applied Science). Binding Buffer 2 (BB2) refers to 25 mM Tris-HCl buffer pH 7.4 containing 100 mM NaCl, 0.05 mM $Na_3VO_4$, 0.004% TritonX-100, 2 mM DTT and protease inhibitors (protease inhibitor cocktail, EDTA free, Roche Applied Science). Proteins were produced by coupled transcription/translation using TnT reaction mixes (Promega Corp, WI). The TNT Quick coupled transcription-translation system (Promega) contains rabbit reticulocyte lysate premixed with most of the reaction components necessary to carry out transcription and translation in vitro (TNT mix), including all the amino acids except methionine. Unless otherwise noted, biotin-labeled in vitro translated proteins were produced in reaction mixtures that contained 8–30 µg/ml of a selected plasmid encoding protein of interest, 5 µl of TNT T7 Quick reticulocyte lysate mix (Promega Corp, WI) or TnT SP6 Quick Coupled Transcription/Translation System (Promega Corp, WI), 20 µM methionine, 50 µM MG-132 (Calbiochem, proteasome inhibitor to inhibit degradation of ubiquitylated proteins by proteasome) and 20 µg/ml biotinylated Lys-tRNA (transcend tRNA, Promega). The reactions were allowed to proceed for 20–90 min at 30° C. The reactions were stopped by the addition of BB1 supplemented with 20 mM AMP-PNP (Sigma, a non-hydrolyzable ATP analog), 20 mM N-ethylmaleimide (Sigma, an irreversible inhibitor of deubiquitylating enzymes) or, alternatively, by the addition of BB2. BB1 was used in screens involving the ubiquitination pathway. BB2 was used for other assay formats. The produced proteins were used in the assays of interest with or without further purification.

Example 1

ECL Assay for Ubiquitylation of RGS4 in Reticulocyte Lysates Using Sulfo TAG™-Labeled Ub The example demonstrates the detection of ubiquitylated proteins produced by in vitro translation by adding labeled ubiquitin in the translation reaction.

The following experiment describes detection and measurement of ubiquitylation of RGS4 (Regulator of G-protein signaling 4), a previously described substrate of a subset of the ubiquitin-proteasome system, called the N-end rule pathway (Davydov and Varshavsky, 2000, *J. Biol. Chem.,* 275:22931–22941).

RGS4 was produced by transcription/translation of 30 μg/ml plasmid pcDNA3-RGS4 (Davydov and Varshavsky, 2000, *J. Biol. Chem.,* 275:22931–22941) under the conditions described in Materials and Methods except for the addition of 1 μM Ub aldehyde (Calbiochem, to inhibit deubiquitylating enzymes) and 5 μM Sulfo-Tag-labeled Ub (having an average of 4.1 labels per Ub molecule). Then 3 μl of the reaction was mixed with 50 μl of BB1 in a 96-well streptavidin-coated non-plasma treated IPR (NPT IPR) plate. The plate was left on a tabletop shaker for 1 hour to allow for binding of biotinylated proteins to the surface. Thereafter the plate was washed three times with PBS followed by the addition of 100 μl of ORIGEN® Assay Buffer (IGEN International, Inc., Gaithersburg, Md.) into each well, and ECL signals were measured using an imaging plate reader (IPR).

In a typical experiment the presence of RGS4-encoding plasmid produced a 5–15 fold higher ECL signal compared to the empty vector (Table 1). We also used this assay to compare ubiquitylation of RGS4 and $RGS4_{C2V}$ mutant, which was previously shown to be a much poorer substrate of the ubiquitin-proteasome pathway in the reticulocyte lysate system (Davydov and Varshavsky, 2000, *J. Biol Chem.,* 275:22931–22941). In our assay RGS4 produced 3–4 fold higher ECL signal compared to $RGS4_{C2V}$, when the same amounts of the corresponding plasmids were added to the reaction mixtures (Table 1)

TABLE 1

IPR readings obtained in the ORIGEN assay using Sulfo-TAG-labeled Ub

| Reticulocyte lysate | Plasmid | Experiment 1 | Experiment 2 |
|---|---|---|---|
| − | None | 539 | 528 |
| + | Empty vector | 1974 | 1857 |
| + | RGS4 | 29294 | 27303 |
| + | RGS4-C2V | 7744 | 7614 |

Example 2

ECL Assay for Ubiquitylation of RGS4 Using Sulfo-TAG Labeled Streptavidin and IPR Plate Coated with FK2 Antibody The example demonstrates detection of ubiquitylated proteins produced by in vitro translation, using immobilized antibodies able to bind the ubiquitin post-translational modification.

Figure 2:
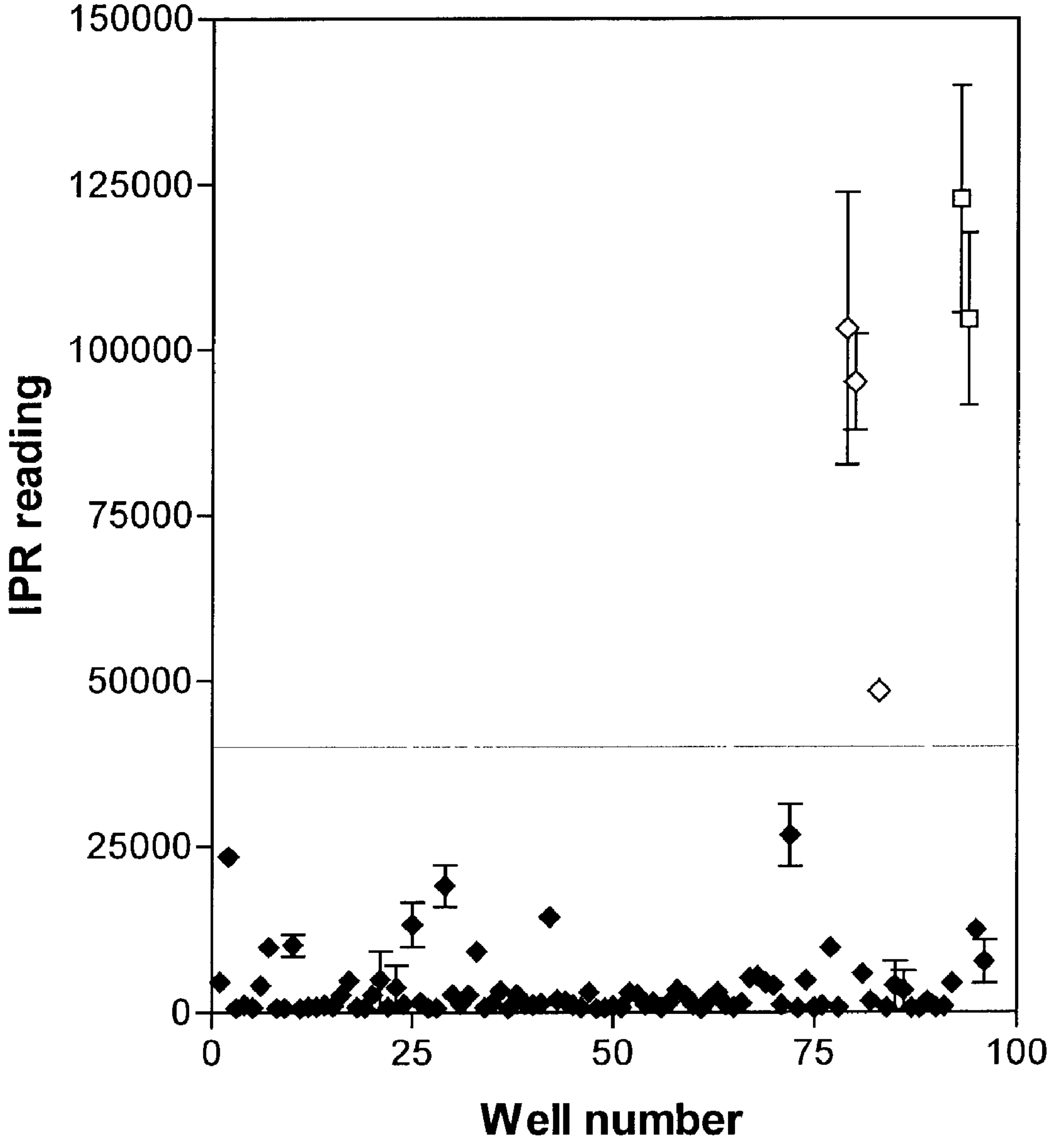
FIG. 2 shows the results electrochemiluminescence assay for identifying ubiquitilated proteins. The plot shows ECL signal (vertical axis) as a function of the specific clone number (horizontal axis).

Transcription-translation reaction mixtures were prepared as described in the Example 1 except that no labeled ubiquitin was added. Some reactions also contained 1 mM dipeptide inhibitor of the N-end rule pathway (either Arg-β-Ala, or Trp-Ala) together with 50 μM bestatin as indicated (Table 2). The reaction was allowed to proceed for 20 min at 30° C. Then 1 μl of the reaction was mixed with 50 μl of BB1 supplemented with 20 mM AMP-PNP, 20 mM N-ethylmaleimide, and 2 μg/ml Sulfo-TAG-labeled streptavidin in a well of an IPR plate coated with an anti-ubiquitin antibody (FK2 antibody, Affiniti). The plate was left on a tabletop shaker for 1 hour to allow for ubiquitylated proteins to bind to the surface of the plate and for the Sulfo-TAG-labeled streptavidin to bind to biotinylated proteins. Thereafter the plate was washed three times with PBS followed by addition of 100 μl of ORIGEN Assay Buffer (IGEN International, Inc., Gaithersburg, Md.) into each well, and ECL signals were measured using an imaging plate reader. In a typical assay the presence of RGS4-encoding plasmid produced a 30–100 fold higher ECL signal compared to the empty vector (FIG. 2, Table 2). This signal was reduced 3–4 fold in the presence of Arg-β-Ala (a type 1 inhibitor of the N-end rule pathway), but not in the presence of Trp-Ala (a type 2 inhibitor of the N-end rule pathway) in agreement with the previous report that RGS4 is a type 1 N-end rule substrate in reticulocyte lysates (Davydov and Varshavsky, 2000, *J. Biol. Chem.,* 275:22931–22941). In the same assay RGS4 produced 3–5 fold higher ECL signal compared to $RGS4_{C2V}$, when the same amounts of the corresponding plasmids were added to the reaction mixtures (Table 2).

TABLE 2

IPR readings obtained in the ORIGEN ubiquitylation assay using Sulfo-TAG-labeled streptavidin and IPR plate coated with FK2 antibody

| Plasmid | Dipeptide inhibitor | Experiment 1 | Experiment 2 |
|---|---|---|---|
| Empty vector | — | 376 | 355 |
| RGS4 | — | 23441 | 23137 |
| RGS4 | Arg-β-Ala | 6224 | 6184 |
| RGS4 | Trp-Ala | 19196 | 19268 |
| RGS4-C2V | — | 5567 | 5362 |

Example 3

ECL Assay for Ubiquitylation of RGS4 Using Sulfo-TAG-Labeled FK2 Antibodies and Streptavidin-Coated IPR Plate The example demonstrates detection of ubiquitylated proteins produced by in vitro translation, using labeled antibodies specific to the Ub post-translational modification.

The protein was prepared as described Example 2 and mixed with 60 μg/ml Sulfo-TAG-labeled FK2 antibody (Affiniti) having 5.6 labels per antibody, in a streptavidin-coated NPT IPR plate. The plate was left on a tabletop shaker for 1 hour to allow for biotinylated proteins to bind to the surface of the plate and for the antibody to bind to ubiquitylated proteins. Thereafter the plate was washed three times with PBS followed by the addition of 100 μl of ORIGEN assay buffer (IGEN International, Inc., Gaithersburg Md.) into each well, and ECL signals were measured using an imaging plate (See, Example 1).

In a typical assay the presence of RGS4-encoding plasmid produced a 15–30 fold higher ECL signal compared to the empty vector (Table 3).

TABLE 3

IPR readings obtained in the ORIGEN ubiquitylation assay using Sulfo-TAG-labeled FK2 antibody and IPR plate coated with streptavidin

| Reticulocyte lysate | Plasmid | IPR readings |
|---|---|---|
| – | None | 2230 |
| + | Empty vector | 4023 |
| + | RGS4 | 85993 |

Example 4

Detection of Ubiquitinated Proteins Produced in a Transcription and Translation Reaction by Capture with an Anti-Ubiquitin Antibody Immobilized on to a Multiwell Plate A. Preparation of Plasmid DNA The following EST clones in bacteria were obtained: IMAGE ID #, 3446518, 3446518, 3446518, 3914731 (RGS4), 3914731 (RGS4), 3914731 (RGS4) (Incyte, Palo Alto). Bacteria containing EST clones were grown in 2 ml LB with 50 μg/ml Amp, and DNA was isolated using QIAprep Spin Miniprep Kit (Qiagen). DNA yield was 5–20 μg.

B. ECL Ubiquitylation Assay

Proteins were prepared from the EST clones in transcription-translation reaction mixtures (total volume 12.5 uL) as described in the Materials and Methods except for the addition of 1 μM Ub aldehyde (Calbiochem). Then 1 μl of the reaction product was mixed with 50 μl of BB1 supplemented with 20 mM AMP-PNP, 20 mM N-ethylmaleimide and 2 μg/ml Sulfo-TAG-labeled streptavidin in to each well of an IPR plate coated with FK2 antibody. The plate was left on a tabletop shaker for 1 hour to allow for ubiquitylated proteins to bind to the surface of the plate and for the Sulfo-TAG-labeled streptavidin to bind to biotinylated proteins. Thereafter the plate was washed three times with PBS followed by addition of 100 μl of ORIGEN Assay Buffer (IGEN, International, Inc., Gaithersburg Md.) into each well, ECL signals were measured using an imaging plate reader.

All the three RGS4-encoding IMAGE clones (3912628, 3914731 and 3920860) produced strong specific signal in this assay. Analysis of additional 30 random IMAGE clones identified one strong and few weak substrates of ubiquitylation. Clone 3446518 identified as a strong positive encodes uncharacterized protein CGI-147 of approx 19 kDa (FIG. 1).

As previously reported, RGS4 is a substrate of the N-end rule-dependent ubiquitylation in reticulocyte lysates (Davydov and Varshavsky, 2000, *J. Biol. Chem.,* 275:22931–22941). To determine if the protein produced from clone 3446518 was similarly ubiquitylated through the N-end rule pathway, the ECL ubiquitylation assay was performed in the presence of dipeptide inhibitors Arg-β-Ala (type 1 inhibitor of the N-end rule pathway), or Trp-Ala (type 2 inhibitor of the same pathway). As was shown on FIG. 2, the RGS4 signal was reduced 3–4 fold in the presence of Arg-β-Ala (a type 1 inhibitor of the N-end rule pathway), but not in the presence of Trp-Ala (a type 2 inhibitor of the N-end rule pathway) in agreement with the previous report that RGS4 is a type 1 N-end rule substrate in reticulocyte lysates (Davydov and Varshavsky, 2000, *J. Biol. Chem.,* 275:22931–22941). In contrast, the dipeptides had little effect on the assay signal from clone 3446518 (FIG. 2). Thus, a different pathway of the ubiquitin system mediates ubiquitylation of the protein produced from clone 3446518.

TABLE 4

ECL readings obtained in the ECL based ubiquitylation assay using Sulfo-TAG-labeled streptavidin and IPR plate coated with FK2 antibody

| IMAGE ID | Dipeptide inhibitor | Experiment 1 | Experiment 2 | Experiment 3 |
|---|---|---|---|---|
| 3446518 | — | 11767 | 11551 | 11660 |
| 3446518 | Arg-β-Ala | 10484 | 10829 | 9665 |
| 3446518 | Trp-Ala | 11249 | 11550 | 11464 |
| 3914731 (RGS4) | — | 41670 | 43729 | 41806 |
| 3914731 (RGS4) | Arg-β-Ala | 15074 | 15016 | 14555 |
| 3914731 (RGS4) | Trp-Ala | 41229 | 40401 | 38552 |
| mock | — | 358 | 348 | 316 |

C. $^{35}S$-Labeling of Proteins and SDS-Gel Electrophoresis

The same clones, which were assayed in ECL ubiquitylation assay, were used to produce $^{35}S$-labeled proteins. Transcription-translation reaction mixtures contained components described in Materials and Methods and 400 μCi/ml $^{35}S$-methionine (AmershamPharmaciaBiotech), 1 μM Ub aldehyde (Calbiochem) in a total volume of 12.5 μl. The reaction was allowed to proceed for 45 min and was stopped by addition of 4-fold excess of SDS-gel loading buffer (Invitrogen) with 5% β-mercaptoethanol. The samples were heated for 5 min at 95° C. prior to loading, and SDS-gel electrophoresis was performed on 10–20% Tris-glycine gels (Novex) followed by autoradiography. As can be seen in FIG. 1, the vast majority of the tested clones produced protein.

Example 5

Detection of Ubiquitylation of RGS4 Using Sulfo-TAG Labeled Ub in M-8 Analyzer The Example describes detection of ubiquitinated proteins produced in a transcription and translation reaction via capture onto magnetic beads in a multiwell plate format.

For M-8 ubiquitylation assays we assembled reaction mixtures which contain 30 μg/ml plasmid pcDNA3-RGS4 or pcDNA3-RGS4-C2V (Davydov and Varshavsky, 2000, *J. Biol. Chem.,* 275:22931–22941) as indicated in Table 5, and carried out the TnT reactions in the presence of labeled ubiquitin as described in the Example 1. Then 10 μl of the reaction product was mixed with 50 μl of BB1 supplemented with 20 mM AMP-PNP, 20 mM N-ethylmaleimide, and 20 μg streptavidin coated magnetic beads (Streptavidin DynaBeads, Dynal) in a 96-well plate. The plate was left on a tabletop shaker for 1 hour to allow for binding of biotinylated proteins to Dynal beads. Thereafter the volume in each well was adjusted to 200 μl with binding buffer, and ECL signals were measured in M-8 Analyzer (IGEN International, Inc., Gaithersburg, Md.).

TABLE 5

| M-8 readings obtained in the ORIGEN assay using Sulfo-TAG labeled Ub | | | |
|---|---|---|---|
| Reticulocyte lysate | Plasmid | Experiment 1 | Experiment 2 |
| − | None | 3798 | 5226 |
| + | Empty vector | 8575 | 9004 |
| + | RGS4 | 87339 | 71463 |
| + | RGS4-C2V | 30201 | 26712 |

Example 6

Detection of Ubiquitylation of RGS4 Using Sulfo-TAG Labeled FK2 Antibody in M-8 Analyzer The example shows detection of ubiquitinated proteins produced in a transcription and translation reaction via capture on to magnetic beads in a multiwell plate format. In this example, ubiquitination is detected using labeled antibody.

Transcription-translation reaction mixtures containing pcDNA3-RGS4 or pcDNA3-RGS4-C2V plazmids(Davydov and Varshavsky, 2000, *J. Biol. Chem.,* 275:22931–22941) were prepared and used as described in the Example 2. The reaction products were mixed with 3 μg Sulfo-TAG labeled FK2 antibody in a 96-well plate in a binding buffer. Sulfo-TAG labeled FK2 antibody had 5.6 Sulfo-TAG labels per antibody molecule. The plate was left on a tabletop shaker for 1 hour to allow for binding of the antibody to ubiquitylated proteins. Then 30 μl of BB1 supplemented with 20 mM AMP-PNP, 20 mM N-ethylmaleimide and containing 20 μg dynal beads streptavidin (Dynal) were added to each well, and the plate was left on the shaker at room temperature for another hour to allow for binding of biotinylated proteins to dynal beads. Thereafter the volume in each well was adjusted to 200 μl with BB1, and ECL signals were measured in M-8 Analyzer (IGEN International, Inc., Gaithersburg Md.).

TABLE 6

| M-8 readings obtained in the ORIGEN assay using Sulfo-TAG labeled FK2 antibody | | |
|---|---|---|
| Reticulocyte lysate | Plasmid | M-8 readings |
| − | None | 6330 |
| + | Empty vector | 6414 |
| + | RGS4 | 187328 |
| + | RGS4-C2V | 14689 |

Example 7

Assay to Screen for Tyrosine Kinase Activity

The example demonstrates an ORIGEN based HTS assay for tyrosine kinase activity of fer (fms/fps related) protein tyrosine kinase, testis specific 2 (Fert2) expressed in reticulocyte lysate. The assay format developed for this purpose utilizes following steps:

Proteins were produced in an in vitro transcription and translation reaction. The reaction mix consisted of the following: 1–150 ng of plasmid DNA (Mock Luciferase, Promega, or Fert2 (IMAGE ID#4485050, Incyte Genomics, CA), and components described in Materials and Methods in a final volume of 6.25 μl. This resulted in the transcription and translation of the various proteins with incorporated biotin groups randomly at the positions of the various lysine residues determined by the coding sequence for the gene. The reaction was stopped by mixing with BB2. Biotinylated proteins from 50 μl of the mixture (representing 0.5 μl to 1 μl of TnT reaction) were immobilized onto SA or avidin coated NPT-IPR plates by shaking at room temperature for 45 mm. The unbound components of the reaction containing endogenous kinases were removed by three washes with TT-buffer (25 mM Tris-HCl buffer pH 7.4 and 0.004% Triton), two five minutes washings with high-salt wash buffer (25 mM Tris-HCl buffer pH 7.4, 0.004% Triton, 1M NaCl and 5 mM DTT) and 3 more washes with TT-buffer. To these immobilized and purified proteins a tyrosine kinase substrate, 5 nM pEY (poly Glu-Tyr, Sigma, MO), was added in a 50 μl reaction solution containing 5 mM $MgCl_2$, 5 mM $MnCl_2$, 100 μM ATP, 25 mM Tris-HCl buffer pH 7.4, 0.05 mM $Na_3VO_4$, 0.004% TritonX-100, 2 mM DTT and EDTA-free protease inhibitor (Roche Molecular Biochemicals). This mixture was incubated with shaking at room temperature overnight to allow phosphorylation of the pEY substrate by the immobilized kinases. Following this incubation, 45 μl of this mixture was transferred to a streptavidin or avidin-coated NPT IPR plate coated with biotinylated anti-phosphotyrosine antibody (PY20, Zymed labs, CA) followed by incubation for 30 minutes at room temperature to allow the binding of the phosphorylated pEY substrate to the PY20 coated NPT plate. Following this binding step, 50 ng Sulfo-TAG labeled anti-phosphotyrosine in buffer containing 25 mM Tris-HCl buffer pH 7.4, 5 mM $MgCl_2$, 0.05 mM $Na_3VO_4$, 0.004% TritonX-100, 2 mM DTT and 0.05% IgG was added followed by incubation at room temperature for 30 mm. The unbound reagents were removed by one time washing with water, and the TAG label was detected in presence of 150 μl IPR assay buffer (0.4 mM Gly-Gly buffer, pH 7.8, 1 mM EDTA, 0.1 M TPA). The ECL signals were measured using an imaging plate reader.

The ECL signal produced by kinase activity of Fert2, expressed in 0.5 to 1 μl of TnT reaction, was about 1000 to 1100 fold higher than the background noise produced by Mock (Luciferase) (see Table 7).

TABLE 7

| | ECL signal |
|---|---|
| Fert2 | 1,608,671 |
| Mock | 1,478 |

The kinase activity from Fert2 demonstrated by this assay format was specific, as the signal decreased significantly in the absence of Fert2 DNA, biotinylated Lysine tRNA or the substrate pEY (see Table 8).

TABLE 8

| Plasmid | Reagents | ECL signal |
|---|---|---|
| + | no tRNA | 1,752 |
| − | | 1,445 |
| + | no pEY | 1,309 |
| + | | 1,608,671 |

The phosphorylation of the substrate was further demonstrated to be the result of kinase activity as the signal was abolished in the absence of ions or in the presence of EDTA (see Table 9).

TABLE 9

| | Mock | Fert2 |
|---|---|---|
| Control | 1,320 | 1,637,307 |
| no Mg, no Mn | 1,027 | 2,851 |
| +EDTA | 911 | 1,287 |

A concentration dependent expression of Fert2 activity was seen when increasing amounts of cDNA was expressed and assayed by this format, however, a maximum activity was registered at the DNA concentration of 100 ng of DNA per 5 µl of TnT reaction. A background level of signal seen at all the DNA concentrations of Mock was considerably lower than the signal seen from the kinase (see Table 10).

TABLE 10

| DNA µg/5 µl | Mock | Fert2 |
|---|---|---|
| 0.00 | 1,027 | 1,027 |
| 0.001 | 3,232 | 4,432 |
| 0.003 | 2,648 | 129,797 |
| 0.010 | 2,155 | 1,440,103 |
| 0.020 | 2,299 | 1,463,489 |
| 0.040 | 2,880 | 1,523,121 |
| 0.060 | 2,774 | 1,553,370 |
| 0.080 | 1,478 | 1,608,671 |
| 0.100 | 1,413 | 1,687,039 |
| 0.125 | 1,133 | 1,626,868 |
| 0.150 | 1,639 | 1,599,024 |

Example 8

Assay to Screen for Autophosphorylation Activity

The example demonstrates an ORIGEN based HTS assay for autophosphorylation activity of Spleen Tyrosine kinase and Eph receptor-A7 expressed in reticulocyte lysate. Using in vitro expression screening strategy, we have demonstrated the autophosphorylation activity from full-length clones Spleen Tyrosine Kinase (SYK) and Eph receptor-A7 (EphA7). The assay format developed for this purpose utilizes following steps:

Proteins were produced from DNA plasmids of Mock Luciferase, Promega, tyrosine kinase clone Spleen Tyrosine kinase (SYK, IMAGE ID# 3870426) and Eph receptor-A7 (EphA7, IMAGE ID# 3991628) (Incyte Genomics, CA) and immobilized on streptavidin or avidin coated NPT-IPR plates as described in the Example 7. To promote autophosphorylation in these immobilized and purified proteins, Mn++ ions were added in a 50 µl reaction containing 5 mM $MgCl_2$, 5 mM MnCl2, 100 µM ATP, 25 mM Tris-HCl buffer pH 7.4, 0.05 mM $Na_3VO_4$, 0.004% TritonX-100, 2 mM DTT and EDTA-free protease inhibitor (Roche Molecular Biochemicals). This mixture was incubated with shaking at room temperature overnight to allow autophosphorylation. Following this incubation, wells were washed 2 times with TT-buffer and 2 times with water. Following this step, 50 ng Sulfo-TAG labeled anti-phosphotyrosine in buffer containing 25 mM Tris-HCl buffer pH 7.4, 5 mM $MgCl_2$, 0.05 mM $Na_3VO_4$, 0.004% TritonX-100, 2 mM DTT and 0.05% IgG in a final volume of 50 µl was added followed by incubation at room temperature for 45 min. The unbound reagents were removed by one time washing with water, and the TAG label was detected in presence of 150 µl IPR assay buffer (0.4 mM Gly—Gly buffer, pH 7.8, 1 mM EDTA, 0.1 M TPA). The ECL signals were measured using an imaging plate reader.

The ECL signal produced by autophosphorylation activity of tyrosine kinases expressed in 0.5 µl of TnT reaction, was about 25 fold (in SYK) or 47 fold (in EphA7) higher than the background noise produced by Mock (Luciferase) (see Table 11).

TABLE 11

| | ECL signal |
|---|---|
| SYK | 21,495 |
| EphA7 | 39,967 |
| Mock | 847 |
| Water | 763 |

Example 9

Screening for Tyrosine Kinase Substrates

The example demonstrates an ORIGEN based HTS assay for SRC phosphorylation of SKAP-HOM in reticulocyte lysate using Sulfo-TAG labeled anti-phosphotyrosine. Tyrosine kinases may phosphorylate protein substrates with high specificity. However, the map of such substrates for each of the known kinase is far from being complete. We have developed a screening method to detect specific phosphorylations of in vitro expressed cDNAs. The assay format developed for this purpose utilizes following steps:

Proteins were produced in an in vitro transcription and translation reaction and immobilized on streptavidin or avidin coated NPT-IPR plates as described in the Example 7. DNA plasmids used in this example were Mock Luciferase, Promega, SKAP-HOM (IMAGE ID# 3893964, Incyte Genomics) or tyrosine kinase clone Spleen Tyrosine kinase (SYK, IMAGE ID# 3870426, Incyte Genomics, CA). Additionally, NPT-IPR plates were washed 3 times with water following protein immobilization. The Immobilized and purified proteins were de-phosphorylated by adding two units of Shrimp alkaline phosphatase (SAP, Roche Molecular Biochemicals) in 50 µl reaction containing 50 mM Tris-HCl buffer pH 8.5 and 5 mM $MgCl_2$ for 2 hours at 37 C. The de-phosphorylated proteins were washed 3 times with water and specifically re-phosphorylated in the presence of known kinase (0.1 mU SRC/µl) in a buffer containing 25 mM Tris-HCl buffer pH 7.4, 5 mM $MgCl_2$, 0.05 mM $Na_3VO_4$, 0.004% TritonX-100 and 2 mM DTT. The specifically phosphorylated proteins were washed one time with water and detected in presence of 50 ng Sulfo-TAG labeled anti-phosphotyrosine in buffer containing 25 mM Tris-HCl buffer pH 7.4, 5 mM $MgCl_2$, 0.05 mM $Na_3VO_4$, 0.004% TritonX-100, 2 mM DTT and 0.05% IgG in a total volume of 50 µl at room temperature for 45 min. The unbound reagents were removed by washing three times with water, and the TAG label was detected in presence of 150 µl IPR assay buffer (0.4 mM Gly—Gly buffer, pH 7.8, 1 mM EDTA, 0.1 M TPA). The ECL signals were measured using an imaging plate reader.

We have demonstrated that SRC specifically phosphorylates SKAP-HOM, a protein that was predicted to be a potential substrate based on its homology to known SRC substrates (Curtis D J, et al (2000) Exp Hematol, 28, 1250–9; Marie-Cardine A, et al (1998) FEBS Lett, 435, 55–60). The control proteins SYK or Luciferase (Mock) did not show significant levels of phosphorylation by SRC. The non-specific tyrosine phosphorylation of Mock, SYK or endogenous substrates of the TnT system were of considerable lower magnitude, about 17 fold lower to that of the SKAP-HOM (Table 12).

TABLE 12

| Reticulocyte lysate | | − | + | + | + | + |
|---|---|---|---|---|---|---|
| Plasmid | | none | SYK | SKAP-HOM | Mock | none |
| no SRC | no SAP | 338 | 1,003 | 496 | 370 | 374 |
| no SRC | +SAP | 197 | 271 | 307 | 265 | 270 |
| +SRC | +SAP | 1,014 | 1652 | 32,028 | 1147 | 1,033 |

Example 10

Screens for Phosphopeptide Binding Proteins

Example of ECL based assays for phosphopeptide and protein interaction. The model assay measures the interaction between βTRCP and phosphorylated IkBa peptide captured on a solid phase.

A phosphopeptide derived from the IkBa degradation motif (SEQ ID NO: 1) and a phosphopeptide derived from c-Myc (SEQ ID NO: 4) were chemically synthesized (New England Peptide, Fitchburg Mass.) with the following sequences respectively:

H2N-LKKERLLDDRHD(p)SGLD(p)SMKDEEYC-COOH.

H2N-CPSEDIWKKFELLP(p)TPPL(p)SPSRRSGL-COOH

The cystine residues at the C- or N-terminuses were added to the sequences to allow for covalent coupling of the peptide to a carrier protein. The IkBa peptide (SEQ ID NO: 1) contains the six-residue motif with "DSGXXS" consensus sequence that confers the binding to the βTRCP, an F-box/WD40 repeat containing protein. The binding of the peptide to βTRCP is absolutely dependent on the presence of the two phosphoserine residues. Singly phosphorylated peptide or phosphothreonine substitution abolish interaction. The c-Myc derived phosphopeptide (SEQ ID NO: 4) was used as a control.

A maleimide pre-activated BSA (Pierce, Pittsburgh Pa.), which contains estimated 17 active maleimide groups on the protein surface, was used as the protein carrier, and was supplied as a lyophilized preparation. Coupling of the IkBa peptide (SEQ ID NO: 1) to the pre-activated BSA was carried out with 2 mg BSA (30 nmol) and 17 equivalents of the 25 residue phosphopeptide in 400 μl PBS. The reaction was terminated with 2 mM L-cystine after incubation at room temperature for 30 minutes. The peptide:BSA conjugate was then purified on PD-10 gel filtration column to remove uncoupled peptide and analyzed with SDS PAGE to monitor the coupling reaction. Since the molecular weight of phosphorylated IkBa peptide (SEQ ID NO: 1) is 3055, a BSA carrier with all 17 maleimide groups conjugated to this peptide would have a molecular weight of 119 kD, which is in agreement with the apparent molecular weight observed on the denaturing SDS gel. After coupling and purification, the column fractions containing the peptide:BSA conjugates were pooled and the protein concentration of the pooled samples was determined by BCA assay (Pierce, Pittsburgh Pa.). $NaN_3$, (0.02%) was added to the final peptide:BSA conjugate sample for long term storage at 4° C.

To prepare IPR plates for use in the assay, approximately 2.4 pmol BSA, 1.2 pmole IκBα-24pp peptide-BSA conjugate or 1.2 pmole of Myc-p58Tp62S peptide-BSA conjugate in 2.5 μl were deposited on the carbon working electrode surface in a single well of a 96-well plate. At this stage, the plates were dried then used or stored under desiccated condition. A few hours prior to usage, the plates were rehydrated and blocked with 3% BSA, in PBS.

Two βTRCP genes, βTRCP1 and βTRCP2, are present in the human genome on chromosome 5 and 10, respectively. The coding sequence of these two genes shares over 90% identity and several full-length cDNAs of which are available as EST clones from Incyte (Palo Alto, Calif.) IMAGE #3491843 and 4237375. Also included were three other non specific EST clones as controls (Incyte, Palo alto, Calif.). Plasmid DNAs from these EST clones and other clones were prepared -using the Qiagen miniprep kit (Qiagen, Los Angeles, Calif.). These DNAs were used to produce the βTRCP protein and proteins encoded by the other DNAs as described in the Example 7. Proteins were transferred into wells of the peptide-coated and BSA-blocked IPR plates. Sulfo-TAG labeled streptavidin (50 to 100 ng/well) was added to each well as the detection agent. The binding reaction can be carried out in cold room for over two hours or at room temperature for 1 hour without significant difference. After binding, the IPR plates were washed twice with PBS and 100 μl of ORIGEN assay buffer (IGEN International, Inc., Gaithersburg, Md.) was added to each well before reading the ECL signal. The ECL signals were measured using an imaging plate reader (IPR). A typical result of this assay is given in Table 13, which shows the ECL signals obtained when 3 random, negative cDNAs and 2 positive cDNAs are translated and subjected to the phosphopeptide binding assay. The protein products from these two positive clones bound specifically to the phosphorylated IkBa25pp peptide but not to the control peptide derived from oncogene c-Myc despite of the fact that the c-Myc peptide contains a similarly diphosphorylated motif: P(p)TPPL(p)S. These results demonstrate the sensitivity and specificity of this assay for binding activities encoded by the DNA clones.

TABLE 13

| | Average ECL signal | | |
|---|---|---|---|
| Clones name or IMAGE# | IkBa peptide [SEQ ID No. 1] | c-Myc peptide [SEQ ID No. 4] | BSA control |
| No DNA | 379 | 344 | 337 |
| 3491843 (βTRCP1) | 40879 | 2118 | 1719 |
| 4237375 (βTRCP2) | 21501 | 896 | 672 |
| 3872466 | 371 | 351 | 352 |
| 4419252 | 341 | 316 | 342 |
| 39907115 | 368 | 341 | 342 |

Example 11

Assay for Interaction among Multiple Proteins and their Cognate Recognition Phosphopeptides Arrayed on Multiple Spots in a Single Well Four phosphopeptides and their cognate binding proteins (Table 14) were selected for an integrated assay of multiple peptide-protein interaction in 4-spot Multi-Array plates. The IkBa-24pp peptide and its binding protein, βTRCP, are described in Example 10. The remaining peptides are derived from the carboxyl terminus of the EGF receptor. These phosphotyrosine containing peptides are recognized by different adaptor or effecter proteins of the receptor tyrosine kinase signaling pathway.

TABLE 14

| | Peptide name | Binding protein | Sequence |
|---|---|---|---|
| #1 | EGFR-pY992 (SEQ ID NO: 5) | PLCγ | DADE(p)YLIPQQGFFSSPSTSC |
| #2 | EGFR-pY1068 (SEQ ID NO: 7) | Grb2, PLCγ | LPVPE(p)YINQSVPKRPAGSVC |
| #3 | EGFR-pY1148 (SEQ ID NO: 9) | Shc | KGSHQISLDNPD(p)YQQDFFPKEAKPNC |
| #4 | IkBa-24pp (SEQ ID NO: 1) | βTRCP | LKKERLLDDRHD(p)SGLD(p)SMKDEEYC |

These four peptides were coupled to BSA carrier protein through cystine residue. After purification on PD-10 gel filtration columns, the peptide-BSA conjugates were then deposited on the assay domains of a 4-spot multi-array IPR plate (i.e., in one of the four exposed regions of working electrode defined by the dielectric layer) with an automated micro-dispensing system (Bio-Dot Dispenser, Bio-Dot, Irvine Calif.). Typically about 120 fmole of peptide:BSA conjugate in 0.25 μl was deposited on each spot of a 4-spot multi-array IPR plate. These plates are dried then used or stored under desiccated conditions. A few hours prior to usage the plates were rehydrated and blocked with 3% BSA in PBS. EST clones encoding βTRCP1 (3491843), βTRCP2 (4237375), mCBP (3872466) Grb2 (4398016) and PLCγ (4419252) (Incyte, Palo Alto, Calif.), were isolated using a QIA-prep column (QIAGEN, Los Angeles, Calif.) and used to program protein expression in a Quick coupled SP6 TnT reaction supplemented with Transcend biotin-tRNA label following the manufactures protocol (Promega, Madison Wis.). The in vitro translated and biotin-labeled proteins were then assayed in the 4-spot multi-array IPR plates under conditions described in Example 10. As shown in Table 15, ECL signals imaged from spot 1(IkBa-24pp-BSA conjugate) were 100-fold higher in wells containing βTRCP1 and βTRCP2 than in wells derived from TnT reaction mixtures containing no exogenous DNA. By contrast spots 2–4 in the same wells gave low ECL signals. Thus, in this assay format, each peptide not only serves as the capture agent for assaying specific interaction with its binding protein, but also at the same time serves as a control for other peptide-protein interaction to be determined in the same well. The same principle was illustrated once again by the binding of Grb2 and PLCγ proteins with EGFR carboxyl terminus phosphotyrosine peptides. These proteins also were found to bind specifically to the correct peptide sequences. An expected a cross binding reactivity was seen between PLCγ protein and EGFR-pY992 (SEQ ID NO: 5) and pY1068 (SEQ ID NO: 7) peptides.

These results demonstrated the potential of the use of multiple binding domains (4 spots) in a single well to increase both the speed and specificity of screens for binding interactions. This method also provides for significant savings of reagents in a screen with 4 differing binding species.

TABLE 15

| | | Single-well assay for multiple peptide-protein interactions | | | | | |
|---|---|---|---|---|---|---|---|
| Spot | Peptide-BSA | 3491843 βTRCP1 | 4237375 βTRCP2 | 3872466 mCBP | 4398016 Grb2 | 4419252 PLCγ | No DNA control |
| 1 | IkBa-24pp (SEQ ID NO: 1) | 2466 | 5040 | 446 | 22 | 26 | 14 |
| 2 | EGFR-pY1148 (SEQ ID NO: 9) | 36 | 35 | 278 | 20 | 110 | 13 |
| 3 | EGFR-pY1068 (SEQ ID NO: 7) | 24 | 24 | 126 | 441 | 1485 | 10 |
| 4 | EGFR-pY992 (SEQ ID NO: 5) | 54 | 60 | 498 | 44 | 1404 | 31 |

Example 12

ECL Based Assays for Phosphopeptide and Protein Interaction

This example demonstrates a multi-plexed approach for screening for proteins that bind phosphopeptides. The assay used an array of multiple phosphopeptides for identifying multiple protein-peptide interactions in a single well and used a coded multiplex approach.

The following peptides were chemically synthesized (New England Peptide, Fitchburg Mass.). The peptides were coupled to pre-activated maleimide BSA according to the procedure described in Example 11.

```
EGFR-pTyr992
DADE(p)YLIPQQGFFSSPSTSC              (SEQ ID NO: 5)

EGFR-pTyr1068
LPVPE(p)YINQSVPKRPAGSVC              (SEQ ID NO: 7)
```

-continued

```
EGFR-pTyr1148
KGSHQISLDNPD(p)YQQDFFPKEAKPNC       (SEQ ID NO: 9)

IkBa-24ppC
LKKERLLDDRHD(p)SGLD(p)SMKDEEYC      (SEQ ID NO: 1)

Myc-p58Tp62S
CPSEDIWKKFELLP(p)TPPL(p)SPSRRSGL    (SEQ ID NO: 4)

Smad3C
CGPLQWLDKVLTQMGSPHNPIS(p)SV(p)S     (SEQ ID NO: 11)
```

The peptides EGFR-pTyr992 (SEQ ID NO: 5), EGFR-pTyr1068 (SEQ ID NO: 7) and EGFR-pTyr1148 (SEQ ID NO: 9) were derived from the phosphorylation sites in EGF receptor. Peptide IkBa-24ppC (SEQ ID NO: 1) is described in Example 10. The peptides Myc-p58Tp62S (SEQ ID NO: 4) and Smad3C (SEQ ID NO: 11) are derived from c-Myc and SMAD3. In the case of the EGFR and IkBa peptides, certain binding partners are known (Table 16).

TABLE 16

| Peptide | SEQ ID NOs | Binding Partner |
|---|---|---|
| EGFR-pTyr992 | (SEQ ID NO: 5) | Phospholipase C gamma 1 (PLCγ) |
| EGFR-pTyr1068 | (SEQ ID NO: 7) | Grb 2 |
| EGFR-pTyr1148 | (SEQ ID NO: 9) | Shc 1 |
| IkBa-24ppC | (SEQ ID NO: 1) | βTRCP1 and βTRCP2 |

To prepare the Multi-Spot IPR plates, in this example we made use of pools of the peptide:BSA conjugates to coat each of 4 spots per well in a 96 well plate. To achieve this we made the following pools;

Pool A; EGFR-pTyr1148, IkBa-24ppC, Myc-p58Tp62S.

Pool B; EGFR-pTyr992, EGFR-pTyr1148, Smad3C.

Pool C; EGFR-pTyr1068, IkBa-24ppC, Smad3C.

Pool D; EGFR-pTyr992, EGFR-pTyr1068, Myc-p58Tp62S.

This combination of the various peptides results in any single peptide being present in two pools. Each of these four pools is then spotted on to a unique spot in a 4 spot array. In this way any single binding protein with specificity for only one of the peptides would bind to two spots; the identity of the two spots would allow the identification of the peptide involved in the binding reaction. The coding resulting from the pools described above are presented in Table 17.

TABLE 17

| Peptide | SEQ ID NOs | Pool Code |
|---|---|---|
| EGFR-pTyr992 | (SEQ ID NO: 5) | B, D |
| EGFR-pTyr1068 | (SEQ ID NO: 7) | C, D |
| EGFR-pTyr1148 | (SEQ ID NO: 9) | A, B |
| IkBa-24ppC | (SEQ ID NO: 1) | A, C |
| Myc-p58Tp62S | (SEQ ID NO: 4) | A, D |
| Smad3C | (SEQ ID NO: 11) | B, C |

Typically approximately 120 fmole of peptide:BSA conjugate in 0.25 μl was deposited on each spot of a 4-spot multi-array IPR plates using a BioDot Dispenser (Bio-Dot Inc., vIrvine Calif.). At this stage, the plates were dried then used or stored under desiccated condition. A few hours prior to usage, the plates were rehydrated and blocked with 3% BSA, in PBS.

To test the system the following EST clones IMAGE # 3491843, 4237375, 4398016, 4419252, 3872466, 3907115 were obtained. These clones express the following genes βTRCP1, βTRCP2, Grb2, PLCγ, CBP and Shc1, respectively. Plasmid DNAs from these various clones were prepared using the Qiagen miniprep kit (Qiagen, Los Angeles, Calif.). These DNAs were used to produce proteins as described in the Materials and Methods. Proteins were transferred to a well of the 4 spot peptide-coated and BSA blocked ECL plates. The binding assay (using Sulfo-TAG labeled streptavidin as a detection agent) was carried our according to the procedures described in Example 11.

The ECL signals for each pooled peptide spot (A–D) are presented in Table 18. Table 18 also lists the code (i.e., pattern of positive spots) obtained with each protein. The identity of the binding peptide as determined by the code is presented in Table 19.

TABLE 18

| Spot | Blank | 3491843 βTRCP1 | 4237375 βTRCP2 | 4398016 Grb2 | 4419252 PLCγ | 3872466 CBP | 3907115 Shc1 |
|---|---|---|---|---|---|---|---|
| A | 22 | 9536 | 7791 | 36 | 239 | 19 | 260 |
| B | 54 | 208 | 105 | 38 | 2783 | 30 | 318 |
| C | 28 | 11184 | 8615 | 509 | 1550 | 22 | 24 |
| D | 20 | 171 | 74 | 386 | 3388 | 15 | 26 |
| Code | Neg. | A, C | A, C | C, D | B, C, D | Neg. | A, B |

TABLE 19

| Clone | Peptide determined from code | Match with expected result |
|---|---|---|
| No DNA | Negative | Expected |
| 3491843 | IkBa-24ppC | Expected |
| 4237375 | IkBa-24ppC | Expected |
| 4398016 | EGFR-pTyr1068 | Expected |
| 4419252 | EGFR-pTyr992 & EGFR-pTyr1068 | Expected |
| 3872466 | Negative | Expected |
| 3907115 | EGFR-pTyr1148 | Expected |

The expected two spot matches were observed in all cases except for clone 4419252 (a PLCγ clone). This clone gave a three spot code that was indicative of the protein binding two different peptides. This result was expected and also observed in Example 11.

These results demonstrate the potential of this method of pooling peptides or binding species in combination with multiple spots to improve the screening of large numbers of binding species immobilized on to a solid phase.

Example 13

Direct Coating of Proteins onto Solid Phase

EST clones IMAGE #'s 3886018, 3910505 and 3915089 were obtained from Incyte (Palo Alto, Calif.). Plasmid DNA was prepared from these EST clones using QIAprep96 Turbo Miniprep (cat#27191, QIAgen, Los Angeles, Calif.), according to manufacturer's instructions. cDNA was eluted using 150 μl buffer EB (QIAgen).

The proteins were produced in the transcription translation (TnT) reaction as described in the Materials and Methods.

For binding of the proteins from the TnT reaction to the solid phase we used the following protocol. 30 μl PBS pH 7.4 was added to each well of an NPT IPR plate. 2 μl of the TnT reaction was added to each well, the plate was covered with sealing film and incubated for 1 h at ambient temperature with shaking. After incubation, the plate was washed 3× with PBS. 50 ng Sulfo-TAG labeled streptavidin (see Materials and Methods) was added to each well in a 50 μl volume using IPR assay buffer (25 mM Tris pH7.4, 0.005% Triton, 2 mM DTT, 1% BSA, protease inhibitors) and the IPR plate was incubated for 1 h at RT with shaking. After incubation, the plate was washed 3× with PBS, 100 μl ORIGEN assay buffer (IGEN International, Inc., Gaithersburg, Md.) added to each well and the ECL signals measured.. The results in Table 20 demonstrate the binding of proteins directly to a solid phase from the TnT reactions and show that this procedure can be used to measure the amount of the translated protein. This procedure provides a useful control for correcting biases in screening data resulting from variation in the concentrations of translated proteins.

TABLE 20

| | Clone ID | | | |
|---|---|---|---|---|
| | 3886018 | 3910505 | 3915089 | No DNA |
| ECL signal | 6198 | 4835 | 7669 | 1192 |

Example 14

Assay to Detect Binding Species Produced by in Vitro Translation Using a Magnetic Bead Based Assay System (Prophetic)

Detection of the binding of βTRCP to a phosphopeptide derived from IkBa. In order to demonstrate the detection of binding species produced by an in vitro translation system using bead based systems, we use the well known binding interaction between a phosphopeptide of IkBa, H2N-LK-KERLLDDRHDS(p)GLDS(p)MKDEEYE (SEQ ID NO: 1) and the protein βTRCP.

The following peptides are synthesized.

```
IkB20-bio,  H2N-LKKERLLDDRHDSGLDSMKDEEYEC-biotin        (biotinylated (SEQ ID NO: 2))
IkB20-p-bio,H2N-LKKERLLDDRHDS(p)GLDS(p)MKDEEYEC-biotin.  (biotinylated (SEQ ID NO: 1))
```

These peptides are immobilized on to Dynal M280 beads coated with streptavidin making use of the well known streptavidin biotin interaction. The peptide is dissolved in PBS, 0.1% NP40 and incubated with the beads for 1 hour followed by 4 washes into binding buffer (50 mM Tris-HCL pH7.5, 300 mM NaCl, 2 mM EDTA, 0.1% NP40 and protease inhibitor cocktail (Roche)).

The TnT reaction are carried out following the manufactures protocol. The reaction is was as follows, 25 μl of lysate (coupled TnT, Promega, Madison Wis.), 0.5 μg of plasmid DNA. The plasmid DNA contains the βTRCP gene fused in frame with the Flag epitope and contains a RNA polymerase site. A plasmid vector directing transcription of flag-βTRCP gene fusion is constructed using synthetic PCR primers to the EST clone IMAGE # 3491843. The primers

```
TATGTCGACATGGATTATAAGGATGACGATGACAAAGACCCGGCAGAGGCGGTGCTG and(SEQ ID NO: 13)
TATGCGGCCGCTTATCTGGAGATGTAGGTGTA                             (SEQ ID NO: 14)
```

are used to generate the flag-βTRCP gene fragment of about 1750 bases. This PCR DNA product is then subject to restriction digestion with Sal1 and Not1 following the manufactures protocol (New England Biolabs, Beverly, Mass.). The cut PCR DNA product is gel purified and ligated into Sal1 and Not1 cut pCMV-SPORT6 (Invitrogen, Carlsbad, Calif.). The ligation is transformed into *E. coli* and the clones screened for the correct insert.

One of the resulting clones is used in the TnT reaction to produce the fusion protein Flag-βTRCP. Protein expression in the TnT reaction is confirmed using radioactive Met following the manufactures protocol (Promega, Madison, Wis.). To determine if we can detect the binding of flag-βTRCP to the phosphopeptide we incubate the products of the TnT reaction specific for the flag-βTRCP with beads coated with the consensus phosphopeptide or the control peptide. These beads are washed and ORI-TAG® (IGEN International, Inc., Gaithersburg, Md.) labeled anti Flag antibody is added in binding buffer and then incubated followed by analysis in an ORIGEN M8 (IGEN International, Inc., Gaithersburg, Md.). The results of this study demonstrate a strong signal from the flag-βTRCP binding to the phosphopeptide but not to the control no phosphorylated sequence produced in the TnT system. This strong signal is reflected in a high signal to noise ratio (as calculated using the signals obtained from translation mixtures having no exogenous DNA, unrelated clones or control peptide).

Example 15

Assay for DNA Binding Proteins Produced in a Tnt Reaction (Prophetic)

In this assay cDNA clones are subjected to a TnT reaction followed by the detection of those proteins that are able to bind specifically to a given nucleic acid sequence. The following EST clones coding for the YY1 transcription factor are tested: IMAGE IDs, 3987868, 3156776, 2655378, and 3859359 (Incyte Genomics). For a control, the luciferase plasmid included in the TnT kit from Promega is used. DNA is prepared from these clones using the Qiagen miniprep kit (Qiagen, Los Angeles, Calif.).

The oligo specific for YY1 is made synthetically (IGEN International, Inc., Gaithersburg, Md.) using the following sequences 5'ORI-tag-labeled-

*ACGTACGTACC*GCTCCGCGGCCATCTTGGCGGCTGGT and its complement (SEQ ID NO: 15)

5'ACCAGCCGCCAAGATGGCCGCGGAGCGGTACGTACGT. (SEQ ID NO: 16)

These two oligonucleotides are annealed by mixing together equimolar amounts in 10 mM Tris-HCL pH 7.9, 1 mM EDTA, 50 mM KCl. This double stranded oligonucleotide (ECL-oligo) is then used in the following DNA binding assay.

The YY1 protein and the control luciferase are produced in a coupled TnT reaction, as described in the Materials and Methods. Then 5 μl of the reaction product is mixed with, 50 μl of binding buffer and 28–14 ng/ml 5'ORI-tag-labeled double stranded oligonucleotide produced above, in a streptavidin-coated NPT IPR plate (see examples above). The plate is left on a tabletop shaker for 1 hour to allow for biotinylated proteins to bind to the surface of the plate and for the ECL-oligo to bind to the biotinylated proteins. Thereafter the plate is washed three times with PBS followed by the addition of 100 μl of ORIGEN assay buffer (IGEN International, Inc., Gaithersburg, Md.) into each well, and ECL signals are measured. The ECL signals are measured using an imaging plate reader (IPR). In a typical assay the presence of YY1 encoding plasmid is expected to produce a greater than 2 fold higher ECL signal compared to the luciferase control vector demonstrating the specific binding of the DNA sequence to the YY1 protein.

Example 16

Assay for DNA Binding Proteins, Using a Multi-Spot™ Approach (Prophetic)

Assay for DNA proteins produced by an in vitro translation system to DNA targets arrayed on multiple spots in a single well.

Four DNA oligos and their binding proteins (Table 21) are selected for an assay of multiple DNA-protein interaction in 4-spot multi-array IPR plates. The EST clones for c-jun IMAGE ID # 3606344, 4053956, 4446852, 3912000, 4182406, 3493248, 3968444, 4018781; the Glucocorticoid Receptor IMAGE ID #4036433, 3584269; the p53 protein IMAGE ID # 4508539, 4384628, 4524419, 3599812, 3966816, 4503010; and the CCAAT displacement protein (CDP) IMAGE ID # 4516029, 4420011, 4385939 are ordered from Incyte genomics (Palo Alto, Calif.).

TABLE 21

List of DNA and their binding proteins

| DNA oligo | Binding protein | Sequence | |
|---|---|---|---|
| AP-1 | c-jun | 5'SH-X-ACTGACTGACcgcttgatgactcagccggaa | (SEQ ID NO: 17) |
| Gluc | Glucocorticoid Receptor | 5'SH-X-ACTGACTGACgaccctagaggatctgtacaggatgttctagat | (SEQ ID NO: 18) |
| P53 | p53 | 5'SH-X-ACTGACTGACtacagaacatgtctaagcatgctggggact | (SEQ ID NO: 19) |
| CDP | CDP | 5'SH-X-ACTGACTGACacccaatgattattagccaatttctga | (SEQ ID NO: 23) |

The DNA sequences listed in Table 21 are synthesized as well as the complementary sequences without 5' modifications. These oligos are rendered double stranded using the method described above by mixing the complementary pairs together. The SH-X-group at the 5' end of the oligonucleotide sequence is introduced during synthesis using a cycle of Spacer Phosphoramidite 18 (Catalog Number: 10-1918-xx Glenn Research, Herndon, Va.) followed by a cycle of Thiol-Modifier C6 S—S (Catalog Number: 10-1936-xx Glenn Research, Herndon, Va.) during synthesis. This results in a 5' free SH group attached to a hexaethyleneglycol spacer ready for coupling.

The SH-X-moiety at the 5' terminus is added to the sequence to allow for covalent coupling of the DNA to a carrier protein. A maleimide pre-activated BSA (Pierce, Pittsburgh Pa.) is used as the protein carrier. The protein contains about 17 active maleimide groups on the protein surface and is supplied as lyophilized preparation. The coupling reaction is carried out with 2 mg BSA (30 nmol) and different molar amount of the DNA in 400 μl PBS. The molar ratio of DNA relative to the BSA is between 4:1 to 17:1. The reaction is terminated with 2 mM L-cystine after incubation at room temperature for 30 minutes. The DNA:BSA conjugate is then purified by gel filtration to remove uncoupled DNA and analyzed with SDS PAGE to monitor the coupling reaction. After coupling and purification, the column fractions containing the DNA:BSA conjugates are pooled and the protein concentration of the pooled samples is determined by BCA assay (Pierce, Pittsburgh Pa.). NaN3, (0.02%) is added to the final peptide;BSA conjugate sample for long term storage at 4° C.

To prepare the multi spot IPR plates, approximately 2.4 pmol to 1.2 pmole DNA-BSA conjugates in 2.5 μl are deposited on carbon surface in a single well of a 96-well plate using a Bio-Dot dispenser. At this stage, the plates are dried then used or stored under desiccated condition. A few hours prior to usage, the plates are rehydrated and blocked with 3% BSA, in PBS.

DNA for the EST clones encoding c-jun, glucocorticoid receptor, p53 and CDP are isolated using QIA-prep column (QIAGEN, Los Angeles, Calif.). These DNA molecules are used to produce the proteins in a Quick coupled SP6 in vitro transcription and translation (TnT) reaction (Promega, Milwaukee, Wis.) as described in Materials and Methods. The proteins are transferred to a well of the 4 spot DNA:BSA coated and BSA blocked IPR plates. To these wells 50 to 100 ng/well of Sulfo-TAG labeled Streptavidin (see example 2) is added as the detection agent. The binding reaction can be carried out in cold room for over two hours or at room temperature for 1 hour without significant difference. After binding, the IPR plates are washed twice with PBS and 100 μl of ORIGEN Assay Buffer (Cat. # 110006, IGEN International, Inc., Gaithersburg, Md.) is added to each well before reading the ECL signal. The ECL signals are measured using an imaging plate reader (IPR).

The results demonstrate the potential of the multiple binding domains (4 spots) in a single well to increase both the speed and specificity of screens for binding interactions. This method also provides for significant savings of reagents in a screen with 4 differing binding species.

Example 17

ECL Based Assays for DNA and Protein Interaction (Prophetic)

Assay using Multiple DNA Oligos for Protein Interactions in a single well. DNA synthesis. The following oligonucleotide and their complement (with out 5' modifications) are chemically synthesized (Midland certified reagent company, Midland Tex.). Table 22 lists the oligonucleotides and their expected protein binding partners.

```
AP1,5'SH-X-ACTGACTGACcgcttgatgactcagccggaa            (SEQ ID NO: 17)

Gluc,5'SH-X-ACTGACTGACgaccctagaggatctgtacaggatgttctagat (SEQ ID NO: 18)

P53,5'SH-X-ACTGACTGACtacagaacatgtctaagcatgctggggact     (SEQ ID NO: 19)

YY1,5'SH-X-ACGTACGTACcgCTCCGCGGCCATCTTGGCGGCTGGT        (SEQ ID NO: 20)

C/EBP,5'SH-X-ACTGACTGACtgcagattgcgcaatctgca            (SEQ ID NO: 21)

HNF,5'SH-X-ACTGACTGACatctaggtcaaaggtcatact             (SEQ ID NO: 22)
```

TABLE 22

| DNA | SEQ ID NOs | Binding Partner |
|---|---|---|
| Ap1 | (SEQ ID NO: 17) | c-jun |
| Gluc | (SEQ ID NO: 18) | Glucocortcoid receptor |
| p53 | (SEQ ID NO: 19) | p53 |
| YY1 | (SEQ ID NO: 20) | YY1 transcription factor |
| C/EBP | (SEQ ID NO: 21) | CCAAT enhancer binding protein gamma |
| HNF | (SEQ ID NO: 22) | HNF-4 |

The SH residues at the terminus are added to the sequence to allow for covalent coupling of the DNA to a carrier protein as described in Example 16.

To prepare the multi spot IPR plates, in this example we make use of pools of the DNA:BSA conjugates to coat each of 4 spots per well in a 96 well plate. To achieve this we make the following pools.

Pool A; Ap1, Glue and P53

Pool B; Ap1, YY1 and C/EBP

Pool C; P53, YY1 and HNF

Pool D; Glue, HNF and C/EBP

In an alternative method the conjugation reaction to BSA is carried out with a pool of the oligos to give rise to a mixed conjugate that achieves the same effect of combining the various oligos into a pool.

This combination of the various DNA:BSA conjugates results in a single DNA conjugate being present in two pools and any pair of pools contains only one DNA conjugate in common. This allows the determination of the specific DNA binding partner based on the two spots that produce signal. Each of these four pools is then spotted on to a unique spot in a 4 spot array such that each pool. In this way any single specific binding protein would bind to two spots which allows the determination of the specific DNA oligo involved by determination of the specific pools a given protein bound to. The pair of pools that a given protein binds to defines a code that determines which specific oligonucleotide was responsible for mediating the binding. The coding resulting from the pools described above is shown in Table 23

TABLE 23

| DNA:BSA conjugate | SEQ ID NOs | Pool Code |
|---|---|---|
| C/EBP | (SEQ ID NO: 21) | B, D |
| HNF | (SEQ ID NO: 22) | C, D |
| Ap1 | (SEQ ID NO: 20) | A, B |
| P53 | (SEQ ID NO: 19) | A, C |
| Gluc | (SEQ ID NO: 18) | A, D |
| YY1 | (SEQ ID NO: 17) | B, C |

Approximately 120 fmole of DNA:BSA conjugate in 0.25 μl is deposited on each spot of a 4-spot multi-array IPR plates using BioDot (Irvine Calif.). At this stage, the plates are dried then used or stored under desiccated condition. A few hours prior to usage, the plates are rehydrated and blocked with 3% BSA, in PBS.

To test the system the following EST clones for c-jun IMAGE ID # 4446852, 3912000, 4182406, 3493248, 3968444, 4018781; the Glucocorticoid Receptor IMAGE ID #4036433, 3584269; the p53 protein IMAGE ID # 4508539, 4384628, 4524419, 3599812, 3966816, 4503010; the C/EBP gamma protein IMAGE ID # 3445301, 4368690, 3898882, 3709074, 4010465; and the HNF-4 protein IMAGE ID # 4238842, are purchased from Incyte genomics (Palo Alto, Calif.). Plasmid DNAs from these various clones are prepared using the Qiagen miniprep kit (Qiagen, Los Angeles, Calif.). These DNAs are used to produce the proteins as described in the Materials and Methods and the each protein is transferred to a separate well of the 4 spot DNA:BSA coated and BSA blocked ECL plates. To these wells 50 to 100 ng/well of Sulfo-TAG labeled Streptavidin (see example 2) is added as the detection agent. The binding reaction can be carried out in cold room for over two hours or at room temperature for 1 hour without significant difference. After binding, the ECL plates are washed twice with PBS and 100 μl of ORIGEN Assay Buffer (Cat. # 110006, IGEN International, Inc., Gaithersburg, Md.) is added to each well before reading the ECL signal. The ECL signals are measured using an imaging plate reader (IPR).

Most of the of the clones produce the expected coded binding response as predicted below:

c-jun IMAGE ID # 4446852, 3912000, 4182406, 3493248, 3968444, 4018781; give binding code A, B;

Glucocorticoid Receptor IMAGE ID #4036433, 3584269; give binding code A, D;

p53 protein IMAGE ID # 4508539, 4384628, 4524419, 3599812, 3966816, 4503010; give binding code A, C;

C/EBP gamma protein IMAGE ID # 3445301, 4368690, 3898882, 3709074, 4010465; give binding code B, D;

HNF-4 protein IMAGE ID # 4238842 give binding code C, D.

These results demonstrate the potential of this method of pooling DNA in combination with multiple spots to improve the screening of large numbers of binding species immobilized on to a solid phase.

Example 18

Assay for Peptide Binding Proteins Produced in a Tnt Reaction, Using a Labeled Peptide (Prophetic)

Assay for the Binding Activity of βTRCP to a Peptide Derived from IkBa.

The peptide from IkBa, H2N-LKKERLLDDRHDS(p) GLDS(p)MKDEEYEC (SEQ ID NO: 1) is synthesized chemically. The ECL label is coupled post synthesis using ORI-TAG-Maleimide (IGEN International, Inc., Gaithersburg Md.) to produce the following peptide H2N-LKKERLLDDRHDS(p)GLDS(p)MKDEEYEC-ORI-TAG. The following clones for testing are obtained from Incyte (CA) βTRCP1 IMAGE ID #3491843; βTRCP2 IMAGE ID #4237375; Grb2 IMAGE ID #4398016; PLCγ IMAGE ID #4419252. These clones are grown up and DNA prepared using the Qiagen miniprep kit (Qiagen, Los Angeles, Calif.). These DNAs are used to produce the proteins in the transcription and translation reaction as described in the Materials and Methods.

The reaction products are added to separate wells of an IPR plate coated with streptavidin and combined with 10–100 ng/ml of ORI-TAG labeled peptide. The plate is left on a tabletop shaker for 1 hour to allow for biotinylated proteins to bind to the surface of the plate and for the ORI-TAG labeled peptide to bind to biotinylated proteins. Thereafter the plate is washed three times with PBS followed by addition of 100 μl of ORIGEN Assay Buffer (IGEN International, Inc., Gaithersburg, Md.) into each well, and ECL signals are measured in IPR Analyzer. The results demonstrate specific signal, above that of the control clones, for the clones able to direct the transcription and translation of the bTRCP binding proteins (3491843 and 4237375).

Example 19

Assay for the Detection of Proteins Binding to Non-Peptide Small Molecule Binding Partners Assay for Detecting the Binding of Glucocortcoid Receptor and Progesterone Receptor to Labeled Steroids Cortisol and Progesterone Respectively. The following ECL labeled steroids are purchased from IGEN International, Inc. (Gaithersburg, Md., these are part of Roche Diagnostic Kits): Estradiol (2.75 ng/ml), Progesterone (10 ng/ml), Testosterone (3 ng/ml), Cortisol (25 ng/ml). These steroids are labeled via a peptide linker attached to the steroid. The following clones for testing are obtained from Incyte (CA) Glucocortcoid receptor IMAGE ID # 4036433, 3584269; progesterone binding proteins IMAGE ID # 4449225, 4365385; and the control clones bTRCP1 IMAGE ID #3491843; bTRCP2 IMAGE ID #4237375;. These clones are grown up and DNA prepared using the Qiagen miniprep kit (Qiagen, Los Angeles, Calif.). These DNAs are used to produce the proteins as described in Example 7 and mixed with 1–10 ng/ml ORI-TAG-labeled steroid in IPR plate coated with streptavidin. The plate is left on a tabletop shaker for 1 hour to allow for biotinylated proteins to bind to the surface of the plate and for the ORI-TAG-labeled peptide to bind to biotinylated proteins. Thereafter the plate is washed three times with PBS followed by addition of 100 μl of ORIGEN Assay Buffer (IGEN International, Inc., Gaithersburg Md.) into each well, and ECL signals are measured. The ECL signals are measured using an imaging plate reader (IPR). The results demonstrate specific signal above that of the control clones for the clones able to direct the transcription and translation of the steroid receptors. In addition, no specific signal is associated with related ECL labeled steroids that were not bound by the specific steroid receptors.

Example 20

Protein:Protein Binding Assay (Prophetic)

Assay for Detecting the Binding of fos and jun.

The Sulfo-TAG labeled anti-BODIPY®FL antibody (Molecular Probes, CA) was produced and purified as described in Materials and Methods. The antibody is stored in 25 mM TRIS-HCl pH 7.5, 0.05% sodium azide. The following clones for testing are obtained from Incyte (CA) mouse fos IMAGE ID #, 3583544, 4457761, 3586465; human fos IMAGE ID # 3688670; mouse jun IMAGE ID # 3493248, 3968444, 4018781; human Jun IMAGE ID # 3606344, 4053956, 4446852, 3912000, 4182406; and the control clones bTRCP1 IMAGE ID #3491843; bTRCP2 IMAGE ID #4237375;. These clones are grown up and DNA prepared using the Qiagen miniprep kit (Qiagen, Los Angeles, Calif.). These DNAs are used to produce the proteins encoded by the various cloned DNAs in the following transcription and translation reaction. These clones are transcribed and translated in two reactions one with biotin-lys-tRNA and one with FluoroTect™Green(BODIPY®FL)-Lys-tRNA to generate a copy of each protein encoded by these clones labeled with biotin and a copy labeled with BODIPY®FL.

Transcription-translation reaction mixtures described in Materials and Methods were used to produce protein. Following these TnT reactions a sample from each clone from the biotin tRNA reaction is mixed with a sample from each clone from the FluoroTect™Green-Lys-tRNA reaction as follows: Then 4–8 μl of the biotin-lys-tRNA TnT reaction and 4–8 ul of the FluoroTect™Green-Lys-tRNA TnT reaction is mixed with 50 μl of binding buffer (PBS, pH7.4, 0.1%BSA, 0.1% bovine IgG, 0.2% tween-20, and protease inhibitor tablets without EDTA (Roche)), and 50 ng Sulfo-TAG labeled anti-BODIPY®FL antibody in a IPR plate coated with streptavidin. This combination of the clones results in a set of incubations where each clone is allowed to bind to each of the other clones and also to its self from a complementary reaction with an alternatively modified tRNA. Following this set up the plate is left on a tabletop shaker for 1 hour to allow for biotinylated proteins to bind to the surface of the plate and for the Sulfo-TAG labeled antibody to bind to the BODIPY®FL labeled proteins. Thereafter the plate is washed three times with PBS followed by addition of 100 μl of ORIGEN Assay Buffer (IGEN International, Inc., Gaithersburg Md.) into each well, and ECL signals are measured. The ECL signals are measured using an imaging plate reader (IPR). The results demonstrate specific signal above that of the control clones for the clones able to direct the transcription and translation of the proteins known to bind to each other.

Example 21

Protein:Protein Binding Assay (Prophetic)

Assay for Detecting the Binding of Myc and Max and p53 and T Antigen.

The following clones for testing are obtained pGBKT7-53, pGADT7-T, pGBKT7-c-Myc, pGADT7-Max and the control clones, pGBKT7, pGADT7 pGBKT7-lam (Clontech, Palo Alto Calif.). These clones were grown up and DNA prepared using the Qiagen miniprep kit (Qiagen, Los Angeles, Calif.). These DNAs are used to produce the proteins encoded by the various cloned DNAs in the following transcription and translation reaction. Each of these clones are transcribed and translated, as described in Materials and Methods, in two reactions: one supplemented with biotin-lys-tRNA and one under normal conditions to generate a copy of each protein encoded by these clones labeled with biotin or unlabeled.

Following the TnT reactions a sample from each clone from the biotin tRNA reaction is mixed with a sample from each clone from the standard TnT reaction as follows: 4–8 μl of the biotin-lys-tRNA TnT reaction and 4–8 μl of the standard TnT reaction is mixed with 50 μl of binding buffer (PBS, pH7.4, 0.1%BSA, 0.1% bovine IgG, 0.2% tween-20, and protease inhibitor tablets without EDTA (Roche)), and 50 to 100 ng/well of Sulfo-TAG labeled Streptavidin (see Materials and Methods) in NPT IPR plate coated with anti HA epitope antibody F-7 (Santa Cruz, Calif.). In a duplicate experiment the same set of sample mixes are added to an NPT IPR plate coated with anti Myc epitope antibody 9E10 (Sigma). This combination of the clones results in a set of incubations where each clone is allowed to bind to each of the other clones in a pair wise fashion and also to its self from a complementary reaction without a modified tRNA. Following this set up the plate is left on a tabletop shaker for 1 hour to allow the proteins to bind specifically to the antibody coated surface of the plate and for the biotinylated proteins to bind to Sulfo-TAG labeled streptavidin. Thereafter the plate is washed three times with PBS followed by addition of 100 μl of ORIGEN Assay Buffer (IGEN International, Inc., Gaithersburg, Md.) into each well, and ECL signals are measured in the IPR Analyzer to determine which proteins are binding resulting in ECL signals over that seen with the control clones pGBKT7, pGADT7 pGBKT7-lam.

The results demonstrate specific signal for the binding of p53 (pGBKT7-53) to T antigen (pGADT7-T). This p53-T antigen binding is demonstrated with a specific signal on the anti-myc coated IPR plate with the mix from these TnT reactions; pGBKT7-53 normal TnT with pGADT7-T biotin-lys-tRNA TnT. With the anti-HA coated IPR plate the specific signal is seen with the mix from these TnT reactions; pGADT7-T in a normal TnT with pGBKT7-53 in a biotin-lys-tRNA TnT.

The results also show the binding of Myc (pGBKT7-c-Myc) to Max (pGADT7-Max). This Myc to Max binding is demonstrated with a specific signal on the anti-myc coated IPR plate with the mix from these TnT reactions; pGBKT7-c-Myc normal TnT with pGADT7-Max biotin-lys-tRNA TnT. With the anti-HA coated IPR plate the specific signal is seen with the mix from these TnT reactions; pGADT7-Max in a normal TnT with pGBKT7-c-Myc in a biotin-lys-tRNA TnT.

Example 22

Assay to Detect and Identify Antigens Recognized by Antibodies

In order to demonstrate the detection and identification of antigens produced by an in vitro translation system using antibodies we use the antibodies from the serum of patients with the auto-immune disease, Sjogren syndrome.

The following patient serum samples are obtained: samples 1–5 from patients diagnosed with Sjogren syndrome, samples 6–10 from control normal patients (patients without Sjogren syndrome). Rabbit anti human antibodies (Rockland) are labeled with Sulfo-TAG-NHS and purified as described in Materials and Methods. The following clones are purchased IMAGE ID #, 4395342, 3922229, 3904700, 3459939, 3047963, 3857068, 4342257, 3454454, 3910607, 4237375 and 3491843 (Incyte, Palo Alto, Calif.). These clones are grown in 2 ml LB with 50 μg/ml Amp, and DNA is isolated using QIAprep Spin Miniprep Kit (Qiagen). DNA yield is 5–20 μg.

The clones are as follows;

Sjogren syndrome antigen A2 (60 kD, ribonucleoprotein autoantigen SS-A/Ro), 4395342;

Sjogren syndrome antigen A1 (52 kD, ribonucleoprotein autoantigen SS-A/Ro), 3922229, 3904700;

Sjogren's syndrome nuclear autoantigen 1, 3459939, 3047963;

Sjogren's syndrome/scleroderma autoantigen 1, 3857068, 4342257;

Sjogren syndrome antigen B (autoantigen La), 3454454, 3910607;

βTRCP1, 3491843;

βTRCP2, 4237375.

The DNA from these clones is translated in a transcription and translation system as described in Materials and Methods. Then 5 μl of the reaction product is mixed with 50 μl of binding buffer in a well of a 96 well NPT IPR plate coated with streptavidin. In this way 2, 96 well plates are generated with 5 rows A, B, C, D, E containing the 11 clones in each of these rows, one clone in each well with the 12th well in each row as a control well (no protein) in combination with the two βTRCP clones, as control proteins. The plate is left on a tabletop shaker for 1 hour to allow for the biotinylated proteins from the transcription translation reaction to bind to the surface of the plate. Thereafter the plate is washed three times with PBS.

Then patient samples 1–10 are diluted into PBS, pH7.4, 0.3%BSA, 0.2% tween-20 to generate dilutions from 1/200 to 1/2,000 these diluted patient samples are then added 50 μl per well in such a way that each patient sample is added to a row on the 96 well plate with the 11 clones coated on to the surface. These plates are then left on a tabletop shaker for 1 hour to allow for the patient antibodies to bind to the proteins coated on the plate. Thereafter the plate is washed three times with PBS. To these washed plates 50 μl of PBS, pH7.4, 0.3%BSA, 0.2% tween-20, 60 mg/ml Sulfo-TAG labeled anti-human antibody is added followed by incubation with shaking for 1 h. Thereafter the plate is washed three times with PBS followed by addition of 100 μl of ORIGEN Assay Buffer (IGEN International, Inc., Gaithersburg, Md.) into each well, and ECL signals are measured. The ECL signals were measured using an imaging plate reader (IPR).

The results demonstrate that the patient samples 1–5 contain antibodies to the Sjogren syndrome antigens produced and coated on to 96 well plates, where as the normal patients 6–10 who did not have Sjogren syndrome did not. This demonstrates the value of this method for the discovery and identification of antigens recognized by antibodies especially from complex mixtures of antibodies such as autoantibodies in patient samples.

Example 23

Demonstration of a Multiwell Screening Method for Multiple Clones; Screen of 90 EST Clones in 96-Well Format The example demonstrates a screen to identify (i) substrates of ubiquitylation in reticulocyte lysates; (ii) proteins binding to specific phosphopeptides; and (iii) proteins possessing tyrosine-kinase activities.

A. Preparation of Plasmid DNA

90 Bacterial clones containing different EST cDNAs were grown in 1.3 ml LB with 100 μg/ml Amp, and DNA was isolated using QIAprep 96 turbo Miniprep Kit (Qiagen) in 96-well format. DNA yield was, typically, 5–50 μg. Seven of these clones produced less than 5 μg DNA. Mean DNA concentration was 470 μg/ml. The clone IMAGE ID # were as follows; 3870426, 3893964, 3919253, 3491843, 4237375, 4398016, 4419252, 3907115, 2899921, 2900118, 2900273, 2900421, 2900551, 2900956, 2901296, 3048141, 3048356, 3048606, 3445488, 3446518, 3446546, 3449836, 3449955, 3450936, 3451168, 3452024, 3452494, 3452714, 3453890, 3454025, 3454207, 3454505, 3454625, 3455258, 3455871

3458308, 3458973, 3459189, 3459274, 3460054, 3460621, 3461825, 3462090, 3462906, 3463478, 3463640, 3464547, 4181547, 3845821, 3847788, 3853408, 3857590, 3857760, 3859672, 3862264, 3866131, 3868632, 3868989, 3872315, 3877854, 3886015, 3886018, 3886999, 3894925, 3897353, 3898275, 3901471, 3901641, 3902385, 3906095, 3906517 3907984, 3908004, 3908182, 3908412, 3910505, 3912185, 3912628, 3914731, 3915089, 3919253, 3920860, 3921259, 3923156, 4343428, 3911953, 3909654, 3913291, 3914467, 3909921, 4191647 (Incyte Genomics, Palo Alto Calif.).

In addition, four clones were purified separately using Qiagen Midiprep kit and introduced into the 96-well plate at 470 μg/ml in addition to the rest of the clones to serve as positive controls in the assays. Two of these control clones (IMAGE IDs 3920860, 3912628) contained full-length RGS4 cDNA, a known substrate of ubiquitylation (Examples 1, 2, 3, 4, 5, 6) and the remaining two clones (IMAGE ID 3491843 and 4237375) encode for βTRCP1 and βTRCP2 respectively, proteins known to bind to a phosphorylated peptide derived from IkBa (Examples 10, 11, 12). These 4 clones were introduced into the wells of the 96 well plate in row H, positions H9, H10, H11, H12. The DNA samples were arranged on the 96 well plate as shown in Tables 24 and 25.

TABLE 24

| | 1 | 2 | 3 | 4 | 5 | 6 |
|---|---|---|---|---|---|---|
| A | 3870426 | 3893964 | 3919253 | 3491843 | 4237375 | 4398016 |
| B | 2900421 | 2900551 | 2900956 | 2901296 | 3048141 | 3048356 |
| C | 3450936 | 3451168 | 3452024 | 3452494 | 3452714 | 3453890 |
| D | 3458308 | 3458973 | 3459189 | 3459274 | 3460054 | 3460621 |
| E | 4181547 | 3845821 | 3847788 | 3853408 | 3857590 | 3857760 |

TABLE 24-continued

| | 1 | 2 | 3 | 4 | 5 | 6 |
|---|---|---|---|---|---|---|
| F | 3877854 | 3886015 | 3886018 | 3886999 | 3894925 | 3897353 |
| G | 3907984 | 3908004 | 3908182 | 3908412 | 3910505 | 3912185 |
| H | 3923156 | 4343428 | 3911953 | 3909654 | 3913291 | 3914467 |

TABLE 25

| | 7 | 8 | 9 | 10 | 11 | 12 |
|---|---|---|---|---|---|---|
| A | 4419252 | 3907115 | No Clone | 2899921 | 2900118 | 2900273 |
| B | 3048606 | 3445488 | 3446518 | 3446546 | 3449836 | 3449955 |
| C | 3454025 | 3454207 | 3454505 | 3454625 | 3455258 | 3455871 |
| D | 3461825 | 3462090 | 3462906 | 3463478 | 3463640 | 3464547 |
| E | 3859672 | 3862264 | 3866131 | 3868632 | 3868989 | 3872315 |
| F | 3898275 | 3901471 | 3901641 | 3902385 | 3906095 | 3906517 |
| G | 3912628 | 3914731 | 3915089 | 3919253 | 3920860 | 3921259 |
| H | 3909921 | 4191647 | 3920860 | 3912628 | 3491843 | 4237375 |

B. Transcription-Translation Reactions

Transcription-translation reactions were assembled in a 96-well plate as described in Materials and Method in a total volume of 19 μl. The amounts of DNA in each reaction varied depending on DNA yields at purification stage, while the four positive control wells contained reactions with 20 μg/ml plasmid DNA. The reactions were incubated at 30° C. for 40 min.

C. Ubiquitylation Assay

After incubation, 1 μl of the TNT reaction was mixed with 50 μl of BB1 in an IPR plate coated with FK2 antibody (750 ng antibody per well) (see Materials and Methods). The plate was left on a tabletop shaker for 1 hour to allow for ubiquitylated proteins to bind to the surface of the plate and for the Sulfo-TAG labeled streptavidin to bind to biotinylated proteins. Thereafter the plate was washed three times with PBS followed by addition of 100 μl of ORIGEN Assay Buffer (IGEN International, Inc., Gaithersburg, Md.) into each well, and ECL signals were measured.

FIG. 2 shows that three RGS4-encoding IMAGE clones (3912628, 3914731, and 3920860) produced strong specific signal in this assay (◇) comparable to the signal produced by the two control RGS4 clones (□). The rest of the 88 EST clones analyzed in this experiment produced much weaker signals (♦). The assay was able to identify RGS4 as an efficient substrate of ubiquitylation in reticulocyte lysates, as previously reported (Davydov and Varshavsky, 2000, *J. Biol. Chem.*, 275:22931–22941).

D. Screen for Phosphopeptide Binding Proteins

A screen was conducted using 7-spot IPR plates. The 7 spot NPT IPR plates are described in more detail in copending Provisional Application No. 60/301,932 (entitled "Assay Plates, Reader Systems and Methods for Luminescence Test Measurements", filed on Jun. 29, 2001, hereby incorporated by reference) and particularly in the description of Plate Type D in Example 6.1 (NPT IPR plate) and U.S. application Ser. Nos. 10/185,274 and 10/185,363, filed Jun. 28, 2002, each hereby incorporated by reference. These plates consist of a 96 wells with 7 zones (spots) for the immobilization of proteins or other reagents. Each spot was coated with BSA conjugated to either a single phosphopeptide or multiple phosphopeptides. The peptides used in the study are shown in Table 26

TABLE 26

| Peptide name | Binding protein | Sequence | |
|---|---|---|---|
| PY992 | PLCγ | DADE(p)YLIPQQGFFSSPSTSC | (SEQ ID NO: 5) |
| PY1068 | Grb2, PLCγ | LPVPE(p)YINQSVPKRPAGSVC | (SEQ ID NO: 7) |
| PY1148 | Shc | KGSHQISLDNPD(p)YQQDFFPKEAKPNC | (SEQ ID NO: 9) |
| IkB | βTRCP | LKKERLLDDRHD(p)SGLD(p)SMKDEEYC | (SEQ ID NO:1) |
| Myc | Unknown | CPSEDIWKKFELLP(p)TPPL(p)SPSRRSGL | (SEQ ID NO: 4) |
| Smad3C | Unknown | CGPLQWLDKVLTQMGSPHNPIS(p)SV(p)S | (SEQ ID NO: 11) |

The plates were prepared essentially as described in example 12. The seven spots supported, respectively, the following BSA conjugates IkB, pY992, pY1068, pY1148, Myc, "A", and "6-P". "A" refers to a conjugate of BSA with multiple peptides: IkB, pY1148, Myc which were then coupled to BSA. "6-P" refers to a conjugate of BSA with the following multiple peptides: IkB, pY1148, pY992, pY1068, Smad3C.

For the assay, 4 ul from TnT reaction product described above were added to the coated plate containing 50 μl of binding buffer supplemented with 50 ng/well Ru-Streptavidin. The binding reaction was allowed to proceed at room temperature for 1 hour with constant shaking. At the end of incubation, the plate was washed twice with PBS and 100 μl of Origen Assay Buffer (IGEN International, Inc., Gaithersburg Md.) was added for reading the ECL. The ECL signals were measured using an imaging plate reader (IPR). The raw data from the IPR reader was then normalized using two steps of normalization. The first round was based on the 50 lowest values for a given specific spot. These 50 lowest values were averaged and divided into each signal for that spot to generate a signal value which could be compared readily between the peptide-conjugate spots. This was then followed by a second round of normalization using the lowest normalized value for a spot within a well to divide the signals from the other spots. This method provides a means to reduce the signals from proteins which bound non specifically to all the spots within a well. Following this the data was sorted for the highest signals for each of the spots to determine the rank order of the hits from each of the 7 peptide spots produced in the 96 well plate.

The results below demonstrate the expected correlation between the specific peptide and its binding partner demonstrating the value of this approach for the screening of libraries of clones for specific binding partners using a multi well plate with multiple binding domains (spots). The results from the multiple peptide spots ("A" and "6-P") agreed with the single peptide spots demonstrating the value of pooling peptides to increase the number of peptides per screen.

The Myc Peptide Showed Binding to the F-Box Protein βTRCP Indicating that it Might be Modulated Via Ubiquitination as IkBa is on its Phosphorylation.

The results from the screen were as expected. The results for the top 9 clones for each of the single peptide spots are shown below. The data from the multiple peptide spots also agreed with this data. This approach with multiple spots readily allowed us to normalize the background within a well which prove valuable with some clones that had high background binding to all the peptide spots in the well.

In the case of the IkB peptide (SEQ ID NO: 1), the data is shown in Table 27, the controls of βTRCP (4237375, 3491843) gave the highest signals followed by the two clones which were grown up in the 96 well format (3491843, 4237375) which are the two βTRCP clones. The clone 3445488 was not considered a hit as it produced high background on a number of the peptide spots which was not fully corrected with this normalization protocol.

TABLE 27

| | | IkBa |
|---|---|---|
| βTRCP [c] | 4237375 | 38 |
| βTRCP [c] | 3491843 | 23 |
| βTRCP | 3491843 | 12 |
| | 3445488 | 7 |
| βTRCP | 4237375 | 3 |
| | 3886018 | 2 |
| | 3452714 | 2 |
| | 3915089 | 2 |
| | 3463640 | 2 |

The results in the case of the pY1148 (SEQ ID NO: 9) (Table 28) were as expected with the four Shc clones and PLCg giving the highest signals. The top 9 clones are listed below.

TABLE 28

| | | pY1148 |
|---|---|---|
| Shc | 3909921 | 5 |
| PLCγ | 4419252 | 4 |
| Shc | 3911953 | 3 |
| Shc | 3909654 | 3 |
| Shc | 3914467 | 3 |
| | 3445488 | 2 |
| | 4237375 | 1 |
| | 3491843 | 1 |
| | 3491843 | 1 |

The results with the pY992 peptide (SEQ ID NO: 5) (Table 29) were also as expected with the PLCγ clone showing the highest signal.

TABLE 29

| | | pY992 |
|---|---|---|
| PLCγ | 4419252 | 10 |
| | 3909921 | 1 |
| | 3911953 | 1 |
| | 3909654 | 1 |
| | 3914467 | 1 |
| | 3445488 | 1 |
| | 4237375 | 1 |
| | 3491843 | 1 |
| | 3491843 | 1 |

The results with the pY1068 peptide (SEQ IID NO: 7) (Table 30) also reflected the expected result with the highest signals from clones of Grb2 and PLCγ.

TABLE 30

| | | pY1068 |
|---|---|---|
| Grb2 | 4398016 | 119 |
| PLCγ | 4419252 | 55 |
| | 3919253 | 3 |
| | 3445488 | 2 |
| | 3886018 | 2 |
| | 3909921 | 1 |
| | 3911953 | 1 |
| | 3909654 | 1 |
| | 3914467 | 1 |

The results from the Myc peptide (SEQ ID NO: 4) (Table 31) were as expected as no protein binding partner has been identified as yet. The weak binding to the βTRCP clone products was not unexpected due to the homologous nature of the Myc peptide to that of the IkB peptide.

TABLE 31

| | | Myc |
|---|---|---|
| βTRCP | 4237375 | 10 |
| βTRCP | 3491843 | 8 |
| | 3445488 | 6 |
| | 3886018 | 5 |
| | 3915089 | 5 |
| | 3908004 | 5 |
| | 3491843 | 4 |
| | 3452714 | 4 |
| | 3463640 | 4 |

Tyrosine Kinase Assay.

After incubating the 96-well plate with transcription-translation reactions for 50 mm at 30° C., 5 µl of the reaction was mixed with 50 µl of binding buffer, and immobilized onto SA coated NPT-IPR plates by shaking at room temperature for 45 mm. The unbound components of the reaction containing endogenous kinases were removed by washing eight times with wash buffer (25 mM Tris containing 5 mM $MgCl_2$ and 0.004% Triton). Immobilized protein was then used to phosphorylate substrate protein, poly Glu-Tyr (Sigma, pEY) in a 50 µl reaction containing 5 nM pEY, 25 mM Tris buffer pH 7.4, 5 mM $MgCl_2$, 0.05 mM $Na_3VO_4$, 0.004% TritonX-100, 2 mM DTT, EDTA-free protease inhibitor (Roche Molecular Biochemicals) and 100 mM ATP, by shaking at room temperature for 60 minutes. About 45 µl of multi-phosphorylated pEY was transferred to a separate SA coated IPR plate containing a 30 µl mixture of 2.5 nM biotinylated anti-phosphotyrosine and 50 ng Sulfo-TAG labeled anti-phosphotyrosine in buffer containing 25 mM Tris buffer pH 7.4, 5 mM $MgCl_2$, 0.05 mM $Na_3VO_4$, 0.004% TritonX-100, 2 mM DTT and 0.05% IgG. The available phosphotyrosine residues were reacted at room temperature for 60 mm. The unbound reagents were removed by washing three times with water, and the TAG label ECL was detected in presence of 100 µl IPR assay buffer (IGEN International, Inc., Gaithersburg Md.). The ECL signals were measured using an imaging plate reader (IPR).

Figure 3:
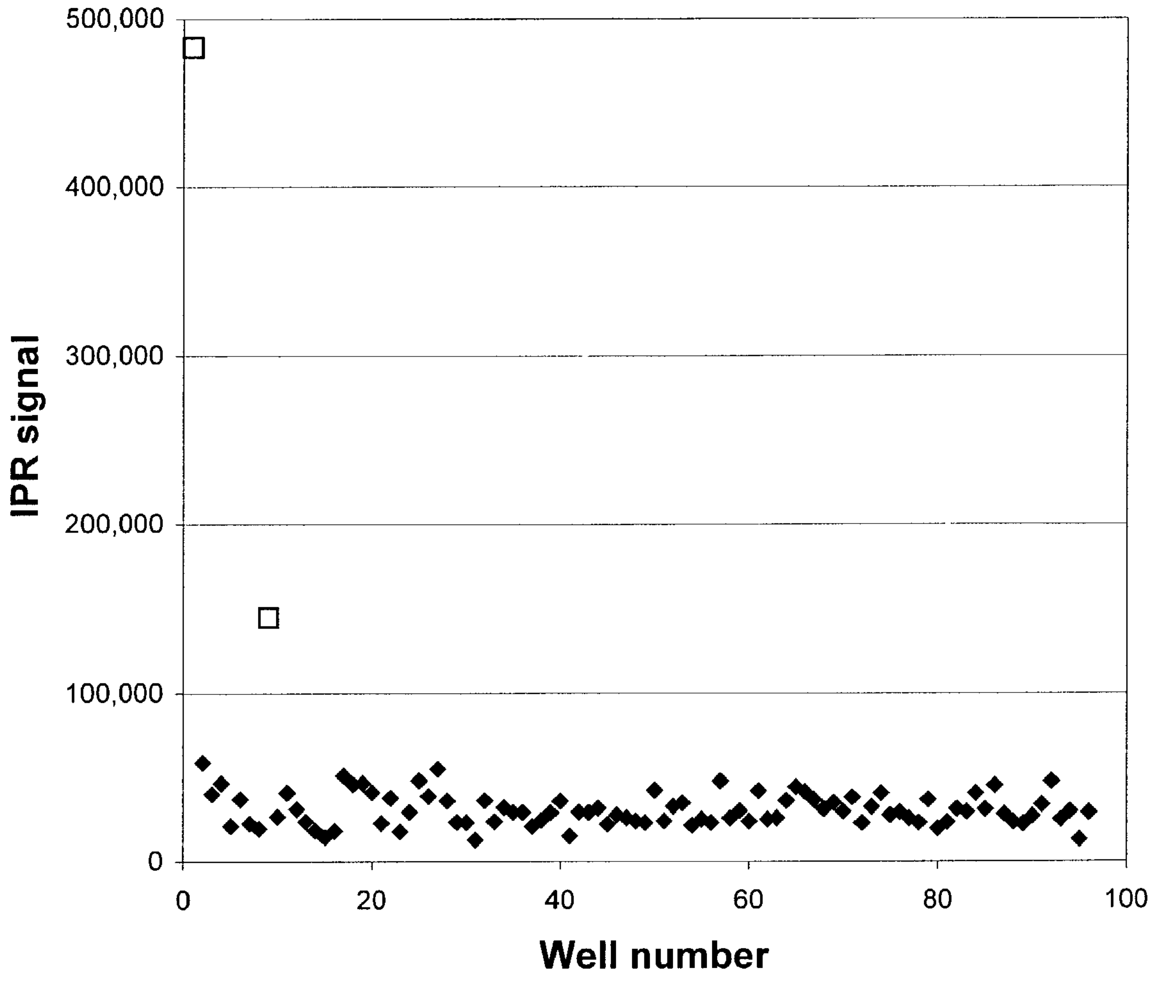
FIG. 3 shows the results electrochemiluminescence assay for identifying protein having Tyrosine Kinase activity. The plot shows ECL signal (vertical axis) as a function of the specific clone number (horizontal axis).

FIG. 3 shows that two Tyrosine Kinase encoding clones (IMAGE ID # 3870426 and 3893964) produced strong specific signals in this assay (□) when compared to the remaining EST clones which produced much weaker signals (♦). Thus in a multiwell based assay system, the assay was able to identify specific tyrosine kinase activity toward substrate pEY from the immobilized proteins.

Example 24

Direct Coating of Proteins onto Magnetic Beads

EST clones were obtained from Incyte (Palo Alto, Calif.). Plasmid DNA was prepared from these EST clones using QIAprep96 Turbo Miniprep (cat#27191, QIAgen, Los Angeles, Calif.), according to manufacturer's instructions. cDNA was eluted using 150 µl buffer EB (QIAgen).

The DNA from these clones was translated in a transcription and translation system as described in Materials and Methods. For binding of the proteins from the TnT reaction to the magnetic beads we used the following protocol. The transcription-translation reaction (1 µl) was added to 40 µg of uncoated magnetic beads (SPHERO(™) Carboxyl Magnetic Particles—Smooth Surface, 1% w/v, 3.2 µm Cat# CMS-30-5, Spherotech,) in 50 ul PBS pH 7.4, with EDTA and protease inhibitors (Roche Biochemicals) in a 96 well plate. The beads were incubated for 2 hours followed by the addition of 35–40 ng Sulfo-TAG labeled streptavidin to each well in a 50 µl volume using assay buffer (25 mM Tris pH7.4, 0.005% Triton, 1% BSA, protease inhibitors) and the plate was incubated for 1 h at room temperature with shaking. After incubation, 100 µl of assay buffer was added and the plate was analyzed by ECL detection on an M8 Analyzer (IGEN International, Inc., Gaithersburg, Md.). The results demonstrate the binding of proteins directly to a magnetic bead from the TnT reactions. Typically signals are in the range of 5–160 fold over the signal seen with vector controls not producing proteins from cloned DNA. This data correlated well with a radioactive assay where the products of the transcription and translation were analyzed by gel electrophoresis followed by detection and quantitation of the incorporated C14 labeled lysine.

Example 25

Screening for EGFR Binding Proteins

The example describes an ORIGEN based HTS assay for EGFR binding to reticulocyte lysate-expressed Grb2 and PLCγ. The assay uses Sulfo-TAG labeled anti-EGFR/anti-phosphotyrosine for detection.

Upon EGF activation of cells, several adapter proteins bind specific sites in EGFR and transduce signals inside the cells. Seven tyrosine moieties of EGFR are under the regulation of autophosphorylation dependant signaling. The goals of this assay are to identify the members of proteome that interact to the phosphopeptide motifs of EGFR. The interactions of Grb2 to pY1068 site and PLCγ to pY992 and pY1173 sites of EGFR are well established. We have developed screening methods to detect specific EGFR binding to in vitro expressed cDNAs. The assay format developed for this purpose utilizes following steps:

Proteins were produced in an in vitro transcription and translation reaction using 40–100 ng of plasmid DNA. Mock (Luciferase, Promega), Grb2 or PLCγ (IMAGE IDs# 4398016 or 4419252, Incyte Genomics, CA) were produced and immobilized on SA coated NPT-IPR plates as described in the Materials and Methods. The unbound components of the reaction containing endogenous kinases were removed by three washes with TT-buffer (25 mM Tris-HCl buffer pH 7.4 and 0.004% Triton), two five minutes washings with high-salt wash buffer (25 mM Tris-HCl buffer pH 7.4, 0.004% Triton, 1M NaCl and 5 mM DTT) and 3 more washes with TT-buffer. To these immobilized and purified proteins 1.5 nM phosphorylated EGFR (Sigma Chemical Co, MO, self-phosphorylated for 30 min in presence of 25 mM Tris-HCl buffer pH 7.4, 0.05 mM $Na_3VO_4$, 0.004% TritonX-100, 2 mlvi DTT, 5 mM MgCl2, 5 mM MnCl2, 100 µM ATP) was added in buffer containing 1X Phosphate buffered saline (Quality Biological, MD), 0.004% TritonX-100, 2 mM DTT and EDTA-free protease inhibitor (Roche Molecular Biochemicals, IN), and allowed to bind for 45 minutes. The unbound EGFR was washed by 4 times washing with TT-buffer (25 mM Tris-HCl buffer pH 7.4 and 0.004% Triton). The amount of EGFR bound to the reticulocyte lysate expressed protein was determined by detecting the kinase activity of EGFR. A tyrosine kinase substrate, 5 nM pEY (poly Glu-Tyr, Sigma, MO) was added in a 50 µl reaction containing 5 mM $MgCl_2$, 5 mM MnCl2, 100 µM ATP, 25 mM Tris-HCl buffer pH 7.4, 0.05 mM $Na_3VO_4$, 0.004% TritonX-100, 2 mM DTT and EDTA-free protease inhibitor (Roche Molecular Biochemicals). This mixture was incubated with shaking at room temperature for 1 or 12 hours to allow phosphorylation of the pEY substrate by the EGFR. Following this incubation 45 µl of this mixture was transferred to a SA—NPT IPR plate coated with biotinylated anti-phosphotyrosine antibody (PY20, Zymed labs, CA) followed by incubation for 30 minutes at room temperature to allow the binding of the phosphorylated pEY substrate to the PY20 coated NPT plate. Following this binding step 50 ng Sulfo-TAG labeled anti-phosphotyrosine in buffer containing 25 mM Tris-HCl buffer pH 7.4, 5 mM $MgCl_2$, 0.05 mM $Na_3VO_4$, 0.004% TritonX-100, 2 mM DTT and 0.05% IgG was added followed by incubation at room temperature for 30 mm.

Alternatively, the bound EGFR was directly detected in the original plate by incubating with 20 nM TAG labeled anti-EGFR (Clone 225, Neo Markers, CA) in 50 µl buffer containing 25 mM Tris-HCl buffer pH 7.4, 5 mM MgCl2, 0.05 mM $Na_3VO_4$, 0.004% TritonX-100, 2 mM DTT and 0.05% IgG at room temperature for 60 min.

The unbound reagents were removed by one time washing with TT-buffer (25 mM Tris-HCl buffer pH 7.4 and 0.004% Triton), and the TAG label was detected in presence of 150 µl IPR assay buffer (0.4 mM Gly-Gly buffer, pH 7.8, 1 mM EDTA, 0.1 M TPA). The ECL signals were measured using an imaging plate reader.

We have demonstrated that Grb2 and PLCγ specifically bind to EGFR; these are suggested to interact through phosphorylated sites of EGFR. The control protein Luciferase (Mock) did not show any significant level of binding to EGFR. The binding of EGFR to Grb2 or PLCγ was detected either by identifying tyrosine kinase activity of EGFR towards pEY (see Table 32) or directly by using TAG-labeled anti-EGFR (Table-33). The detection of bound EGFR was substantially increased by its prolonged (12 hr) phosphorylation of tyrosine kinase substrate pEY (see Table 32).

TABLE 32

| Reticulocyte lysate | Reaction time | − | + | + | + | + |
|---|---|---|---|---|---|---|
| Plasmid | | none | Grb2 | PLCγ | Mock | none |
| no EGFR | — | 957 | 1,497 | 1,695 | 1,462 | 1,426 |
| +EGFR | 1 hr | 2,241 | 25,214 | 17,966 | 2,683 | 2,598 |
| +EGFR | 12 hr | 2,429 | 62,912 | 39,767 | 3,303 | 3,088 |

TABLE 33

| Reticulocyte lysate | − | + | + | + |
|---|---|---|---|---|
| Plasmid | none | Grb2 | PLCγ | Mock |
| no EGFR | 2,181 | 2,356 | 2,271 | 2,534 |
| +EGFR | 5,447 | 48,027 | 30,389 | 8,742 |

The interaction of Grb2 towards EGFR known to be mediated through phosphotyrosine site 1068 was further confirmed in this assay as the EGFR binding to this proteins was significantly reduced in presence of phosphorylated (pY1068) form of the peptide (Phosphopeptide, amino acids 1063–1081 (SEQ ID NO: 7)), but not in the presence of its un-phosphorylated form (Peptide (SEQ ID NO: 8)) (see Table 34).

TABLE 34

| Plasmid | | | |
|---|---|---|---|
| Mock | +EGFR | | 2,683 |
| Grb2 | +EGFR | | 25,214 |
| Grb2 | +EGFR | +Phosphopeptide | 7,348 |
| Grb2 | +EGFR | +Peptide | 34,055 |
| none | +EGFR | | 2,598 |

Example 26

ORIGEN Based HTS Assay for Protein Tyrosine Phosphatase Activity of PTP-N2 (Protein Tyrosine Phosphatase, Non-Receptor Type 2) Expressed in Reticulocyte Lysate The example demonstrates an assay to screen for protein tyrosine phosphatase activity.

Protein Tyrosine phosphatases (PTPs) are a family of enzymes found ubiquitously in cells, and are not only are involved in growth factor mediated signaling process, but also are implicated in modulating other cellular processes such as the maintaining integrity of the cytoskeleton and cell-cell interactions. T-cell protein tyrosine phosphatase (PTP-N2) is one such phosphatase that exits the nucleus upon EGF receptor activation and recognizes the EGFR and $p52^{Shc}$ as a cellular substrates (Tiganis et. Al Mol. Cell. Biol. 18, 1680, 1998). Using in vitro expression screening strategy, we have measured the phosphatase activity from full-length clone PTP-N2 (protein tyrosine phosphatase, non-receptor type 2). The assay format developed for this purpose utilizes following steps:

Several proteins were produced in an in vitro transcription and translation reaction using 1–150 ng of plasmid DNA including: Mock Luciferase (Promega); protein tyrosine phosphatase; non-receptor type 2 (PTP-N2, IMAGE ID# 3872164, Incyte Genomics, CA); and fer (fms/fps related) protein kinase, testis specific 2 clone (Fert2, IMAGE ID# 4485050, Incyte Genomics, CA). The proteins were produced and immobilized on SA coated NPT-IPR plates, as described in Example 7. The unbound components of the translation reaction (including endogenous kinases) were removed by 3 washes with TT-buffer (25 mM Tris-HCl buffer pH 7.4 and 0.004% Triton), two five minutes washes with high-salt wash buffer (25 mM Tris-HCl buffer pH 7.4, 0.004% Triton, 1M NaCl and 5 mM DTT) and 3 washes with TT-buffer.

A tyrosine phosphate substrate was prepared by enzymatically phosphorylating poly(Glu, Tyr). To the immobilized and purified Fert2 kinase, a tyrosine kinase substrate (2.5 µM of poly(Glu, Tyr)) was added in a 50 µl reaction containing 5 mM $MgCl_2$, 5 mM MnCl2, 100 µM ATP, 25 mM Tris-HCl buffer pH 7.4, 0.004% TritonX-100, 2 mM DTT and EDTA-free protease inhibitor (Roche Molecular Biochemicals). This mixture was incubated with shaking at room temperature for 45 min to allow phosphorylation of the pEY substrate by the immobilized Fert2. The phosphorylation in the product was determined by transferring serially diluted reaction mixture to a streptavidin-coated NPT IPR plate and assaying for phosphorylated-poly(Glu, Tyr) as described in previous examples (see, e.g., Example 7).

The phosphorylated poly(Glu, Tyr) was used as a substrate to measure the phosphatase activity of the purified and immobilized PTP-N2. To wells containing immobilized PTP-N2 was added 50 uL of a reaction mixture containing 5 nM phospho-pEY (described above), 5 mM $MgCl_2$, 25 mM Tris-HCl buffer pH 7.4, 0.004% TritonX-100, 2 mM DTT and EDTA-free protease inhibitor (Roche Molecular Biochemicals). This mixture was incubated with shaking at room temperature 45 min to allow de-phosphorylation of the phospho-pEY substrate by the immobilized phosphatase. Following this incubation 45 µl of this mixture was transferred to a streptavidin-coated NPT IPR plate and the solution analyzed for phospho-poly(Glu, Tyr) content as described above.

Using our novel phosphatase substrate (phospho-pEY), a significant decrease in the signal was observed due to phosphatase activity from PTP-N2, when compared to Mock (Luciferase) (see Table 35).

TABLE 35

| | ECL signal |
|---|---|
| No TnT reactants | 487,082 |
| Mock | 408,302 |
| PTP-N2 | 70,574 |

Example 27

In Vitro Assay for a Set of Kinases

This example illustrates the use of methods of the invention to express a library of potential kinases and screen this library for kinase activity. In this example, the kinases were assayed for their ability to auto-phosphorylate as well as their ability to phosphorylate a non-autologous substrate.

Proteins were produced in an in vitro transcription and translation reaction as described in the Materials and Methods. This process resulted in the transcription and translation of the various proteins with biotin groups randomly incorporated at some lysine residues. The reaction was stopped by mixing with BB2 buffer. Biotinylated proteins from 50 μl of the mixture (representing 0.5 μl to 5 μl of TnT reaction) were immobilized onto streptavidin or avidin coated NPT-IPR plates by shaking at room temperature for 45 min. The activity of the immobilized protein towards pEY or autophosphorylation was further assayed by the methods described in examples 7 and 8.

When 5 ul of expressed protein was tested for its activity towards pEY, clones having sequence or structural homology to known tyrosine kinase catalytic domains, phosphotransferases, or the tyrosine-specific kinase subfamily showed significantly higher signal than non-kinases or proteins serving as substrates to tyrosine kinases (Scap2) (see Table 12 below).

TABLE 36

| IMAGE ID | Locus | | HTS signal |
|---|---|---|---|
| 2644960 | Kit | kit oncogene | 9,164 |
| 2654352 | Fgfr2 | fibroblast growth factor receptor 2 | 296,481 |
| 3156400 | Src | Rous sarcoma oncogene | 145,950 |
| 3156953 | Wee1 | wee 1 homolog (S. pombe) | 981 |
| 3482498 | Tek | endothelial-specific receptor tyrosine kinase | 10,287 |
| 3601246 | FRK | B-cell src-homology tyrosine kinase | 15,235 |
| 3673003 | Ephb3 | Eph receptor B3 | 1,174 |
| 3866791 | JAK1 | Janus kinase 1 (a protein tyrosine kinase) | 729 |
| 3870426 | SYK | spleen tyrosine kinase | 650,826 |
| 3873932 | MATK | megakaryocyte-associated tyrosine kinase | 47,477 |
| 3896359 | FGFR1 | fibroblast growth factor receptor 1 (fms-related TK2) | 2,339 |
| 3919253 | BMX | BMX non-receptor tyrosine kinase | 523,662 |
| 3921724 | FGR | FYN oncogene related to SRC | 93,081 |
| 3978518 | Hck | hemopoietic cell kinase | 184,534 |
| 3982920 | Clk4 | CDC like kinase 4 | 2,244 |
| 3989782 | Yes | Yamaguchi sarcoma viral (v-yes) oncogene homolog | 2,208 |
| 3991628 | EPHA7 | Eph receptor A7 | 24,930 |
| 3995512 | CLK2 | CDC-like kinase 2 | 634 |
| 4013934 | Ephb4 | Eph receptor B4 | 7,357 |
| 4036253 | CLK3 | CDC-like kinase 3 | 704 |
| 4037899 | FGFR1 | fibroblast growth factor receptor 1 | 450,413 |

TABLE 36-continued

| IMAGE ID | Locus | | HTS signal |
|---|---|---|---|
| 4181574 | NTRK3 | neurotrophic tyrosine kinase | 36,515 |
| 4190326 | Lyn | Yamag sarcoma viral (vyes1) oncogene homolog | 427,178 |
| 4191610 | LCK | lymphocyte protein tyrosine kinase | 3,110 |
| 4238984 | Kdr | kinase insert domain protein receptor | 107,459 |
| 4239139 | Fgfr4 | fibroblast growth factor receptor 4 | 7,343 |
| 4343428 | PTK2B | protein tyrosine kinase 2 beta | 57,486 |
| 4363897 | FGR | FYN oncogene related to SRC | 402,243 |
| 4384416 | BTK | Bruton agammaglobulinemia tyrosine kinase | 793,874 |
| 4387232 | CLK1 | CDC-like kinase 1 | 5,109 |
| 4398416 | Csk | c-src tyrosine kinase | 683,039 |
| 4419031 | BLK | B lymphoid tyrosine kinase | 37,907 |
| 4419700 | LCK | lymphocyte-specific protein tyrosine kinase | 898 |
| 4419973 | FGR | GR feline sarcoma viral (v-fgr) oncogene homolog | 104,946 |
| 4471986 | ALK | anaplastic lymphoma kinase (Ki-1) | 905 |
| 4485050 | Fert2 | fer (fms/fps related) protein kinase | 952,661 |
| 4498209 | EPHB1 | EphB1 | 853 |
| 4515877 | Frk | fyn-related kinase | 271,855 |
| 4537393 | TTK | TTK protein kinase | 1,711 |
| 4778819 | Hck | hemopoietic cell kinase | 958,415 |
| | | Negative Controls | |
| | | Mock | 520 |
| | | Average signal of ten Non-Tyrosine Kinase clones | 564 |
| 3599914 | Scap2 | Tyrosine Kinase substrate | 587 |

Similarly, the autophosphorylation activity from the expressed protein of these clones was robustly detected, as the signal from kinases was significantly different from the signal from non-kinases (Table 37).

TABLE 37

| IMAGE ID | Locus | | ECL signal |
|---|---|---|---|
| 2644960 | Kit | kit oncogene | 88,966 |
| 2654352 | Fgfr2 | fibroblast growth factor receptor 2 | 180,059 |
| 3156400 | Src | Rous sarcoma oncogene | 76,933 |
| 3156953 | Wee1 | wee 1 homolog (S. pombe) | 27,452 |
| 3482498 | Tek | endothelial-specific receptor tyrosine kinase | 84,706 |
| 3601246 | FRK | B-cell src-homology tyrosine kinase | 28,243 |
| 3673003 | Ephb3 | Eph receptor B3 | 10,540 |
| 3870426 | SYK | spleen tyrosine kinase | 228,700 |
| 3873932 | MATK | megakaryocyte-associated tyrosine kinase | 27,372 |
| 3896359 | FGFR1 | fibroblast growth factor receptor 1 (fms-related TK2) | 7,696 |
| 3919253 | BMX | BMX non-receptor tyrosine kinase | 443,933 |
| 3921724 | FGR | FYN oncogene related to SRC | 241,697 |
| 3978518 | Hck | hemopoietic cell kinase | 301,418 |
| 3982920 | Clk4 | CDC like kinase 4 | 192,787 |
| 3989782 | Yes | Yamaguchi sarcoma viral (v-yes) oncogene homolog | 4,542 |
| 3991628 | EPHA7 | Eph receptor A7 | 115,662 |
| 3995512 | CLK2 | CDC-like kinase 2 | 20,748 |
| 4013934 | Ephb4 | Eph receptor B4 | 28,275 |
| 4036253 | CLK3 | CDC-like kinase 3 | 42,712 |
| 4037899 | FGFR1 | fibroblast growth factor receptor 1 | 240,550 |
| 4181574 | NTRK3 | neurotrophic tyrosine kinase | 55,017 |
| 4190326 | Lyn | Yamaguchi sarcoma viral (vyes1) oncogene homolog | 599,680 |
| 4191610 | LCK | lymphocyte protein tyrosine kinase | 24,183 |
| 4238984 | Kdr | kinase insert domain protein receptor | 61,364 |
| 4239139 | Fgfr4 | fibroblast growth factor receptor 4 | 12,588 |
| 4343428 | PTK2B | protein tyrosine kinase 2 beta | 274,742 |
| 4363897 | FGR | FYN oncogene related to SRC | 44,220 |

TABLE 37-continued

| IMAGE ID | Locus | | ECL signal |
|---|---|---|---|
| 4384416 | BTK | Bruton agammaglobulinemia tyrosine kinase | 1,503,772 |
| 4387232 | CLK1 | CDC-like kinase 1 | 423,938 |
| 4398416 | Csk | c-src tyrosine kinase | 349,847 |
| 4419031 | BLK | B lymphoid tyrosine kinase | 146,775 |
| 4419700 | LCK | lymphocyte-specific protein tyrosine kinase | 7,230 |
| 4419973 | FGR | Gardner-Rasheed feline sarcoma viral (v-fgr) oncogene homolog | 117,395 |
| 4471986 | ALK | anaplastic lymphoma kinase (Ki-1) | 4,069 |
| 4485050 | Fert2 | fer (fms/fps related) protein kinase | 1,350,546 |
| 4498209 | EPHB1 | EphB1 | 3,138 |
| 4515877 | Frk | fyn-related kinase | 148,139 |
| 4537393 | TTK | TTK protein kinase | 50,479 |
| 4778819 | Hck | hemopoietic cell kinase | 1,198,625 |
| | | Negative Controls | |
| | | Mock | 2,251 |
| | | Non-Tyrosine Kinase clones (n = 10) | 2,169 |
| 3599914 | Scap2 | TK substrate, Scap2 | 2,912 |

Example 28

ORIGEN Based HTS Assay for Kinase Activity of Tyrosine Kinase Array in Presence of Kinase Inhibitors This example shows the profiling of a panel of kinase inhibitors against a panel of tyrosine kinases. The example demonstrates the use of proteins expressed in in vitro transcription/translation systems in inhibition assays and/or drug screening assays. The example shows specificity data for proteins generated from a library of eighteen full-length clones. The assay format developed for this purpose utilizes following steps:

Proteins were produced using 100 ng of plasmid DNA Mock (Luciferase, Promega) or tyrosine kinases (Fert2 IMAGE ID # 4485050, FGFR1 IMAGE ID # 4037899, Fgfr2 IMAGE ID # 2654352, Src IMAGE ID # 3156400, BMX IMAGE ID # 3919253, LCK IMAGE ID # 4191610, Epha7 IMAGE ID # 3991628, Ephb4 IMAGE ID # 4013934, Tek IMAGE ID # 3482498, HCK IMAGE ID # 4778819, BTK IMAGE ID # 4478463, CSK IMAGE ID # 4398416, SYK IMAGE ID # 3870426, FGR IMAGE ID # 4419973, PTK2B IMAGE ID # 4339456, FRK(IMAGE ID # 4515877, Kit IMAGE ID # 2644960, Fgfr-4 IMAGE ID # 4239139, NTRK3 IMAGE ID # 4181574, Kdr IMAGE ID # 4238984, Incyte Genomics, CA) and immobilized on SA or avidin coated NPT-IPR plates as described in previous examples. The unbound components of the translation reaction (including any endogenous kinases) were removed by 3 washes with TT-buffer (25 mM Tris-HCl buffer pH 7.4 and 0.004% Triton), two five minutes washes with high-salt wash buffer (25 mM Tris-HCl buffer pH 7.4, 0.004% Triton, 1M NaCl and 5 mM DTT) and 3 washes with TT-buffer. To these immobilized and purified proteins a tyrosine kinase substrate, 10 nM pEY (poly Glu-Tyr, Sigma, MO) was added in 25 μl of buffer A (5 mM MgCl2, 5 mM MnCI2, 25 mM Tris-HCl buffer pH 7.4, 0.05 mM $Na_3VO_4$, 0.004% TritonX-100, 2 mM DTT and EDTA-free protease inhibitor) containing 1 μL of one of a DMSO solution of one of the potential inhibitors (Damnacanthal, PP2, AG 490, WHIP 131, LFMA 13, AG 597, Lavendustin A, Compound 56, Genistein, AG1478, AG 1296, AG 17, AG 1024, AG 538, AG 879, SU 1498, Oxindole 1,VEGFR2 inhibitor1, VEGFR inhibitor were from CalBiochem, Pasadena, Calif.; and PP1, Erbstatin Analogue and AG1433 were from AG Scientific, San Diego, Calif.). The mixture was incubated at room temperature for 10 mm before starting the kinase reaction by adding 25 μl of 200 μM ATP in buffer A. This mixture was incubated with intermittent shaking at room temperature for 2 hours to overnight to allow (a) phosphorylation of the pEY substrate and (b) autophosphorylation of the immobilized kinases. Autophosphorylation and phosphorylation of the pEY was measured as described in Examples 7 and 8.

We used tyrosine kinase inhibitors at 1× and 10× the reported IC50 concentrations for inhibition of the tyrosine kinases reported to be the target of each inhibitor (1× concentrations were 620 nM Damnacanthal, 600 nM PP1, 4 nM PP2, 100 nM AG-490, 7.8 μM WHI-P131, 17.2 μM LFM-A13, 750 nM AG-957, 780 nM Erbstatin, 11 nM Lavendustin A, 6 pM Compound-56, 2.6 μM Genistein, 3 nM AG-1478, 5 μM AG-1433, 1 μM AG-1296, 500 nM AG-17, 18 μM AG-1024, 60 nM AG-538, 10 μM AG879, 700 nM SU-1498, 390 nM Oxindole 1, 2 μM VEGFR inhibitor and 70 nM VEGFR2 inhibitor) and tested their specificity against an “Array of Kinases”, eighteen tyrosine kinases representing diverse family of non-membrane and membrane bound kinases. The ECL signal in control wells produced by tyrosine kinases was compared to the wells containing inhibitor compounds. The signal produced from Mock was negligible. Thus, a profile of inhibition specificity for each compound for high inhibition (“H”=less than 25% of the activity remaining), medium inhibition (“M”=between 25 to 50% of the activity remaining), and low inhibition (“L”=between 50–75% of the activity remaining) was developed towards pEY substrate phosphorylation (Table 38) and autophosphorylation (Table 39).

TABLE 38

| | Inhibition specificity towards pEY phosphorylation at 10X IC50 | | | | | | | | | | | | | | | | | |
|---|---|---|---|---|---|---|---|---|---|---|---|---|---|---|---|---|---|---|
| | Fert2 | FGFR1 | FGFR2 | Src | BMX | LCK | Epha7 | EphB4 | Tek | HCK | BTK | CSK | SYK | PTK2B | FRK | Kit | Fgfr4 | Kdr |
| Damnacanthal | L | H | H | H | H | H | H | H | M | H | H | H | H | H | H | H | H | H |
| PP1 | | L | | | L | M | | L | | | M | | | | | M | M | M |
| PP2 | | | | | | | | | | | | | | | | L | | |
| AG-490 | | | | | | | | | | | L | | | | | | | |
| WHI-P131 | | L | L | L | L | H | L | M | L | L | M | | | L | | H | L | H |
| LFM-A13 | | | | | | | | | | | M | | | | | M | M | L |
| AG-957 | | L | L | | L | | | L | L | | | M | | | | L | | |
| Erbstatin analog | | | | | | | | L | | | | | | | | L | | |

TABLE 38-continued

| | Inhibition specificity towards pEY phosphorylation at 10X IC50 | | | | | | | | | | | | | | | | | |
|---|---|---|---|---|---|---|---|---|---|---|---|---|---|---|---|---|---|---|
| | Fert2 | FGFR1 | FGFR2 | Src | BMX | LCK | Epha7 | EphB4 | Tek | HCK | BTK | CSK | SYK | PTK2B | FRK | Kit | Fgfr4 | Kdr |
| Lavendustin A | | | | | | | | | | | | | | | | L | | |
| Compound-56 | | | | | | | | | | | | | | | | | | |
| Genistein | | | | | | | | L | | | | | | | | M | | |
| AG-1478 | | | | | | | | | | | | | | | | | | |
| AG-1433 | | H | H | H | H | | L | H | M | M | H | M | M | L | | H | H | H |
| AG-1296 | | | | | | | | L | | | | | | | | M | | |
| AG-17 | | | | | | | | | | | | | | | | L | | |
| AG-1024 | | L | L | | | | | L | L | | H | | L | | | L | M | M |
| AG-538 | | | | | | | | | | | | | | | | | | |
| AG879 | | | | | | | | | | | L | | | | | | | |
| SU-1498 | | | | | | | | | | | | | | | | | | |
| Oxindole 1 | | | | | | | | | | L | M | M | L | M | L | H | M | H |
| VEGFR inhibitor | | | L | | | H | | M | | | M | | | | | L | L | H |
| VEGFR2 inhibitor | H | H | H | H | L | | | L | L | | | | | | | M | | M |

TABLE 39

| | Inhibition specificity towards Autophosphorylation at 10X IC50 | | | | | | | | | | | | | | | | | |
|---|---|---|---|---|---|---|---|---|---|---|---|---|---|---|---|---|---|---|
| | Fert2 | FGFR1 | FGFR2 | Src | BMX | LCK | Epha7 | Ephb4 | Tek | HCK | BTK | CSK | SYK | PTK2B | FRK | Kit | Fgfr4 | Kdr |
| Damnacanthal | L | M | M | H | H | H | H | H | H | M | H | M | M | M | H | H | H | H |
| PP1 | | | | L | | | | | | | | | | | | | | L |
| PP2 | | | | | | | | | | | | | | | L | | | |
| AG-490 | | | | | | | | | | | | | | | | | | |
| WHI-P131 | | | | | | M | | | | | | | | | | L | | M |
| LFM-A13 | | | | | | | | | | | L | | | | | | | |
| AG-957 | | L | L | L | L | | | L | M | L | L | L | L | L | L | L | L | L |
| Erbstatin analog | L | | L | L | L | L | | L | L | L | L | | L | L | | L | | L |
| Lavendustin A | | | | | | | | | | | | | | | | | | |
| Compound-56 | | | | | | | | | | | | | | | | | | |
| Genistein | | | | | | | | | | | | | | | | | | |
| AG-1478 | | | | | | | | | | | | | | | | | | |
| AG-1433 | H | H | H | H | H | H | H | H | H | H | H | H | H | H | H | H | H | H |
| AG-1296 | | | | | | | | | | | | | | | | | | |
| AG-17 | | | | | | | | | | | | | | | | | | |
| AG-1024 | | | L | | | | | | M | | L | | | | | | L | |
| AG-538 | | | | | | | | L | | | | | | | | | | |
| AG879 | | | | | | | | | | | | | | | | | | |
| SU-1498 | | | | | | | | | | | | | | | | | | |
| Oxindole 1 | | | | | | | | | | | L | | L | L | | M | L | M |
| VEGFR inhibitor | | | | | | L | | L | | | L | | | | | | | M |
| VEGFR2 inhibitor | H | H | H | H | | | | | L | | | | | | | | | L |

8. INCORPORATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method of producing a multi-well plate with at least 20 wells each containing a different in vitro transcription and translation product, said method comprising:

(a) obtaining at least 20 different nucleic acid constructs, (b) simultaneously transcribing said at least 20 different nucleic acid constructs in different wells of said mule-well plate to generate RNAs, (c) simultaneously translating said RNAs in said wells, using a cell-free translation system containing a tRNA precharged with a modified amino acid, to produce at least 20 different amino acid sequences containing said modified amino acid, and (d) immobilizing said amino acid sequences on one or more solid phase surfaces.

2. The method of claim 1, wherein said solid phase support is an electrode.

3. The method of claim 1, further comprising e) contacting said amino acid sequence with a first enzyme that introduces or removes post-translational modifications.

4. A method for screening nucleic acid constructs for those encoding amino acid sequences subject to a post-translational modification activity comprising the following steps:

a) obtaining a plurality of nucleic acid constructs, b) simultaneously transcribing said nucleic acid constructs in different wells of a multi-well plate to generate RNAs, c) simultaneously translating said RNAs in said wells of said multi-well plate, using a cell-free system containing a tRNA precharged with a modified amino acid, to produce a plurality of amino acid sequences containing said modified amino acid, and d) detecting said post-translational modification of said plurality of amino acid sequences by a solid phase binding assay for the binding of said amino acid sequences to binding species specific for said post-translational modification.

5. The method of claim 4, wherein said binding species is immobilized on a solid phase and said solid phase binding assay comprises:

i) binding said amino acid sequence to said binding species so as to capture said amino acid sequence on said solid phase, and ii) detecting said captured amino acid sequences on said solid phase using a binding reagent specific for said modified amino acid.

6. The method of claim 4, wherein said solid phase binding assay comprises:

i) capturing said amino acid sequence on a surface of a solid phase via an immobilized binding reagent specific for said modified amino acid, and ii) detecting said captured amino acid sequences on said surface using a binding species specific for said post-translational modification.

7. The method of claim 6, wherein said solid phase comprises an array of additional binding species specific for different post-translational modifications.

8. The method of claim 4, wherein said cell-free system further comprises a substrate that can be linked to a protein to form a post-translational modification.

9. A method for screening nucleic acid constructs for those encoding amino acid sequences subject to a post-translational modification activity comprising the following steps:

(a) obtaining a plurality of nucleic acid constructs, (b) simultaneously transcribing said nucleic acid constructs in different wells of a multi-well plate to generate RNAs, (c) simultaneously translating said RNAs in said wells of said multi-well plate, using a cell-free system containing a tRNA precharged with a modified amino acid and a substrate that can be linked to a protein to form a post-translational modification, said substrate being modified with a detectable species, to produce at least one amino acid sequence containing said modified amino acid and said post-translational modification, and (d) detecting said post-translational modification of said amino acid sequence by a solid phase binding assay for the binding of said amino acid sequence to a binding species specific for said post-translational modification or the binding of said amino acid sequence to a binding reagent specific for said modified amino acid.

10. The method of claim 9, wherein said binding reagent is immobilized on a solid phase and said solid phase binding assay comprises:

i) capturing said amino acid sequence on said solid phase by a binding interaction with said binding reagent; and ii) detecting said captured amino acid sequences on said solid phase using said detectable species on said post-translational modification.

11. The method of claim 9, wherein said binding species is immobilized on said solid phase and said solid phase binding assay comprises:

(i) capturing said amino acid sequence on said solid phase by a binding interaction with said binding species; and ii) detecting said captured amino add sequences on said solid phase using said modified amino acid.

12. The method of claim 11, wherein said solid phase comprises an array of additional binding species specific for different post-translational modifications.

13. A method for screening nucleic acid constructs for those encoding amino acid sequences with enzymatic activity comprising the following steps:

(a) obtaining a nucleic acid construct, (b) transcribing said nucleic acid to generate RNA, (c) translating said RNA in a cell-free system containing a tRNA precharged with a modified amino acid, to produce an amino acid sequence containing said modified amino acid, and (d) detecting enzymatic activity of said amino acid sequence using a method comprising the following steps:

(i) capturing said amino acid sequence onto a solid phase via an immobilized binding reagent specific for said modified amino acid, (ii) adding enzyme reaction buffer, and (iii) detecting the product of the enzyme activity.

14. A method for screening nucleic acid constructs for those encoding amino acid sequences that are substrates of enzymatic activity comprising the following steps:

(a) obtaining a nucleic acid construct, (b) transcribing said nucleic acid to generate RNA, (c) translating said RNA in a cell-free system containing a tRNA precharged with a modified amino acid, to produce an amino acid sequence containing said modified amino acid, and (d) detecting said amino acid sequences which are substrates of an enzyme activity using a method comprising the following steps:

(i) capturing said amino acid sequence onto a solid phase via an immobilized binding reagent specific for said modified amino acid;

ii) adding an enzyme; and iii) detecting the product of the enzyme activity on said amino acid sequence.

15. The method of claim 14, further comprising the step of treating said captured amino acid sequence with one or more reagents that remove a post-translational modification that occurred during said translating step.

16. A method for screening nucleic acid constructs for those encoding amino acid sequences with binding activity comprising the following steps:

(a) obtaining a nucleic acid construct, (b) transcribing said nucleic acid to generate RNA, (c) translating said RNA in a cell-free system containing a tRNA precharged with a modified amino acid, to produce an amino acid sequence containing said modified amino acid, and (d) detecting binding activity of said amino acid sequence for a binding partner via a solid phase binding assay.

17. The method of claim 16, wherein said solid phase assay comprises:

(i) capturing said amino acid sequence on a solid phase using an immobilized binding reagent specific for said modified amino acid, and (ii) detecting said captured binding activity using said binding partner.

18. The method of claim 16, wherein said binding partner is immobilized on a solid phase and said solid phase binding assay comprises the steps of:

(i) capturing said amino acid sequence on solid phase via said binding activity to said binding partner immobilized on said solid phase, and (ii) detecting said captured amino acid sequence on said solid phase using said modified amino acid.

19. The method of claim 18, wherein said solid phase comprises an array of additional different binding partners for screening for a plurality of binding activities.

20. A method for screening nucleic acid constructs for those encoding amino acid sequences with binding activity comprising the following steps:

(a) obtaining a first nucleic acid construct and second nucleic acid construct, (b) transcribing said first nucleic acid construct to generate a first RNA and transcribing said second nucleic acid construct to generate a second RNA, (c) translating said first RNA in a cell-free system containing a tRNA precharged with an amino acid containing a binding species, to produce a first amino acid sequence containing said binding species, (d) translating said second RNA in a cell-free system containing a tRNA precharged with an amino acid containing a detectable species, to produce a second amino acid sequence containing said detectable species, and (e) detecting binding activity of said first amino acid sequence to said second amino acid sequence using a method comprising the following steps:

(i) contacting a sample of said first amino acid sequence with said second amino acid sequence, (ii) capturing said binding species on a surface of a well of a multi-well plate via a second binding species and (iii) detecting said detectable species bound to said surface.

21. A method for screening nucleic acid constructs for those encoding amino acid sequences with nascent binding activity comprising the following steps:

(a) obtaining a nucleic acid construct, (b) transcribing said nucleic acid to generate RNA, (c) translating said RNA in a cell-free system containing a tRNA precharged with a modified amino acid, to produce an amino acid sequence containing said modified amino acid, (d) capturing said amino acid sequence on a surface of a well of a multi-well plate via a binding reagent specific for said modified amino acid to form a coated surface.

(e) contacting said amino acid sequence with a modifying activity to covalently modify said amino acid sequence, (f) contacting said modified amino acid sequence with a second binding species labeled with a detectable species, and (g) detecting the complex of said second binding species and said immobilized amino acid sequence.

22. A method for screening for antigens with binding activity for antibodies comprising the following steps:

(a) obtaining a nucleic acid construct, (b) transcribing said nucleic acid in vitro to generate RNA, (c) translating said RNA in a cell-free system, to produce an amino acid sequence, and (d) conducting a solid phase binding assay to detect the binding of said amino acid sequence with an antibody.

23. The method of claim 22, wherein said solid phase assay comprises:

(i) immobilizing said amino acid sequence on a solid phase, (ii) mixing said amino acid sequence with said antibody, and (iii) detecting the formation of a binding complex between said antibody and said amino acid sequence.

24. The method of claim 22, wherein said solid phase assay comprises:

(i) forming a composition comprising said amino acid sequence and said antibody, wherein said antibody is immobilized on a solid phase and (ii) detecting the formation of a binding complex between said antibody and said amino acid sequence.

25. The method of claim 24, wherein said solid phase comprises an array of additional different antibodies.

26. The method of claim 4, wherein said solid phase is a bead in a well of a multi-well plate.

27. The method of claim 26, wherein said bead is a magnetic bead.

28. The method of claim 4, wherein said solid phase is a surface of a well of a multi-well plate.

29. The method of claim 28, wherein said surface is an electrode surface.

30. The method of claim 26, wherein a plurality of different amino acid sequences generated from different nucleic acid constructs are tested in parallel in different wells of said multi-well plate.

31. The method of claim 4, wherein said detection step employs electrochemiluminescence detection.

32. The method of claim 4, wherein activity is measured in the presence of test material so as to determine the effect of said test material on said activity.

33. The method of claim 13, wherein said solid phase further comprises an assay domain comprising a reagent that binds a substrate of said enzymatic activity or a product of said enzymatic activity.

34. A method for screening nucleic acid constructs for those encoding amino acid sequences subject to a post-translational modification activity comprising the following steps:

(a) obtaining a nucleic acid construct coding for an amino acid sequence and an affinity tag, (b) transcribing said nucleic acid to generate RNA, c) translating said RNA in a cell-free system to produce an amino acid sequence linked to said affinity tag, and d) detecting said post-translational modification of said amino acid sequence by a solid phase binding assay for the binding of said amino acid sequence to a binding species specific for said post-translational modification.

35. A method for screening nucleic acid constructs for those encoding amino acid sequences with enzymatic activity comprising the following steps:

(a) obtaining a nucleic acid construct, (b) transcribing said nucleic acid to generate RNA, (c) translating said RNA in a cell-free system to produce an amino acid sequence, and (d) detecting enzymatic activity of said amino acid sequence using a method comprising the following steps:

(i) contacting said amino acid sequence with an enzyme substrate immobilized on a solid phase, and (ii) measuring conversion of the substrate to product.

36. The method of claim 35, wherein said solid phase comprises an array of additional different immobilized substrates.

37. The method of claim 35, wherein said enzymatic activity is a kinase activity.

38. The method of claim 1, further comprising contacting said immobilized amino acid sequence with an enzyme that introduces or removes post-translational modifications.

39. The method of claim 1, further comprising contacting said immobilized amino acid sequence with a first enzyme that removes a post-translational modification and subsequently with a second enzyme that introduces a post-translational modification.

40. The method of claim 4, wherein said post-translational modification is selected from the group consisting of ubiquitination, SUMOlation, Agp12 ligation, and Nedd8 ligation.

41. The method of claim 9, wherein said post-translational modification is selected from the group consisting of ubiquitination, SUMOlation, Agp12 ligation, and Nedd8 ligation.

42. The method of claim 13, wherein said enzymatic activity is selected from the group consisting of ubiquitination, SUMOlation, Agp12 ligation, and Nedd8 ligation.

43. The method of claim 14, wherein said enzymatic activity is selected from the group consisting of ubiquitination, SUMOlation, Agp12 ligation, and Nedd8 ligation.

44. The method of claim 34, wherein said post-translational modification activity is selected from the group consisting of ubiquitination, SUMOlation, Agp12 ligation, and Nedd8 ligation.

45. The method of claim 35, wherein said enzymatic activity is selected from the group consisting of ubiquitination, SUMOlation, Agp12 ligation, and Nedd8 ligation.

46. The method of claim 13, wherein said captured amino acid sequence is purified prior to conducting a measurement of enzymatic activity.

47. The method of claim 46, wherein said purification comprises a wash that dissociates recruited enzymes that are bound to said captured amino acid sequence.

48. The method of claim 47, further comprising repeating said method with no wash or a wash that does not dissociate said recruited enzymes from said captured amino acid sequence, so as to identify amino acid sequences that recruit enzymes with said enzymatic activity.

49. The method of claim 1, wherein steps b–d are conducted within the same well.

50. The method of claim 13 or 15, wherein said enzymatic activity is selected from the group consisting of kinases, hydrolases, protease, polymerases, glycosidases, and phosphatases.

51. A method for screening nucleic acid constructs for those encoding amino acid sequences subject to a post-translational modification activity comprising the following steps;

(a) obtaining a nucleic acid construct coding for an amino acid sequence and an affinity tag,
(b) transcribing said nucleic acid to generate RNA,
(c) translating said RNA in a cell-free system containing a substrate that can be linked to a protein to form a post-transitional modification, to produce an amino acid sequence containing said affinity tag and said post-translational modification,
(d) immobilizing said amino acid sequence on a solid phase surface using binding species specific for said post-translational modification, and
(e) detecting said amino acid sequence using a binding reagent specific for said affinity tag.

52. A method for screening nucleic acid constructs for those encoding amino acid sequences with enzymatic activity comprising the following steps:

(a) obtaining a nucleic acid construct coding for an amino acid sequence and an affinity tag,
(b) transcribing said nucleic acid to generate RNA,
(c) translating said RNA in a cell-free system to produce an amino acid sequence linked to said affinity tag, and
(d) detecting enzymatic activity of said amino acid sequence using a method comprising the following steps:
  i) capturing said amino acid sequence onto a solid phase via an immobilized binding reagent specific for said affinity tag,
  ii) adding enzyme reaction buffer, and
  iii) detecting the product of the enzyme activity.

* * * * *

SEQUENCE LISTING

<160> NUMBER OF SEQ ID NOS: 23

<210> SEQ ID NO 1

-continued

```
<211> LENGTH: 24
<212> TYPE: PRT
<213> ORGANISM: Artificial Sequence
<220> FEATURE:
<223> OTHER INFORMATION: Synthetic Fragment of IkBa-p
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 1

Leu Lys Lys Glu Arg Leu Leu Asp Asp Arg His Asp Ser Gly Leu Asp
1               5                   10                  15

Ser Met Lys Asp Glu Glu Tyr Cys
            20


<210> SEQ ID NO 2
<211> LENGTH: 24
<212> TYPE: PRT
<213> ORGANISM: Artificial Sequence
<220> FEATURE:
<223> OTHER INFORMATION: Synthetic Fragment of IkBa

<400> SEQUENCE: 2

Leu Lys Lys Glu Arg Leu Leu Asp Asp Arg His Asp Ser Gly Leu Asp
1               5                   10                  15

Ser Met Lys Asp Glu Glu Tyr Cys
            20


<210> SEQ ID NO 3
<211> LENGTH: 26
<212> TYPE: PRT
<213> ORGANISM: Artificial Sequence
<220> FEATURE:
<223> OTHER INFORMATION: Synthetic Fragment of c-Myc

<400> SEQUENCE: 3

Cys Pro Ser Glu Asp Ile Trp Lys Lys Phe Glu Leu Leu Pro Thr Pro
1               5                   10                  15

Pro Leu Ser Pro Ser Arg Arg Ser Gly Leu
            20                  25


<210> SEQ ID NO 4
<211> LENGTH: 26
<212> TYPE: PRT
<213> ORGANISM: Artificial Sequence
<220> FEATURE:
<223> OTHER INFORMATION: Synthetic Fragment of c-Myc-p
<220> FEATURE:
<221> NAME/KEY: MOD_RES
<222> LOCATION: (15)..(15)
<223> OTHER INFORMATION: Phosphorylated
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (19)..(19)
<223> OTHER INFORMATION: Phosphorylated

<400> SEQUENCE: 4

Cys Pro Ser Glu Asp Ile Trp Lys Lys Phe Glu Leu Leu Pro Thr Pro
1               5                   10                  15
```

-continued

```
Pro Leu Ser Pro Ser Arg Arg Ser Gly Leu
            20                  25


<210> SEQ ID NO 5
<211> LENGTH: 20
<212> TYPE: PRT
<213> ORGANISM: Artificial Sequence
<220> FEATURE:
<223> OTHER INFORMATION: Synthetic Fragment of EGFR-pY992
<220> FEATURE:
<221> NAME/KEY: MOD_RES
<222> LOCATION: (5)..(5)
<223> OTHER INFORMATION: Phosphorylated
<220> FEATURE:
<221> NAME/KEY: MOD_RES
<222> LOCATION: (5)..(5)
<223> OTHER INFORMATION: PHOSPHORYLATION

<400> SEQUENCE: 5

Asp Ala Asp Glu Tyr Leu Ile Pro Gln Gln Gly Phe Phe Ser Ser Pro
1               5                   10                  15

Ser Thr Ser Cys
            20


<210> SEQ ID NO 6
<211> LENGTH: 20
<212> TYPE: PRT
<213> ORGANISM: Artificial Sequence
<220> FEATURE:
<223> OTHER INFORMATION: Synthetic Fragment of EGFR-Y992

<400> SEQUENCE: 6

Asp Ala Asp Glu Tyr Leu Ile Pro Gln Gln Gly Phe Phe Ser Ser Pro
1               5                   10                  15

Ser Thr Ser Cys
            20


<210> SEQ ID NO 7
<211> LENGTH: 20
<212> TYPE: PRT
<213> ORGANISM: Artificial Sequence
<220> FEATURE:
<223> OTHER INFORMATION: Synthetic Fragment of EGFR-pY1068
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (6)..(6)
<223> OTHER INFORMATION: PHOSPHORYLATION

<400> SEQUENCE: 7

Leu Pro Val Pro Glu Tyr Ile Asn Gln Ser Val Pro Lys Arg Pro Ala
1               5                   10                  15

Gly Ser Val Cys
            20


<210> SEQ ID NO 8
<211> LENGTH: 20
<212> TYPE: PRT
<213> ORGANISM: Artificial Sequence
<220> FEATURE:
<223> OTHER INFORMATION: Synthetic Fragment of EGFR-Y1068

<400> SEQUENCE: 8

Leu Pro Val Pro Glu Tyr Ile Asn Gln Ser Val Pro Lys Arg Pro Ala
1               5                   10                  15
```

-continued

```
Gly Ser Val Cys
            20


<210> SEQ ID NO 9
<211> LENGTH: 26
<212> TYPE: PRT
<213> ORGANISM: Artificial Sequence
<220> FEATURE:
<223> OTHER INFORMATION: Synthetic Fragment of EGFR-pY1148
<220> FEATURE:
<221> NAME/KEY: MOD_RES
<222> LOCATION: (13)..(13)
<223> OTHER INFORMATION: PHOSPHORYLATION

<400> SEQUENCE: 9

Lys Gly Ser His Gln Ile Ser Leu Asp Asn Pro Asp Tyr Gln Gln Asp
1               5                   10                  15

Phe Phe Pro Lys Glu Ala Lys Pro Asn Cys
            20                  25


<210> SEQ ID NO 10
<211> LENGTH: 26
<212> TYPE: PRT
<213> ORGANISM: Artificial Sequence
<220> FEATURE:
<223> OTHER INFORMATION: Synthetic Fragment of EGFR-Y1148

<400> SEQUENCE: 10

Lys Gly Ser His Gln Ile Ser Leu Asp Asn Pro Asp Tyr Gln Gln Asp
1               5                   10                  15

Phe Phe Pro Lys Glu Ala Lys Pro Asn Cys
            20                  25


<210> SEQ ID NO 11
<211> LENGTH: 25
<212> TYPE: PRT
<213> ORGANISM: Artificial Sequence
<220> FEATURE:
<223> OTHER INFORMATION: Synthetic Fragment of Smad3C-p
<220> FEATURE:
<221> NAME/KEY: MOD_RES
<222> LOCATION: (23)..(23)
<223> OTHER INFORMATION: Phosphorylated
<220> FEATURE:
<221> NAME/KEY: MOD_RES
<222> LOCATION: (25)..(25)
<223> OTHER INFORMATION: Phosphorylated

<400> SEQUENCE: 11

Cys Gly Pro Leu Gln Trp Leu Asp Lys Val Leu Thr Gln Met Gly Ser
1               5                   10                  15

Pro His Asn Pro Ile Ser Ser Val Ser
            20                  25


<210> SEQ ID NO 12
<211> LENGTH: 25
<212> TYPE: PRT
<213> ORGANISM: Artificial Sequence
<220> FEATURE:
<223> OTHER INFORMATION: Synthetic Fragment of Smad3C

<400> SEQUENCE: 12

Cys Gly Pro Leu Gln Trp Leu Asp Lys Val Leu Thr Gln Met Gly Ser
1               5                   10                  15

Pro His Asn Pro Ile Ser Ser Val Ser
            20                  25
```

-continued

<210> SEQ ID NO 13
<211> LENGTH: 57
<212> TYPE: DNA
<213> ORGANISM: Artificial Sequence
<220> FEATURE:
<223> OTHER INFORMATION: Synthetic oligonucleotide primer 1 for flag-bTRCP

<400> SEQUENCE: 13
tatgtcgaca tggattataa ggatgacgat gacaaagacc cggcagaggc ggtgctg 57

<210> SEQ ID NO 14
<211> LENGTH: 32
<212> TYPE: DNA
<213> ORGANISM: Artificial Sequence
<220> FEATURE:
<223> OTHER INFORMATION: Synthetic Oligonucleotide primer 2 for flag-bTRCP

<400> SEQUENCE: 14
tatgcggccg cttatctgga gatgtaggtg ta 32

<210> SEQ ID NO 15
<211> LENGTH: 37
<212> TYPE: DNA
<213> ORGANISM: Artificial Sequence
<220> FEATURE:
<223> OTHER INFORMATION: 5'ORI-tag-labeled synthetic oligonucleotide for YY1

<400> SEQUENCE: 15
acgtacgtac cgctccgcgg ccatcttggc ggctggt 37

<210> SEQ ID NO 16
<211> LENGTH: 37
<212> TYPE: DNA
<213> ORGANISM: Artificial Sequence
<220> FEATURE:
<223> OTHER INFORMATION: Synthetic oligonucleotide complement for YY1

<400> SEQUENCE: 16
accagccgcc aagatggccg cggagcggta cgtacgt 37

<210> SEQ ID NO 17
<211> LENGTH: 31
<212> TYPE: DNA
<213> ORGANISM: Artificial Sequence
<220> FEATURE:
<223> OTHER INFORMATION: 5' SH-X- Synthetic oligo AP1

<400> SEQUENCE: 17
actgactgac cgcttgatga ctcagccgga a 31

<210> SEQ ID NO 18
<211> LENGTH: 43
<212> TYPE: DNA
<213> ORGANISM: Artificial Sequence
<220> FEATURE:
<223> OTHER INFORMATION: 5' SH-X- Synthetic oligo Gluc

<400> SEQUENCE: 18
actgactgac gaccctagag gatctgtaca ggatgttcta gat 43

<210> SEQ ID NO 19
<211> LENGTH: 40

-continued

```
<212> TYPE: DNA
<213> ORGANISM: Artificial Sequence
<220> FEATURE:
<223> OTHER INFORMATION: 5' SH-X- Synthetic oligo P53

<400> SEQUENCE: 19

actgactgac tacagaacat gtctaagcat gctggggact                            40


<210> SEQ ID NO 20
<211> LENGTH: 37
<212> TYPE: DNA
<213> ORGANISM: Artificial Sequence
<220> FEATURE:
<223> OTHER INFORMATION: 5' SH-X- Synthetic oligo YY1

<400> SEQUENCE: 20

acgtacgtac cgctccgcgg ccatcttggc ggctggt                               37


<210> SEQ ID NO 21
<211> LENGTH: 30
<212> TYPE: DNA
<213> ORGANISM: Artificial Sequence
<220> FEATURE:
<223> OTHER INFORMATION: 5' SH-X- Synthetic oligo C/EBP

<400> SEQUENCE: 21

actgactgac tgcagattgc gcaatctgca                                       30


<210> SEQ ID NO 22
<211> LENGTH: 31
<212> TYPE: DNA
<213> ORGANISM: Artificial Sequence
<220> FEATURE:
<223> OTHER INFORMATION: 5' SH-X- Synthetic oligo HNF

<400> SEQUENCE: 22

actgactgac atctaggtca aaggtcatac t                                     31


<210> SEQ ID NO 23
<211> LENGTH: 37
<212> TYPE: DNA
<213> ORGANISM: Artificial Sequence
<220> FEATURE:
<223> OTHER INFORMATION: SH-X- Synthetic oligo CDP

<400> SEQUENCE: 23

actgactgac acccaatgat tattagccaa tttctga                               37
```